US006787327B2

(12) United States Patent
Kan et al.

(10) Patent No.: US 6,787,327 B2
(45) Date of Patent: Sep. 7, 2004

(54) METHODS FOR DETERMINING TYROSINE-DNA PHOSPHODIESTERASE ACTIVITY

(75) Inventors: Chen-Chen Kan, Arcadia, CA (US); Ting-Jen Cheng, Pomona, CA (US)

(73) Assignee: Kelk Graduate of Applied Life Sciences, Claremont, CA (US)

( * ) Notice: Subject to any disclaimer, the term of this patent is extended or adjusted under 35 U.S.C. 154(b) by 0 days.

(21) Appl. No.: 10/265,012

(22) Filed: Oct. 4, 2002

(65) Prior Publication Data

US 2003/0124587 A1 Jul. 3, 2003

Related U.S. Application Data

(60) Provisional application No. 60/327,466, filed on Oct. 5, 2001.

(51) Int. Cl.[7] .............................. C12Q 1/34; C12N 9/16
(52) U.S. Cl. ......................................... 435/18; 435/196
(58) Field of Search ................................... 435/18, 196

(56) References Cited

U.S. PATENT DOCUMENTS

| 4,683,195 A | 7/1987 | Mullis et al. ................... 435/6 |
| 4,683,202 A | 7/1987 | Mullis .......................... 435/91 |
| 4,965,188 A | 10/1990 | Mullis et al. ................... 435/6 |
| 5,322,770 A | 6/1994 | Gelfand ......................... 435/91 |

FOREIGN PATENT DOCUMENTS

| WO | WO 01/02568 | 1/2001 |
| WO | WO 01/25407 | 4/2001 |
| WO | WO 01/29221 | 4/2001 |

OTHER PUBLICATIONS

Isogai et al. (Feb. 23, 2000) GenBank accession AK001952.*
Pouliot et al., Science 286:552 [1999].
Wang, Ann. Rev. Biochem., 65:635 [1996].
Chen et al., Ann. Rev. Pharmacol. Toxicol., 94:194 [1994].
Pommier et al., Biochem. Biophys. Acta 1400:83 [1998].
Friedberg et al., *DNA Repair and Mutagenesis*, ASM Press, Washington, D.C. [1995].
Kanaar et al., Trends Cell. Biol., 8:483 [1998].
Yang et al., Proc. Natl. Acad. Sci. USA 93:11534–11539 [1996].
Pouliot et al., Science 286:552–555 [1999].
Dunlop et al., Mech. Develop., 96:133–136 [2000].
Interthal et al., Proc. Natl. Acad. Sci., early edition [2001].
Champoux, *Mechanistic Aspects of Type–I Topoisomerase*, Cold Spring Harbor Laboratory, Cold Spring Harbor [1990].
Kjeldsen et al., J. Mol. Biol., 228:1025–1030 [1992].
Hertzberg et al., in Potemsil et al. (eds.), *DNA Topoisomerase in Cancer*, Oxford University Press, NY [1991], pp.103–120.
Kingsbury et al., J. Med. Chem., 34:98–107 [1991].
Del Bino et al., Cancer Res. 50:5746–5750 [1990].
Gottieb et al., Cancer Chemo. Ther. Rep., 54:461–4470 [1970].
Fan et al., J. Med. Chem., 41:2216–2226 [1998].
Maniatis et al., Science 236:1237 [1987].
Voss et al., Trends Biochem. Sci., 11:287 [1986].
R. Dijkema et al., EMBO J. 4:761 [1985].
Uetsuki et al., J. Biol. Chem., 264:5791 [1989].
D.W. Kim et al., Gene 91:217 [1990].
Mizushima and Nagata, Nucl. Acids. Res., 18:5322 [1990].
Gorman et al., Proc. Natl. Acad. Sci. USA 79:6777 [1982].
Boshart et al., Cell 41:521 [1985].
Sambrook et al., *Molecular Cloning: A Laboratory Manual*, 2nd ed., Cold Spring Harbor Laboratory Press, New York [1989], pp. 16.7–16.8.
Anderson and Young, "Quantitative Filter Hybridization," in *Nucleic Acid Hybridization* [1985].
Schmike et al. Science 202:1051 [1978].
Kaufman, Meth. Enzymol., 185:537 [1990].
Kacian et al., Proc. Natl. Acad. Sci. USA 69:3038 [1972].
Chamberlin et al., Nature 228:227 [1970].
Wu and Wallace, Genomics 4:560 [1989].
Erlich (ed.), *PCR Technology*, Stockton Press [1989].
Graham and van der Eb, Virol., 52:456 [1973].
Ausubel et al., *Current Protocols in Molecular Biology*, Greene Publishing Association and Wiley–Interscience [1987].
Turner et al., J. Am. Chem. Soc., 81:4651–4656 [1959].
Giovanella et al., Science 246:1046–1048 (1989).
Potmesil, Cancer Res. 54:1431–1930 (1994).
Gehring et al., J. Biol. Chem. 270(38)22507–22513 (1995).
Mossakowska, Curr. Opin. Biotechnol. 9:502–505 (1998).

* cited by examiner

Primary Examiner—Elizabeth Slobodyansky
(74) Attorney, Agent, or Firm—Medlen & Carroll, LLP

(57) ABSTRACT

The present invention provides human tyrosine-DNA phosphodiesterases (TDPs). In particular, the present invention provides novel recombinant nucleic acids and proteins, including mutant TDPs, vectors, and TDP-producing cells, as well as co-factors for enzyme activity. The present invention further provides methods for high through-put enzymatic assay systems utilizing the TDPs of the present invention.

6 Claims, 23 Drawing Sheets

FIGURE 2

SEQ ID NO 1

| | | | | | | | | | | | | | | | |
|---|---|---|---|---|---|---|---|---|---|---|---|---|---|---|---|
| atg | tct | cag | gaa | ggc | gat | tat | ggg | agg | tgg | acc | ata | tct | agt | agt | 45 |
| Met | Ser | Gln | Glu | Gly | Asp | Tyr | Gly | Arg | Trp | Thr | Ile | Ser | Ser | Ser | |
| 1 | | | | 5 | | | | | 10 | | | | | 15 | |
| gat | gaa | agt | gag | gaa | gaa | aag | cca | aaa | cca | gac | aag | cca | tct | acc | 90 |
| Asp | Glu | Ser | Glu | Glu | Glu | Lys | Pro | Lys | Pro | Asp | Lys | Pro | Ser | Thr | |
| 16 | | | | 20 | | | | | 25 | | | | | 30 | |
| tct | tct | ctt | ctc | tgt | gcc | agg | caa | gga | gca | gca | aat | gag | ccc | agg | 135 |
| Ser | Ser | Leu | Leu | Cys | Ala | Arg | Gln | Gly | Ala | Ala | Asn | Glu | Pro | Arg | |
| 31 | | | | 35 | | | | | 40 | | | | | 45 | |
| tac | acc | tgt | tcc | gag | gcc | cag | aaa | gct | gca | cac | aag | agg | aaa | ata | 180 |
| Tyr | Thr | Cys | Ser | Glu | Ala | Gln | Lys | Ala | Ala | His | Lys | Arg | Lys | Ile | |
| 46 | | | | 50 | | | | | 55 | | | | | 60 | |
| tca | cct | gtg | aaa | ttc | agc | aat | aca | gat | tca | gtt | tta | cct | ccc | aaa | 225 |
| Ser | Pro | Val | Lys | Phe | Ser | Asn | Thr | Asp | Ser | Val | Leu | Pro | Pro | Lys | |
| 61 | | | | 65 | | | | | 70 | | | | | 75 | |
| agg | cag | aaa | agc | ggt | tcc | cag | gag | gac | ctc | ggc | tgg | tgt | ctg | tcc | 270 |
| Arg | Gln | Lys | Ser | Gly | Ser | Gln | Glu | Asp | Leu | Gly | Trp | Cys | Leu | Ser | |
| 76 | | | | 80 | | | | | 85 | | | | | 90 | |
| agc | agt | gat | gat | gag | ctg | caa | cca | gaa | atg | ccg | cag | aag | cag | gct | 315 |
| Ser | Ser | Asp | Asp | Glu | Leu | Gln | Pro | Glu | Met | Pro | Gln | Lys | Gln | Ala | |
| 91 | | | | 95 | | | | | 100 | | | | | 105 | |
| gag | aaa | gtg | gtg | atc | aaa | aag | gag | aaa | gac | atc | tct | gct | ccc | aat | 360 |
| Glu | Lys | Val | Val | Ile | Lys | Lys | Glu | Lys | Asp | Ile | Ser | Ala | Pro | Asn | |
| 106 | | | | 110 | | | | | 115 | | | | | 120 | |
| gac | ggc | act | gcc | caa | agt | act | gaa | aat | cat | ggg | gct | ccc | gcc | tgc | 405 |
| Asp | Gly | Thr | Ala | Gln | Ser | Thr | Glu | Asn | His | Gly | Ala | Pro | Ala | Cys | |
| 121 | | | | 125 | | | | | 130 | | | | | 135 | |
| cac | agg | ctc | aaa | gag | gag | gaa | gac | gag | tat | gag | aca | tca | ggg | gag | 450 |
| His | Arg | Leu | Lys | Glu | Glu | Glu | Asp | Glu | Tyr | Glu | Thr | Ser | Gly | Glu | |
| 136 | | | | 140 | | | | | 145 | | | | | 150 | |
| ggc | cag | gac | att | tgg | gac | atg | ctg | gat | aaa | agg | aac | ccc | ttc | cag | 495 |
| Gly | Gln | Asp | Ile | Trp | Asp | Met | Leu | Asp | Lys | Arg | Asn | Pro | Phe | Gln | |
| 151 | | | | 155 | | | | | 160 | | | | | 165 | |
| ttt | tac | ctc | act | aga | gtc | tct | gga | gtt | aag | cca | aag | tat | aac | tct | 540 |
| Phe | Tyr | Leu | Thr | Arg | Val | Ser | Gly | Val | Lys | Pro | Lys | Tyr | Asn | Ser | |
| 166 | | | | 170 | | | | | 175 | | | | | 180 | |
| gga | gcc | ctc | cac | atc | aag | gat | att | tta | tct | cct | tta | ttt | ggg | acg | 585 |
| Gly | Ala | Leu | His | Ile | Lys | Asp | Ile | Leu | Ser | Pro | Leu | Phe | Gly | Thr | |
| 181 | | | | 185 | | | | | 190 | | | | | 195 | |
| ctt | gtt | tct | tca | gct | cag | ttt | aac | tac | tgc | ttt | gac | gtg | gac | tgg | 630 |
| Leu | Val | Ser | Ser | Ala | Gln | Phe | Asn | Tyr | Cys | Phe | Asp | Val | Asp | Trp | |
| 196 | | | | 200 | | | | | 205 | | | | | 210 | |
| ctc | gta | aaa | cag | tat | cca | cca | gaa | ttc | cgt | aag | aag | cca | atc | ctg | 675 |
| Leu | Val | Lys | Gln | Tyr | Pro | Pro | Glu | Phe | Arg | Lys | Lys | Pro | Ile | Leu | |
| 211 | | | | 215 | | | | | 220 | | | | | 225 | |

FIGURE 2 (CONT.)

```
ctt gtg cat ggt gat aag cga gag gct aag gct cac ctc cat gcc        720
Leu Val His Gly Asp Lys Arg Glu Ala Lys Ala His Leu His Ala
226             230                 235                 240
cag gcc aag cct tac gag aac atc tct ctc tgc cag gca aag ttg        765
Gln Ala Lys Pro Tyr Glu Asn Ile Ser Leu Cys Gln Ala Lys Leu
241             245                 250                 255
gat att gcg ttt gga aca cac cac acg aaa atg atg ctg ctg ctc        810
Asp Ile Ala Phe Gly Thr His His Thr Lys Met Met Leu Leu Leu
256             260                 265                 270
tat gaa gaa ggc ctc cgg gtt gtc ata cac acc tcc aac ctc atc        855
Tyr Hlu Glu Gly Leu Arg Val Val Ile His Thr Ser Asn Leu Ile
271             275                 280                 285
cat gct gac tgg cac cag aaa act caa gga ata tgg ttg agc ccc        900
His Ala Asp Trp His Gln Lys Thr Gln Gly Ile Trp Leu Ser Pro
286             290                 295                 300
tta tac cca cga att gct gat gga acc cac aaa tct gga gag tcg        945
Leu Tyr Pro Arg Ile Ala Asp Gly Thr His Lys Ser Gly Glu Ser
301             305                 310                 315
cca aca cat ttt aaa gct gat ctc atc agt tac ttg atg gct tat        990
Pro THr His Phe Lys Ala Asp Leu Ile Ser Tyr Leu Met Ala Tyr
316             320                 325                 330
aat gcc cct tct ctc aag gag tgg ata gat gtc att cac aag cac       1035
Asn Ala Pro Ser Leu Lys Glu Trp Ile Asp Val Ile His Lys His
331             335                 340                 345
gat ctc tct gaa aca aat gtt tat ctt att ggt tca acc cca gga       1080
Asp Leu Ser Glu Thr Asn Val Tyr Leu Ile Gly Ser Thr Pro Gly
346             350                 355                 360
cgc ttt caa gga agt caa aaa gat aat tgg gga cat ttt aga ctt       1125
Arg Phe Gln Gly Ser Gln Lys Asp Asn Trp Gly His Phe Arg Leu
361             365                 370                 375
aag aag ctt ctg aaa gac cat gcc tca tcc atg cct aac cca gag       1170
Lys Lys Leu Leu Lys Asp His Ala Ser Ser Met Pro Asn Pro Glu
376             380                 385                 390
tcc tgg cct gtc gta ggt cag ttt tca agc gtt ggc tcc ttg gga       1215
Ser Trp Pto Val Val Gly Gln Phe Ser Ser Val Gly Ser Leu Gly
391             395                 400                 405
gcc gat gaa tca aag tgg tta tgt tct gag ttt aaa gag agc atg       1260
Ala Asp Glu Ser Lys Trp Leu Cys Ser Glu Phe Lys Glu Ser Met
406             410                 415                 420
ctg aca ctg ggg aag gaa agc aag act cca gga aaa agc tct gtt       1305
Leu Thr Leu Gly Lys Glu Ser Lys Thr Pro Gly Lys Ser Ser Val
421             425                 430                 435
cct ctt tac ttg atc tat cct tct gtg gaa aat gtg cgg acc agt       1350
Pro Leu Tyr Leu Ile Tyr Pro Ser Val Glu Asn Val Arg Thr Ser
436             440                 445                 450
tta gaa gga tat cct gct ggg ggc tct ctt ccc tat agc atc cag       1395
Leu Glu Gly Tyr Pro Ala Gly Gly Ser Leu Pro Tyr Ser Ile Gln
451             455                 460                 465
aca gct gaa aaa cag aat tgg ctg cat tcc tat ttt cac aaa tgg       1440
Thr Ala Glu Lys Gln Asn Trp Leu His Ser Tyr Phe His Lys Trp
466             470                 475                 480
tca gct gag act tct ggc cgc agc aat gcc atg cca cat att aag       1485
Ser Ala Glu Thr Ser Gly Arg Ser Asn Ala Met Pro His Ile Lys
481             485                 490                 495
aca tat atg agg cct tct cca gac ttc agt aaa att gct tgg ttc       1530
Thr Tyr Met Arg Pro Ser Pro Asp Phe Ser Lys Ile Ala Trp Phe
496             500                 505                 510
```

FIGURE 2 (CONT.)

```
ctt gtc aca agc gca aat ctg tcc aag gct gcc tgg gga gca ttg    1575
Leu Val Thr Ser Ala Asn Leu Ser Lys Ala Ala Trp Gly Ala Leu
511             515                 520                 525
gag aag aat ggc acc cag ctg atg atc cgc tcc tac gag ctc ggg    1620
Glu Lys Asn Gly Thr Gln Leu Met Ile Arg Ser Tyr Glu Leu Gly
526             530                 535                 540
gtc ctt ttt ctc cct tca gca ttt ggt cta gac agt ttc aaa gtg    1665
Val Leu Phe Leu Pro Ser Ala Phe Gly Leu Asp Ser Phe Lys Val
541             545                 550                 555
aaa cag aag ttc ttc gct ggc agc cag gag cca atg gcc acc ttt    1710
Lys Gln Lys Phe Phe Ala Gly Ser Gln Glu Pro Met Ala Thr Phe
556             560                 565                 570
cct gtg cca tat gat ttg cct cca gaa ctg tat gga agt aaa gat    1755
Pro Val Pro Tyr Asp Leu Pro Pro Glu Leu Tyr Gly Ser Lys Asp
571             575                 580                 585
cgg cca tgg ata tgg aac att cct tat gtc aaa gca ccg gat acg    1800
Arg Pro Trp Ile Trp Asn Ile Pro Tyr Val Lys Ala Pro Asp Thr
586             590                 595                 600
cat ggg aac atg tgg gtg ccc tcc                                1824
His Gly Asn Met Trp Val Pro Ser
601             605         608
```

SEQ ID NO 2

```
Met Ser Gln Glu Gly Asp Tyr Gly Arg Trp Thr Ile Ser Ser Ser
1               5                   10                  15
Asp Glu Ser Glu Glu Lys Pro Lys Pro Asp Lys Pro Ser Thr
16              20                  25                  30
Ser Ser Leu Leu Cys Ala Arg Gln Gly Ala Ala Asn Glu Pro Arg
31              35                  40                  45
Tyr Thr Cys Ser Glu Ala Gln Lys Ala Ala His Lys Arg Lys Ile
46              50                  55                  60
Ser Pro Val Lys Phe Ser Asn Thr Asp Ser Val Leu Pro Pro Lys
61              65                  70                  75
Arg Gln Lys Ser Gly Ser Gln Glu Asp Leu Gly Trp Cys Leu Ser
76              80                  85                  90
Ser Ser Asp Asp Glu Leu Gln Pro Glu Met Pro Gln Lys Gln Ala
91              95                  100                 105
Glu Lys Val Val Ile Lys Lys Glu Lys Asp Ile Ser Ala Pro Asn
106             110                 115                 120
Asp Gly Thr Ala Gln Ser Thr Glu Asn His Gly Ala Pro Ala Cys
121             125                 130                 135
His Arg Leu Lys Glu Glu Asp Glu Tyr Glu Thr Ser Gly Glu
136             140                 145                 150
Gly Gln Asp Ile Trp Asp Met Leu Asp Lys Arg Asn Pro Phe Gln
151             155                 160                 165
Phe Tyr Leu Thr Arg Val Ser Gly Val Lys Pro Lys Tyr Asn Ser
166             170                 175                 180
Gly Ala Leu His Ile Lys Asp Ile Leu Ser Pro Leu Phe Gly Thr
181             185                 190                 195
Leu Val Ser Ser Ala Gln Phe Asn Tyr Cys Phe Asp Val Asp Trp
196             200                 205                 210
Leu Val Lys Gln Tyr Pro Pro Glu Phe Arg Lys Lys Pro Ile Leu
211             215                 220                 225
```

FIGURE 2 (CONT.)

```
Leu Val His Gly Asp Lys Arg Glu Ala Lys Ala His Leu His Ala
226             230             235             240
Gln Ala Lys Pro Tyr Glu Asn Ile Ser Leu Cys Gln Ala Lys Leu
241             245             250             255
Asp Ile Ala Phe Gly Thr His His Thr Lys Met Met Leu Leu Leu
256             260             265             270
Tyr Hlu Glu Gly Leu Arg Val Val Ile His Thr Ser Asn Leu Ile
271             275             280             285
His Ala Asp Trp His Gln Lys Thr Gln Gly Ile Trp Leu Ser Pro
286             290             295             300
Leu Tyr Pro Arg Ile Ala Asp Gly Thr His Lys Ser Gly Glu Ser
301             305             310             315
Pro THr His Phe Lys Ala Asp Leu Ile Ser Tyr Leu Met Ala Tyr
316             320             325             330
Asn Ala Pro Ser Leu Lys Glu Trp Ile Asp Val Ile His Lys His
331             335             340             345
Asp Leu Ser Glu Thr Asn Val Tyr Leu Ile Gly Ser Thr Pro Gly
346             350             355             360
Arg Phe Gln Gly Ser Gln Lys Asp Asn Trp Gly His Phe Arg Leu
361             365             370             375
Lys Lys Leu Leu Lys Asp His Ala Ser Ser Met Pro Asn Pro Glu
376             380             385             390
Ser Trp Pto Val Val Gly Gln Phe Ser Ser Val Gly Ser Leu Gly
391             395             400             405
Ala Asp Glu Ser Lys Trp Leu Cys Ser Glu Phe Lys Glu Ser Met
406             410             415             420
Leu Thr Leu Gly Lys Glu Ser Lys Thr Pro Gly Lys Ser Ser Val
421             425             430             435
Pro Leu Tyr Leu Ile Tyr Pro Ser Val Glu Asn Val Arg Thr Ser
436             440             445             450
Leu Glu Gly Tyr Pro Ala Gly Gly Ser Leu Pro Tyr Ser Ile Gln
451             455             460             465
Thr Ala Glu Lys Gln Asn Trp Leu His Ser Tyr Phe His Lys Trp
466             470             475             480
Ser Ala Glu Thr Ser Gly Arg Ser Asn Ala Met Pro His Ile Lys
481             485             490             495
Thr Tyr Met Arg Pro Ser Pro Asp Phe Ser Lys Ile Ala Trp Phe
496             500             505             510
Leu Val Thr Ser Ala Asn Leu Ser Lys Ala Ala Trp Gly Ala Leu
511             515             520             525
Glu Lys Asn Gly Thr Gln Leu Met Ile Arg Ser Tyr Glu Leu Gly
526             530             535             540
Val Leu Phe Leu Pro Ser Ala Phe Gly Leu Asp Ser Phe Lys Val
541             545             550             555
Lys Gln Lys Phe Phe Ala Gly Ser Gln Glu Pro Met Ala Thr Phe
556             560             565             570
Pro Val Pro Tyr Asp Leu Pro Pro Glu Leu Tyr Gly Ser Lys Asp
571             575             580             585
Arg Pro Trp Ile Trp Asn Ile Pro Tyr Val Lys Ala Pro Asp Thr
586             590             595             600
His Gly Asn Met Trp Val Pro Ser
601             605             608
```

FIGURE 2 (CONT.)

SEQ ID NO 3

GCA GCA AAT GAG CCC AGG TAC ACC TGT TCC         30

SEQ ID NO 4

GGA GGG CAC CCA CAT GTT CCC ATG C         25

SEQ ID NO 5

AAG TAT AAC TCT CGA GCC CTC CAC ATC AAG G         31

SEQ ID NO 6

TGA AGG GAG GAA AAG GAC CCC GAG C         25

SEQ ID NO 7

```
gca gca aat gag ccc agg tac acc tgt tcc gag gcc cag aaa gct      45
Ala Ala Asn Glu Pro Arg Tyr Thr Cys Ser Glu Ala Gln Lys Ala
 1           5                  10                  15
gca cac aag agg aaa ata tca cct gtg aaa ttc agc aat aca gat      90
Ala His Lys Arg Lys Ile Ser Pro Val Lys Phe Ser Asn Thr Asp
16          20                  25                  30
tca gtt tta cct ccc aaa agg cag aaa agc ggt tcc cag gag gac     135
Ser Val Leu Pro Pro Lys Arg Gln Lys Ser Gly Ser Gln Glu Asp
31          35                  40                  45
ctc ggc tgg tgt ctg tcc agc agt gat gat gag ctg caa cca gaa     180
Leu Gly Trp Cys Leu Ser Ser Ser Asp Asp Glu Leu Gln Pro Glu
46          50                  55                  60
atg ccg cag aag cag gct gag aaa gtg gtg atc aaa aag gag aaa     225
Met Pro Gln Lys Gln Ala Glu Lys Val Val Ile Lys Lys Glu Lys
61          65                  70                  75
gac atc tct gct ccc aat gac ggc act gcc caa agt act gaa aat     270
Asp Ile Ser Ala Pro Asn Asp Gly Thr Ala Gln Ser Thr Glu Asn
76          80                  85                  90
cat ggg gct ccc gcc tgc cac agg ctc aaa gag gag gaa gac gag     315
His Gly Ala Pro Ala Cys His Arg Leu Lys Glu Glu Glu Asp Glu
```

FIGURE 2 (CONT.)

```
     91               95               100              105
    tat gag aca tca ggg gag ggc cag gac att tgg gac atg ctg gat        360
    Tyr Glu Thr Ser Gly Glu Gly Gln Asp Ile Trp Asp Met Leu Asp
    106              110              115              120
    aaa agg aac ccc ttc cag ttt tac ctc act aga gtc tct gga gtt        405
    Lys Arg Asn Pro Phe Gln Phe Tyr Leu Thr Arg Val Ser Gly Val
    121              125              130              135
    aag cca aag tat aac tct gga gcc ctc cac atc aag gat att tta        450
    Lys Pro Lys Tyr Asn Ser Gly Ala Leu His Ile Lys Asp Ile Leu
    136              140              145              150
    tct cct tta ttt ggg acg ctt gtt tct tca gct cag ttt aac tac        495
    Ser Pro Leu Phe Gly Thr Leu Val Ser Ser Ala Gln Phe Asn Tyr
    151              155              160              165
    tgc ttt gac gtg gac tgg ctc gta aaa cag tat cca cca gaa ttc        540
    Cys Phe Asp Val Asp Trp Leu Val Lys Gln Tyr Pro Pro Glu Phe
    166              170              175              180
    cgt aag aag cca atc ctg ctt gtg cat ggt gat aag cga gag gct        585
    Arg Lys Lys Pro Ile Leu Leu Val His Gly Asp Lys Arg Glu Ala
    181              185              190              195
    aag gct cac ctc cat gcc cag gcc aag cct tac gag aac atc tct        630
    Lys Ala His Leu His Ala Gln Ala Lys Pro Tyr Glu Asn Ile Ser
    196              200              205              210
    ctc tgc cag gca aag ttg gat att gcg ttt gga aca cac cac acg        675
    Leu Cys Gln Ala Lys Leu Asp Ile Ala Phe Gly Thr His His Thr
    211              215              220              225
    aaa atg atg ctg ctg ctc tat gaa gaa ggc ctc cgg gtt gtc ata        720
    Lys Met Met Leu Leu Leu Tyr Hlu Glu Gly Leu Arg Val Val Ile
    226              230              235              240
    cac acc tcc aac ctc atc cat gct gac tgg cac cag aaa act caa        765
    His Thr Ser Asn Leu Ile His Ala Asp Trp His Gln Lys Thr Gln
    241              245              250              255
    gga ata tgg ttg agc ccc tta tac cca cga att gct gat gga acc        810
    Gly Ile Trp Leu Ser Pro Leu Tyr Pro Arg Ile Ala Asp Gly Thr
    256              260              265              270
    cac aaa tct gga gag tcg cca aca cat ttt aaa gct gat ctc atc        855
    His Lys Ser Gly Glu Ser Pro THr His Phe Lys Ala Asp Leu Ile
    271              275              280              285
    agt tac ttg atg gct tat aat gcc cct tct ctc aag gag tgg ata        900
    Ser Tyr Leu Met Ala Tyr Asn Ala Pro Ser Leu Lys Glu Trp Ile
    286              290              295              300
    gat gtc att cac aag cac gat ctc tct gaa aca aat gtt tat ctt        945
    Asp Val Ile His Lys His Asp Leu Ser Glu Thr Asn Val Tyr Leu
    301              305              310              315
    att ggt tca acc cca gga cgc ttt caa gga agt caa aaa gat aat        990
    Ile Gly Ser Thr Pro Gly Arg Phe Gln Gly Ser Gln Lys Asp Asn
    316              320              325              330
    tgg gga cat ttt aga ctt aag aag ctt ctg aaa gac cat gcc tca       1035
    Trp Gly His Phe Arg Leu Lys Lys Leu Leu Lys Asp His Ala Ser
    331              335              340              345
    tcc atg cct aac cca gag tcc tgg cct gtc gta ggt cag ttt tca       1080
    Ser Met Pro Asn Pro Glu Ser Trp Pto Val Val Gly Gln Phe Ser
    346              350              355              360
    agc gtt ggc tcc ttg gga gcc gat gaa tca aag tgg tta tgt tct       1125
    Ser Val Gly Ser Leu Gly Ala Asp Glu Ser Lys Trp Leu Cys Ser
    361              365              370              375
    gag ttt aaa gag agc atg ctg aca ctg ggg aag gaa agc aag act       1170
    Glu Phe Lys Glu Ser Met Leu Thr Leu Gly Lys Glu Ser Lys Thr
```

FIGURE 2 (CONT.)

```
376                 380                 385                 390
cca gga aaa agc tct gtt cct ctt tac ttg atc tat cct tct gtg    1215
Pro Gly Lys Ser Ser Val Pro Leu Tyr Leu Ile Tyr Pro Ser Val
391                 395                 400                 405
gaa aat gtg cgg acc agt tta gaa gga tat cct gct ggg ggc tct    1260
Glu Asn Val Arg Thr Ser Leu Glu Gly Tyr Pro Ala Gly Gly Ser
406                 410                 415                 420
ctt ccc tat agc atc cag aca gct gaa aaa cag aat tgg ctg cat    1305
Leu Pro Tyr Ser Ile Gln Thr Ala Glu Lys Gln Asn Trp Leu His
421                 425                 430                 435
tcc tat ttt cac aaa tgg tca gct gag act tct ggc cgc agc aat    1350
Ser Tyr Phe His Lys Trp Ser Ala Glu Thr Ser Gly Arg Ser Asn
436                 440                 445                 450
gcc atg cca cat att aag aca tat atg agg cct tct cca gac ttc    1395
Ala Met Pro His Ile Lys Thr Tyr Met Arg Pro Ser Pro Asp Phe
451                 455                 460                 465
agt aaa att gct tgg ttc ctt gtc aca agc gca aat ctg tcc aag    1440
Ser Lys Ile Ala Trp Phe Leu Val Thr Ser Ala Asn Leu Ser Lys
466                 470                 475                 480
gct gcc tgg gga gca ttg gag aag aat ggc acc cag ctg atg atc    1485
Ala Ala Trp Gly Ala Leu Glu Lys Asn Gly Thr Gln Leu Met Ile
481                 485                 490                 495
cgc tcc tac gag ctc ggg gtc ctt ttt ctc cct tca gca ttt ggt    1530
Arg Ser Tyr Glu Leu Gly Val Leu Phe Leu Pro Ser Ala Phe Gly
496                 500                 505                 510
cta gac agt ttc aaa gtg aaa cag aag ttc ttc gct ggc agc cag    1575
Leu Asp Ser Phe Lys Val Lys Gln Lys Phe Phe Ala Gly Ser Gln
511                 515                 520                 525
gag cca atg gcc acc ttt cct gtg cca tat gat ttg cct cca gaa    1620
Glu Pro Met Ala Thr Phe Pro Val Pro Tyr Asp Leu Pro Pro Glu
526                 530                 535                 540
ctg tat gga agt aaa gat cgg cca tgg ata tgg aac att cct tat    1665
Leu Tyr Gly Ser Lys Asp Arg Pro Trp Ile Trp Asn Ile Pro Tyr
541                 545                 550                 555
gtc aaa gca ccg gat acg cat ggg aac atg tgg gtg ccc tcc        1707
Val Lys Ala Pro Asp Thr His Gly Asn Met Trp Val Pro Ser
556                 560                 565                 569
```

SEQ ID NO 8

```
Ala Ala Asn Glu Pro Arg Tyr Thr Cys Ser Glu Ala Gln Lys Ala
1                   5                   10                  15
Ala His Lys Arg Lys Ile Ser Pro Val Lys Phe Ser Asn Thr Asp
16                  20                  25                  30
Ser Val Leu Pro Pro Lys Arg Gln Lys Ser Gly Ser Gln Glu Asp
31                  35                  40                  45
Leu Gly Trp Cys Leu Ser Ser Ser Asp Asp Glu Leu Gln Pro Glu
46                  50                  55                  60
Met Pro Gln Lys Gln Ala Glu Lys Val Val Ile Lys Lys Glu Lys
61                  65                  70                  75
Asp Ile Ser Ala Pro Asn Asp Gly Thr Ala Gln Ser Thr Glu Asn
76                  80                  85                  90
His Gly Ala Pro Ala Cys His Arg Leu Lys Glu Glu Asp Glu
91                  95                  100                 105
Tyr Glu Thr Ser Gly Glu Gly Gln Asp Ile Trp Asp Met Leu Asp
```

FIGURE 2 (CONT.)

```
106              110                 115              120
Lys Arg Asn Pro Phe Gln Phe Tyr Leu Thr Arg Val Ser Gly Val
121              125                 130              135
Lys Pro Lys Tyr Asn Ser Gly Ala Leu His Ile Lys Asp Ile Leu
136              140                 145              150
Ser Pro Leu Phe Gly Thr Leu Val Ser Ser Ala Gln Phe Asn Tyr
151              155                 160              165
Cys Phe Asp Val Asp Trp Leu Val Lys Gln Tyr Pro Pro Glu Phe
166              170                 175              180
Arg Lys Lys Pro Ile Leu Leu Val His Gly Asp Lys Arg Glu Ala
181              185                 190              195
Lys Ala His Leu His Ala Gln Ala Lys Pro Tyr Glu Asn Ile Ser
196              200                 205              210
Leu Cys Gln Ala Lys Leu Asp Ile Ala Phe Gly Thr His His Thr
211              215                 220              225
Lys Met Met Leu Leu Leu Tyr Hlu Glu Gly Leu Arg Val Val Ile
226              230                 235              240
His Thr Ser Asn Leu Ile His Ala Asp Trp His Gln Lys Thr Gln
241              245                 250              255
Gly Ile Trp Leu Ser Pro Leu Tyr Pro Arg Ile Ala Asp Gly Thr
256              260                 265              270
His Lys Ser Gly Glu Ser Pro Thr His Phe Lys Ala Asp Leu Ile
271              275                 280              285
Ser Tyr Leu Met Ala Tyr Asn Ala Pro Ser Leu Lys Glu Trp Ile
286              290                 295              300
Asp Val Ile His Lys His Asp Leu Ser Glu Thr Asn Val Tyr Leu
301              305                 310              315
Ile Gly Ser Thr Pro Gly Arg Phe Gln Gly Ser Gln Lys Asp Asn
316              320                 325              330
Trp Gly His Phe Arg Leu Lys Lys Leu Leu Lys Asp His Ala Ser
331              335                 340              345
Ser Met Pro Asn Pro Glu Ser Trp Pto Val Val Gly Gln Phe Ser
346              350                 355              360
Ser Val Gly Ser Leu Gly Ala Asp Glu Ser Lys Trp Leu Cys Ser
361              365                 370              375
Glu Phe Lys Glu Ser Met Leu Thr Leu Gly Lys Glu Ser Lys Thr
376              380                 385              390
Pro Gly Lys Ser Ser Val Pro Leu Tyr Leu Ile Tyr Pro Ser Val
391              395                 400              405
Glu Asn Val Arg Thr Ser Leu Glu Gly Tyr Pro Ala Gly Gly Ser
406              410                 415              420
Leu Pro Tyr Ser Ile Gln Thr Ala Glu Lys Gln Asn Trp Leu His
421              425                 430              435
Ser Tyr Phe His Lys Trp Ser Ala Glu Thr Ser Gly Arg Ser Asn
436              440                 445              450
Ala Met Pro His Ile Lys Thr Tyr Met Arg Pro Ser Pro Asp Phe
451              455                 460              465
Ser Lys Ile Ala Trp Phe Leu Val Thr Ser Ala Asn Leu Ser Lys
466              470                 475              480
Ala Ala Trp Gly Ala Leu Glu Lys Asn Gly Thr Gln Leu Met Ile
481              485                 490              495
Arg Ser Tyr Glu Leu Gly Val Leu Phe Leu Pro Ser Ala Phe Gly
496              500                 505              510
Leu Asp Ser Phe Lys Val Lys Gln Lys Phe Phe Ala Gly Ser Gln
511              515                 520              525
Glu Pro Met Ala Thr Phe Pro Val Pro Tyr Asp Leu Pro Pro Glu
526              530                 535              540
Leu Tyr Gly Ser Lys Asp Arg Pro Trp Ile Trp Asn Ile Pro Tyr
541              545                 550              555
Val Lys Ala Pro Asp Thr His Gly Asn Met Trp Val Pro Ser
556              560                 565              569
```

FIGURE 2 (CONT.)

SEQ ID NO 9

```
aag cca aag tat aac tct gga gcc ctc cac atc aag gat att tta        45
Lys Pro Lys Tyr Asn Ser Gly Ala Leu His Ile Lys Asp Ile Leu
 1           5                   10                  15
tct cct tta ttt ggg acg ctt gtt tct tca gct cag ttt aac tac        90
Ser Pro Leu Phe Gly Thr Leu Val Ser Ser Ala Gln Phe Asn Tyr
                 16                  20                  25       30
tgc ttt gac gtg gac tgg ctc gta aaa cag tat cca cca gaa ttc       135
Cys Phe Asp Val Asp Trp Leu Val Lys Gln Tyr Pro Pro Glu Phe
 31              35                  40                  45
cgt aag aag cca atc ctg ctt gtg cat ggt gat aag cga gag gct       180
Arg Lys Lys Pro Ile Leu Leu Val His Gly Asp Lys Arg Glu Ala
 46              50                  55                  60
aag gct cac ctc cat gcc cag gcc aag cct tac gag aac atc tct       225
Lys Ala His Leu His Ala Gln Ala Lys Pro Tyr Glu Asn Ile Ser
 61              65                  70                  75
ctc tgc cag gca aag ttg gat att gcg ttt gga aca cac cac acg       270
Leu Cys Gln Ala Lys Leu Asp Ile Ala Phe Gly Thr His His Thr
 76              80                  85                  90
aaa atg atg ctg ctg ctc tat gaa gaa ggc ctc cgg gtt gtc ata       315
Lys Met Met Leu Leu Leu Tyr Glu Glu Gly Leu Arg Val Val Ile
 91              95                 100                 105
cac acc tcc aac ctc atc cat gct gac tgg cac cag aaa act caa       360
His Thr Ser Asn Leu Ile His Ala Asp Trp His Gln Lys Thr Gln
106             110                 115                 120
gga ata tgg ttg agc ccc tta tac cca cga att gct gat gga acc       405
Gly Ile Trp Leu Ser Pro Leu Tyr Pro Arg Ile Ala Asp Gly Thr
121             125                 130                 135
cac aaa tct gga gag tcg cca aca cat ttt aaa gct gat ctc atc       450
His Lys Ser Gly Glu Ser Pro THr His Phe Lys Ala Asp Leu Ile
136             140                 145                 150
agt tac ttg atg gct tat aat gcc cct tct ctc aag gag tgg ata       495
Ser Tyr Leu Met Ala Tyr Asn Ala Pro Ser Leu Lys Glu Trp Ile
151             155                 160                 165
gat gtc att cac aag cac gat ctc tct gaa aca aat gtt tat ctt       540
Asp Val Ile His Lys His Asp Leu Ser Glu Thr Asn Val Tyr Leu
166             170                 175                 180
att ggt tca acc cca gga cgc ttt caa gga agt caa aaa gat aat       585
Ile Gly Ser Thr Pro Gly Arg Phe Gln Gly Ser Gln Lys Asp Asn
181             185                 190                 195
tgg gga cat ttt aga ctt aag aag ctt ctg aaa gac cat gcc tca       630
Trp Gly His Phe Arg Leu Lys Lys Leu Leu Lys Asp His Ala Ser
196             200                 205                 210
tcc atg cct aac cca gag tcc tgg cct gtc gta ggt cag ttt tca       675
Ser Met Pro Asn Pro Glu Ser Trp Pto Val Val Gly Gln Phe Ser
211             215                 220                 225
agc gtt ggc tcc ttg gga gcc gat gaa tca aag tgg tta tgt tct       720
Ser Val Gly Ser Leu Gly Ala Asp Glu Ser Lys Trp Leu Cys Ser
```

FIGURE 2 (CONT.)

```
226                     230                     235                     240
gag ttt aaa gag agc atg ctg aca ctg ggg aag gaa agc aag act            765
Glu Phe Lys Glu Ser Met Leu Thr Leu Gly Lys Glu Ser Lys Thr
241                     245                     250                     255
cca gga aaa agc tct gtt cct ctt tac ttg atc tat cct tct gtg            810
Pro Gly Lys Ser Ser Val Pro Leu Tyr Leu Ile Tyr Pro Ser Val
256                     260                     265                     270
gaa aat gtg cgg acc agt tta gaa gga tat cct gct ggg ggc tct            855
Glu Asn Val Arg Thr Ser Leu Glu Gly Tyr Pro Ala Gly Gly Ser
271                     275                     280                     285
ctt ccc tat agc atc cag aca gct gaa aaa cag aat tgg ctg cat            900
Leu Pro Tyr Ser Ile Gln Thr Ala Glu Lys Gln Asn Trp Leu His
286                     290                     295                     300
tcc tat ttt cac aaa tgg tca gct gag act tct ggc cgc agc aat            945
Ser Tyr Phe His Lys Trp Ser Ala Glu Thr Ser Gly Arg Ser Asn
301                     305                     310                     315
gcc atg cca cat att aag aca tat atg agg cct tct cca gac ttc            990
Ala Met Pro His Ile Lys Thr Tyr Met Arg Pro Ser Pro Asp Phe
316                     320                     325                     330
agt aaa att gct tgg ttc ctt gtc aca agc gca aat ctg tcc aag           1035
Ser Lys Ile Ala Trp Phe Leu Val Thr Ser Ala Asn Leu Ser Lys
331                     335                     340                     345
gct gcc tgg gga gca ttg gag aag aat ggc acc cag ctg atg atc           1080
Ala Ala Trp Gly Ala Leu Glu Lys Asn Gly Thr Gln Leu Met Ile
346                     350                     355                     360
cgc tcc tac gag ctc ggg gtc ctt ttt ctc cct tca gca ttt ggt           1125
Arg Ser Tyr Glu Leu Gly Val Leu Phe Leu Pro Ser Ala Phe Gly
361                     365                     370                     375
cta gac agt ttc aaa gtg aaa cag aag ttc ttc gct ggc agc cag           1170
Leu Asp Ser Phe Lys Val Lys Gln Lys Phe Phe Ala Gly Ser Gln
376                     380                     385                     390
gag cca atg gcc acc ttt cct gtg cca tat gat ttg cct cca gaa           1215
Glu Pro Met Ala Thr Phe Pro Val Pro Tyr Asp Leu Pro Pro Glu
391                     395                     400                     405
ctg tat gga agt aaa gat cgg cca tgg ata tgg aac att cct tat           1260
Leu Tyr Gly Ser Lys Asp Arg Pro Trp Ile Trp Asn Ile Pro Tyr
406                     410                     415                     420
gtc aaa gca ccg gat acg cat ggg aac atg tgg gtg ccc tcc               1305
Val Lys Ala Pro Asp Thr His Gly Asn Met Trp Val Pro Ser
421                     425                     430                     434
```

FIGURE 2 (CONT.)

SEQ ID NO 10

```
Lys Pro Lys Tyr Asn Ser Gly Ala Leu His Ile Lys Asp Ile Leu
1               5                   10                  15
Ser Pro Leu Phe Gly Thr Leu Val Ser Ser Ala Gln Phe Asn Tyr
16              20                  25                  30
Cys Phe Asp Val Asp Trp Leu Val Lys Gln Tyr Pro Pro Glu Phe
31              35                  40                  45
Arg Lys Lys Pro Ile Leu Leu Val His Gly Asp Lys Arg Glu Ala
46              50                  55                  60
Lys Ala His Leu His Ala Gln Ala Lys Pro Tyr Glu Asn Ile Ser
61              65                  70                  75
Leu Cys Gln Ala Lys Leu Asp Ile Ala Phe Gly Thr His His Thr
76              80                  85                  90
Lys Met Met Leu Leu Leu Tyr Hlu Glu Gly Leu Arg Val Val Ile
91              95                  100                 105
His Thr Ser Asn Leu Ile His Ala Asp Trp His Gln Lys Thr Gln
106             110                 115                 120
Gly Ile Trp Leu Ser Pro Leu Tyr Pro Arg Ile Ala Asp Gly Thr
121             125                 130                 135
His Lys Ser Gly Glu Ser Pro THr His Phe Lys Ala Asp Leu Ile
136             140                 145                 150
Ser Tyr Leu Met Ala Tyr Asn Ala Pro Ser Leu Lys Glu Trp Ile
151             155                 160                 165
Asp Val Ile His Lys His Asp Leu Ser Glu Thr Asn Val Tyr Leu
166             170                 175                 180
Ile Gly Ser Thr Pro Gly Arg Phe Gln Gly Ser Gln Lys Asp Asn
181             185                 190                 195
Trp Gly His Phe Arg Leu Lys Lys Leu Leu Lys Asp His Ala Ser
196             200                 205                 210
Ser Met Pro Asn Pro Glu Ser Trp Pro Val Val Gly Gln Phe Ser
211             215                 220                 225
Ser Val Gly Ser Leu Gly Ala Asp Glu Ser Lys Trp Leu Cys Ser
226             230                 235                 240
Glu Phe Lys Glu Ser Met Leu Thr Leu Gly Lys Glu Ser Lys Thr
241             245                 250                 255
Pro Gly Lys Ser Ser Val Pro Leu Tyr Leu Ile Tyr Pro Ser Val
256             260                 265                 270
Glu Asn Val Arg Thr Ser Leu Glu Gly Tyr Pro Ala Gly Gly Ser
271             275                 280                 285
Leu Pro Tyr Ser Ile Gln Thr Ala Glu Lys Gln Asn Trp Leu His
286             290                 295                 300
Ser Tyr Phe His Lys Trp Ser Ala Glu Thr Ser Gly Arg Ser Asn
301             305                 310                 315
Ala Met Pro His Ile Lys Thr Tyr Met Arg Pro Ser Pro Asp Phe
316             320                 325                 330
Ser Lys Ile Ala Trp Phe Leu Val Thr Ser Ala Asn Leu Ser Lys
331             335                 340                 345
Ala Ala Trp Gly Ala Leu Glu Lys Asn Gly Thr Gln Leu Met Ile
346             350                 355                 360
Arg Ser Tyr Glu Leu Gly Val Leu Phe Leu Pro Ser Ala Phe Gly
361             365                 370                 375
Leu Asp Ser Phe Lys Val Lys Gln Lys Phe Phe Ala Gly Ser Gln
376             380                 385                 390
Glu Pro Met Ala Thr Phe Pro Val Pro Tyr Asp Leu Pro Pro Glu
391             395                 400                 405
Leu Tyr Gly Ser Lys Asp Arg Pro Trp Ile Trp Asn Ile Pro Tyr
406             410                 415                 420
Val Lys Ala Pro Asp Thr His Gly Asn Met Trp Val Pro Ser
421             425                 430             434
```

FIGURE 2 (CONT.)

SEQ ID NO 11

```
gca gca aat gag ccc agg tac acc tgt tcc gag gcc cag aaa gct    45
Ala Ala Asn Glu Pro Arg Tyr Thr Cys Ser Glu Ala Gln Lys Ala
 1               5                  10                  15
gca cac aag agg aaa ata tca cct gtg aaa ttc agc aat aca gat    90
Ala His Lys Arg Lys Ile Ser Pro Val Lys Phe Ser Asn Thr Asp
16              20                  25                  30
tca gtt tta cct ccc aaa agg cag aaa agc ggt tcc cag gag gac   135
Ser Val Leu Pro Pro Lys Arg Gln Lys Ser Gly Ser Gln Glu Asp
31              35                  40                  45
ctc ggc tgg tgt ctg tcc agc agt gat gat gag ctg caa cca gaa   180
Leu Gly Trp Cys Leu Ser Ser Ser Asp Asp Glu Leu Gln Pro Glu
46              50                  55                  60
atg ccg cag aag cag gct gag aaa gtg gtg atc aaa aag gag aaa   225
Met Pro Gln Lys Gln Ala Glu Lys Val Val Ile Lys Lys Glu Lys
61              65                  70                  75
gac atc tct gct ccc aat gac ggc act gcc caa agt act gaa aat   270
Asp Ile Ser Ala Pro Asn Asp Gly Thr Ala Gln Ser Thr Glu Asn
76              80                  85                  90
cat ggg gct ccc gcc tgc cac agg ctc aaa gag gag gaa gac gag   315
His Gly Ala Pro Ala Cys His Arg Leu Lys Glu Glu Glu Asp Glu
91              95                  100                 105
tat gag aca tca ggg gag ggc cag gac att tgg gac atg ctg gat   360
Tyr Glu Thr Ser Gly Glu Gly Gln Asp Ile Trp Asp Met Leu Asp
106             110                 115                 120
aaa agg aac ccc ttc cag ttt tac ctc act aga gtc tct gga gtt   405
Lys Arg Asn Pro Phe Gln Phe Tyr Leu Thr Arg Val Ser Gly Val
121             125                 130                 135
aag cca aag tat aac tct gga gcc ctc cac atc aag gat att tta   450
Lys Pro Lys Tyr Asn Ser Gly Ala Leu His Ile Lys Asp Ile Leu
136             140                 145                 150
tct cct tta ttt ggg acg ctt gtt tct tca gct cag ttt aac tac   495
Ser Pro Leu Phe Gly Thr Leu Val Ser Ser Ala Gln Phe Asn Tyr
151             155                 160                 165
tgc ttt gac gtg gac tgg ctc gta aaa cag tat cca cca gaa ttc   540
Cys Phe Asp Val Asp Trp Leu Val Lys Gln Tyr Pro Pro Glu Phe
166             170                 175                 180
cgt aag aag cca atc ctg ctt gtg cat ggt gat aag cga gag gct   585
Arg Lys Lys Pro Ile Leu Leu Val His Gly Asp Lys Arg Glu Ala
181             185                 190                 195
aag gct cac ctc cat gcc cag gcc aag cct tac gag aac atc tct   630
Lys Ala His Leu His Ala Gln Ala Lys Pro Tyr Glu Asn Ile Ser
196             200                 205                 210
ctc tgc cag gca aag ttg gat att gcg ttt gga aca cac cac acg   675
Leu Cys Gln Ala Lys Leu Asp Ile Ala Phe Gly Thr His His Thr
211             215                 220                 225
aaa atg atg ctg ctc tat gaa gaa ggc ctc cgg gtt gtc ata       720
Lys Met Met Leu Leu Leu Tyr Hlu Glu Gly Leu Arg Val Val Ile
226             230                 235                 240
cac acc tcc aac ctc atc cat gct gac tgg cac cag aaa act caa   765
His Thr Ser Asn Leu Ile His Ala Asp Trp His Gln Lys Thr Gln
241             245                 250                 255
gga ata tgg ttg agc ccc tta tac cca cga att gct gat gga acc   810
Gly Ile Trp Leu Ser Pro Leu Tyr Pro Arg Ile Ala Asp Gly Thr
256             260                 265                 270
cac aaa tct gga gag tcg cca aca cat ttt aaa gct gat ctc atc   855
His Lys Ser Gly Glu Ser Pro THr His Phe Lys Ala Asp Leu Ile
271             275                 280                 285
```

FIGURE 2 (CONT.)

```
agt tac ttg atg gct tat aat gcc cct tct ctc aag gag tgg ata      900
Ser Tyr Leu Met Ala Tyr Asn Ala Pro Ser Leu Lys Glu Trp Ile
286             290             295             300
gat gtc att cac aag cac gat ctc tct gaa aca aat gtt tat ctt      945
Asp Val Ile His Lys His Asp Leu Ser Glu Thr Asn Val Tyr Leu
301             305             310             315
att ggt tca acc cca gga cgc ttt caa gga agt caa aaa gat aat      990
Ile Gly Ser Thr Pro Gly Arg Phe Gln Gly Ser Gln Lys Asp Asn
316             320             325             330
tgg gga cat ttt aga ctt aag aag ctt ctg aaa gac cat gcc tca     1035
Trp Gly His Phe Arg Leu Lys Lys Leu Leu Lys Asp His Ala Ser
331             335             340             345
tcc atg cct aac cca gag tcc tgg cct gta ggt cag ttt tca         1080
Ser Met Pro Asn Pro Glu Ser Trp Pro Val Val Gly Gln Phe Ser
346             350         -       355             360
agc gtt ggc tcc ttg gga gcc gat gaa tca aag tgg tta tgt tct     1125
Ser Val Gly Ser Leu Gly Ala Asp Glu Ser Lys Trp Leu Cys Ser
361             365             370             375
gag ttt aaa gag agc atg ctg aca ctg ggg aag gaa agc aag act     1170
Glu Phe Lys Glu Ser Met Leu Thr Leu Gly Lys Glu Ser Lys Thr
376             380             385             390
cca gga aaa agc tct gtt cct ctt tac ttg atc tat cct tct gtg     1215
Pro Gly Lys Ser Ser Val Pro Leu Tyr Leu Ile Tyr Pro Ser Val
391             395             400             405
gaa aat gtg cgg acc agt tta gaa gga tat cct gct ggg ggc tct     1260
Glu Asn Val Arg Thr Ser Leu Glu Gly Tyr Pro Ala Gly Gly Ser
406             410             415             420
ctt ccc tat agc atc cag aca gct gaa aaa cag aat tgg ctg cat     1305
Leu Pro Tyr Ser Ile Gln Thr Ala Glu Lys Gln Asn Trp Leu His
421             425             430             435
tcc tat ttt cac aaa tgg tca gct gag act tct ggc cgc agc aat     1350
Ser Tyr Phe His Lys Trp Ser Ala Glu Thr Ser Gly Arg Ser Asn
436             440             445             450
gcc atg cca cat att aag aca tat atg agg cct tct cca gac ttc     1395
Ala Met Pro His Ile Lys Thr Tyr Met Arg Pro Ser Pro Asp Phe
451             455             460             465
agt aaa att gct tgg ttc ctt gtc aca agc gca aat ctg tcc aag     1440
Ser Lys Ile Ala Trp Phe Leu Val Thr Ser Ala Asn Leu Ser Lys
466             470             475             480
gct gcc tgg gga gca ttg gag aag aat ggc acc cag ctg atg atc     1485
Ala Ala Trp Gly Ala Leu Glu Lys Asn Gly Thr Gln Leu Met Ile
481             485             490             495
cgc tcc tac gag ctc ggg gtc ctt ttt ctc cct tca                 1521
Arg Ser Tyr Glu Leu Gly Val Leu Phe Leu Pro Ser
496             500             505     507
```

FIGURE 2 (CONT.)

SEQ ID NO 12

```
Ala Ala Asn Glu Pro Arg Tyr Thr Cys Ser Glu Ala Gln Lys Ala
1               5                   10                  15
Ala His Lys Arg Lys Ile Ser Pro Val Lys Phe Ser Asn Thr Asp
16              20                  25                  30
Ser Val Leu Pro Pro Lys Arg Gln Lys Ser Gly Ser Gln Glu Asp
31              35                  40                  45
Leu Gly Trp Cys Leu Ser Ser Ser Asp Asp Glu Leu Gln Pro Glu
46              50                  55                  60
Met Pro Gln Lys Gln Ala Glu Lys Val Val Ile Lys Lys Glu Lys
61              65                  70                  75
Asp Ile Ser Ala Pro Asn Asp Gly Thr Ala Gln Ser Thr Glu Asn
76              80                  85                  90
His Gly Ala Pro Ala Cys His Arg Leu Lys Glu Glu Glu Asp Glu
91              95                  100                 105
Tyr Glu Thr Ser Gly Glu Gly Gln Asp Ile Trp Asp Met Leu Asp
106             110                 115                 120
Lys Arg Asn Pro Phe Gln Phe Tyr Leu Thr Arg Val Ser Gly Val
121             125                 130                 135
Lys Pro Lys Tyr Asn Ser Gly Ala Leu His Ile Lys Asp Ile Leu
136             140                 145                 150
Ser Pro Leu Phe Gly Thr Leu Val Ser Ser Ala Gln Phe Asn Tyr
151             155                 160                 165
Cys Phe Asp Val Asp Trp Leu Val Lys Gln Tyr Pro Pro Glu Phe
166             170                 175                 180
Arg Lys Lys Pro Ile Leu Leu Val His Gly Asp Lys Arg Glu Ala
181             185                 190                 195
Lys Ala His Leu His Ala Gln Ala Lys Pro Tyr Glu Asn Ile Ser
196             200                 205                 210
Leu Cys Gln Ala Lys Leu Asp Ile Ala Phe Gly Thr His His Thr
211             215                 220                 225
Lys Met Met Leu Leu Leu Tyr Hlu Glu Gly Leu Arg Val Val Ile
226             230                 235                 240
His Thr Ser Asn Leu Ile His Ala Asp Trp His Gln Lys Thr Gln
241             245                 250                 255
Gly Ile Trp Leu Ser Pro Leu Tyr Pro Arg Ile Ala Asp Gly Thr
256             260                 265                 270
His Lys Ser Gly Glu Ser Pro THr His Phe Lys Ala Asp Leu Ile
271             275                 280                 285
Ser Tyr Leu Met Ala Tyr Asn Ala Pro Ser Leu Lys Glu Trp Ile
286             290                 295                 300
Asp Val Ile His Lys His Asp Leu Ser Glu Thr Asn Val Tyr Leu
301             305                 310                 315
Ile Gly Ser Thr Pro Gly Arg Phe Gln Gly Ser Gln Lys Asp Asn
316             320                 325                 330
Trp Gly His Phe Arg Leu Lys Lys Leu Leu Lys Asp His Ala Ser
331             335                 340                 345
Ser Met Pro Asn Pro Glu Ser Trp Pto Val Val Gly Gln Phe Ser
346             350                 355                 360
Ser Val Gly Ser Leu Gly Ala Asp Glu Ser Lys Trp Leu Cys Ser
361             365                 370                 375
Glu Phe Lys Glu Ser Met Leu Thr Leu Gly Lys Glu Ser Lys Thr
376             380                 385                 390
Pro Gly Lys Ser Ser Val Pro Leu Tyr Leu Ile Tyr Pro Ser Val
391             395                 400                 405
```

FIGURE 2 (CONT.)

```
Glu Asn Val Arg Thr Ser Leu Glu Gly Tyr Pro Ala Gly Gly Ser
406             410                 415                 420
Leu Pro Tyr Ser Ile Gln Thr Ala Glu Lys Gln Asn Trp Leu His
421             425                 430                 435
Ser Tyr Phe His Lys Trp Ser Ala Glu Thr Ser Gly Arg Ser Asn
436             440                 445                 450
Ala Met Pro His Ile Lys Thr Tyr Met Arg Pro Ser Pro Asp Phe
451             455                 460                 465
Ser Lys Ile Ala Trp Phe Leu Val Thr Ser Ala Asn Leu Ser Lys
466             470                 475                 480
Ala Ala Trp Gly Ala Leu Glu Lys Asn Gly Thr Gln Leu Met Ile
481             485                 490                 495
Arg Ser Tyr Glu Leu Gly Val Leu Phe Leu Pro Ser
496             500                 505     507
```

SEQ ID NO 13

```
aag cca aag tat aac tct gga gcc ctc cac atc aag gat att tta    45
Lys Pro Lys Tyr Asn Ser Gly Ala Leu His Ile Lys Asp Ile Leu
1               5                   10                  15
tct cct tta ttt ggg acg ctt gtt tct tca gct cag ttt aac tac    90
Ser Pro Leu Phe Gly Thr Leu Val Ser Ser Ala Gln Phe Asn Tyr
                16                  20                  25      30
tgc ttt gac gtg gac tgg ctc gta aaa cag tat cca cca gaa ttc    135
Cys Phe Asp Val Asp Trp Leu Val Lys Gln Tyr Pro Pro Glu Phe
31              35                  40                  45
cgt aag aag cca atc ctg ctt gtg cat ggt gat aag cga gag gct    180
Arg Lys Lys Pro Ile Leu Leu Val His Gly Asp Lys Arg Glu Ala
46              50                  55                  60
aag gct cac ctc cat gcc cag gcc aag cct tac gag aac atc tct    225
Lys Ala His Leu His Ala Gln Ala Lys Pro Tyr Glu Asn Ile Ser
61              65                  70                  75
ctc tgc cag gca aag ttg gat att gcg ttt gga aca cac cac acg    270
Leu Cys Gln Ala Lys Leu Asp Ile Ala Phe Gly Thr His His Thr
76              80                  85                  90
aaa atg atg ctg ctg ctc tat gaa gaa ggc ctc cgg gtt gtc ata    315
Lys Met Met Leu Leu Leu Tyr Glu Glu Gly Leu Arg Val Val Ile
91              95                  100                 105
cac acc tcc aac ctc atc cat gct gac tgg cac cag aaa act caa    360
His Thr Ser Asn Leu Ile His Ala Asp Trp His Gln Lys Thr Gln
106             110                 115                 120
gga ata tgg ttg agc ccc tta tac cca cga att gct gat gga acc    405
Gly Ile Trp Leu Ser Pro Leu Tyr Pro Arg Ile Ala Asp Gly Thr
121             125                 130                 135
cac aaa tct gga gag tcg cca aca cat ttt aaa gct gat ctc atc    450
His Lys Ser Gly Glu Ser Pro Thr His Phe Lys Ala Asp Leu Ile
136             140                 145                 150
agt tac ttg atg gct tat aat gcc cct tct ctc aag gag tgg ata    495
Ser Tyr Leu Met Ala Tyr Asn Ala Pro Ser Leu Lys Glu Trp Ile
151             155                 160                 165
gat gtc att cac aag cac gat ctc tct gaa aca aat gtt tat ctt    540
Asp Val Ile His Lys His Asp Leu Ser Glu Thr Asn Val Tyr Leu
166             170                 175                 180
```

FIGURE 2 (CONT.)

```
att ggt tca acc cca gga cgc ttt caa gga agt caa aaa gat aat      585
Ile Gly Ser Thr Pro Gly Arg Phe Gln Gly Ser Gln Lys Asp Asn
181             185                 190                 195
tgg gga cat ttt aga ctt aag aag ctt ctg aaa gac cat gcc tca      630
Trp Gly His Phe Arg Leu Lys Lys Leu Leu Lys Asp His Ala Ser
196             200                 205                 210
tcc atg cct aac cca gag tcc tgg cct gtc gta ggt cag ttt tca      675
Ser Met Pro Asn Pro Glu Ser Trp Pro Val Val Gly Gln Phe Ser
211             215                 220                 225
agc gtt ggc tcc ttg gga gcc gat gaa tca aag tgg tta tgt tct      720
Ser Val Gly Ser Leu Gly Ala Asp Glu Ser Lys Trp Leu Cys Ser
226             230                 235                 240
gag ttt aaa gag agc atg ctg aca ctg ggg aag gaa agc aag act      765
Glu Phe Lys Glu Ser Met Leu Thr Leu Gly Lys Glu Ser Lys Thr
241             245                 250                 255
cca gga aaa agc tct gtt cct ctt tac ttg atc tat cct tct gtg      810
Pro Gly Lys Ser Ser Val Pro Leu Tyr Leu Ile Tyr Pro Ser Val
256             260                 265                 270
gaa aat gtg cgg acc agt tta gaa gga tat cct gct ggg ggc tct      855
Glu Asn Val Arg Thr Ser Leu Glu Gly Tyr Pro Ala Gly Gly Ser
271             275                 280                 285
ctt ccc tat agc atc cag aca gct gaa aaa cag aat tgg ctg cat      900
Leu Pro Tyr Ser Ile Gln Thr Ala Glu Lys Gln Asn Trp Leu His
286             290                 295                 300
tcc tat ttt cac aaa tgg tca gct gag act tct ggc cgc agc aat      945
Ser Tyr Phe His Lys Trp Ser Ala Glu Thr Ser Gly Arg Ser Asn
301             305                 310                 315
gcc atg cca cat att aag aca tat atg agg cct tct cca gac ttc      990
Ala Met Pro His Ile Lys Thr Tyr Met Arg Pro Ser Pro Asp Phe
316             320                 325                 330
agt aaa att gct tgg ttc ctt gtc aca agc gca aat ctg tcc aag     1035
Ser Lys Ile Ala Trp Phe Leu Val Thr Ser Ala Asn Leu Ser Lys
331             335                 340                 345
gct gcc tgg gga gca ttg gag aag aat ggc acc cag ctg atg atc     1080
Ala Ala Trp Gly Ala Leu Glu Lys Asn Gly Thr Gln Leu Met Ile
346             350                 355                 360
cgc tcc tac gag ctc ggg gtc ctt ttt ctc cct tca                 1116
Arg Ser Tyr Glu Leu Gly Val Leu Phe Leu Pro Ser
361             365                 370     372
```

FIGURE 2 (CONT.)

SEQ ID NO 14

```
Lys Pro Lys Tyr Asn Ser Gly Ala Leu His Ile Lys Asp Ile Leu
1               5                   10                  15
Ser Pro Leu Phe Gly Thr Leu Val Ser Ser Ala Gln Phe Asn Tyr
16              20                  25                  30
Cys Phe Asp Val Asp Trp Leu Val Lys Gln Tyr Pro Pro Glu Phe
31              35                  40                  45
Arg Lys Lys Pro Ile Leu Leu Val His Gly Asp Lys Arg Glu Ala
46              50                  55                  60
Lys Ala His Leu His Ala Gln Ala Lys Pro Tyr Glu Asn Ile Ser
61              65                  70                  75
Leu Cys Gln Ala Lys Leu Asp Ile Ala Phe Gly Thr His His Thr
76              80                  85                  90
Lys Met Met Leu Leu Leu Tyr Glu Glu Gly Leu Arg Val Val Ile
91              95                  100                 105
His Thr Ser Asn Leu Ile His Ala Asp Trp His Gln Lys Thr Gln
106             110                 115                 120
Gly Ile Trp Leu Ser Pro Leu Tyr Pro Arg Ile Ala Asp Gly Thr
121             125                 130                 135
His Lys Ser Gly Glu Ser Pro THr His Phe Lys Ala Asp Leu Ile
136             140                 145                 150
Ser Tyr Leu Met Ala Tyr Asn Ala Pro Ser Leu Lys Glu Trp Ile
151             155                 160                 165
Asp Val Ile His Lys His Asp Leu Ser Glu Thr Asn Val Tyr Leu
166             170                 175                 180
Ile Gly Ser Thr Pro Gly Arg Phe Gln Gly Ser Gln Lys Asp Asn
181             185                 190                 195
Trp Gly His Phe Arg Leu Lys Lys Leu Leu Lys Asp His Ala Ser
196             200                 205                 210
Ser Met Pro Asn Pro Glu Ser Trp Pro Val Val Gly Gln Phe Ser
211             215                 220                 225
Ser Val Gly Ser Leu Gly Ala Asp Glu Ser Lys Trp Leu Cys Ser
226             230                 235                 240
Glu Phe Lys Glu Ser Met Leu Thr Leu Gly Lys Glu Ser Lys Thr
241             245                 250                 255
Pro Gly Lys Ser Ser Val Pro Leu Tyr Leu Ile Tyr Pro Ser Val
256             260                 265                 270
Glu Asn Val Arg Thr Ser Leu Glu Gly Tyr Pro Ala Gly Gly Ser
271             275                 280                 285
Leu Pro Tyr Ser Ile Gln Thr Ala Glu Lys Gln Asn Trp Leu His
286             290                 295                 300
Ser Tyr Phe His Lys Trp Ser Ala Glu Thr Ser Gly Arg Ser Asn
301             305                 310                 315
Ala Met Pro His Ile Lys Thr Tyr Met Arg Pro Ser Pro Asp Phe
316             320                 325                 330
Ser Lys Ile Ala Trp Phe Leu Val Thr Ser Ala Asn Leu Ser Lys
331             335                 340                 345
Ala Ala Trp Gly Ala Leu Glu Lys Asn Gly Thr Gln Leu Met Ile
346             350                 355                 360
Arg Ser Tyr Glu Leu Gly Val Leu Phe Leu Pro Ser
361             365                 370     372
```

FIGURE 4

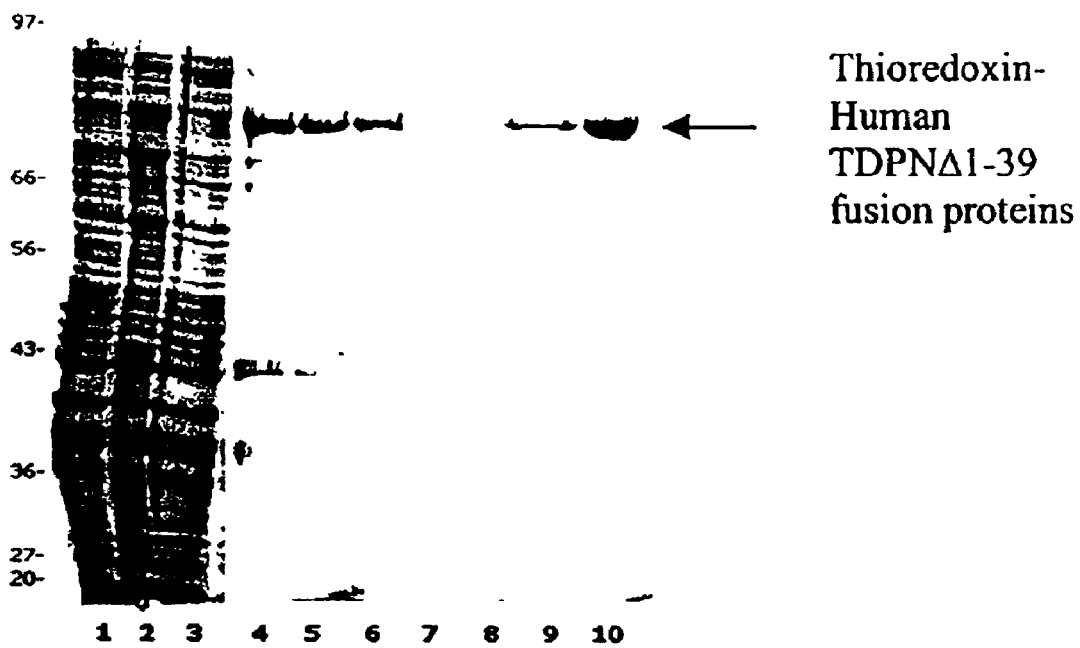

Thioredoxin-Human TDPNΔ1-39 fusion proteins

Lane 1: lysate from un-induced culture
Lane 2: lysate from induced culture
Lane 3: soluble fraction of crude lysate
Lane 4: insoluble fraction of crude lysate.
Lane 5: sample applied onto DEAE
Lane 6: sample from DEAE flow-through
Lane 7: flow-through fraction from Nickel column
Lane 8: washed fraction from Nickel column
Lane 9: eluted fraction from Nickel column
Lane 10: 20 microgram of proteins after concentration
Molecular weight markers are shown on the left

*p*-nitrophenyl thymidine-3'-phosphate free acid $C_{16}H_{18}N_3O_{10}P$

Mol. Wt = 443.30

SEQUENCE LISTING

```
<160> NUMBER OF SEQ ID NOS: 20
<210> SEQ ID NO 1
<211> LENGTH: 1824
<212> TYPE: DNA
<213> ORGANISM: Homo sapiens
<220> FEATURE:
<221> NAME/KEY: CDS
<222> LOCATION: (1)..(1824)

<400> SEQUENCE: 1 atg tct cag gaa ggc gat tat ggg agg tgg acc ata tct agt agt gat      48
Met Ser Gln Glu Gly Asp Tyr Gly Arg Trp Thr Ile Ser Ser Ser Asp
1               5                   10                  15 gaa agt gag gaa gaa aag cca aaa cca gac aag cca tct acc tct tct      96
Glu Ser Glu Glu Glu Lys Pro Lys Pro Asp Lys Pro Ser Thr Ser Ser
            20                  25                  30 ctt ctc tgt gcc agg caa gga gca gca aat gag ccc agg tac acc tgt     144
Leu Leu Cys Ala Arg Gln Gly Ala Ala Asn Glu Pro Arg Tyr Thr Cys
        35                  40                  45 tcc gag gcc cag aaa gct gca cac aag agg aaa ata tca cct gtg aaa     192
Ser Glu Ala Gln Lys Ala Ala His Lys Arg Lys Ile Ser Pro Val Lys
    50                  55                  60 ttc agc aat aca gat tca gtt tta cct ccc aaa agg cag aaa agc ggt     240
Phe Ser Asn Thr Asp Ser Val Leu Pro Pro Lys Arg Gln Lys Ser Gly
65                  70                  75                  80 tcc cag gag gac ctc ggc tgg tgt ctg tcc agc agt gat gat gag ctg     288
Ser Gln Glu Asp Leu Gly Trp Cys Leu Ser Ser Ser Asp Asp Glu Leu
                85                  90                  95 caa cca gaa atg ccg cag aag cag gct gag aaa gtg gtg atc aaa aag     336
Gln Pro Glu Met Pro Gln Lys Gln Ala Glu Lys Val Val Ile Lys Lys
            100                 105                 110 gag aaa gac atc tct gct ccc aat gac ggc act gcc caa agt act gaa     384
Glu Lys Asp Ile Ser Ala Pro Asn Asp Gly Thr Ala Gln Ser Thr Glu
        115                 120                 125 aat cat ggg gct ccc gcc tgc cac agg ctc aaa gag gag gaa gac gag     432
Asn His Gly Ala Pro Ala Cys His Arg Leu Lys Glu Glu Glu Asp Glu
    130                 135                 140 tat gag aca tca ggg gag ggc cag gac att tgg gac atg ctg gat aaa     480
Tyr Glu Thr Ser Gly Glu Gly Gln Asp Ile Trp Asp Met Leu Asp Lys
145                 150                 155                 160 agg aac ccc ttc cag ttt tac ctc act aga gtc tct gga gtt aag cca     528
```

```
                Arg Asn Pro Phe Gln Phe Tyr Leu Thr Arg Val Ser Gly Val Lys Pro
                                165                 170                 175 aag tat aac tct gga gcc ctc cac atc aag gat att tta tct cct tta          576
Lys Tyr Asn Ser Gly Ala Leu His Ile Lys Asp Ile Leu Ser Pro Leu
            180                 185                 190 ttt ggg acg ctt gtt tct tca gct cag ttt aac tac tgc ttt gac gtg          624
Phe Gly Thr Leu Val Ser Ser Ala Gln Phe Asn Tyr Cys Phe Asp Val
            195                 200                 205 gac tgg ctc gta aaa cag tat cca cca gaa ttc cgt aag aag cca atc          672
Asp Trp Leu Val Lys Gln Tyr Pro Pro Glu Phe Arg Lys Lys Pro Ile
        210                 215                 220 ctg ctt gtg cat ggt gat aag cga gag gct aag gct cac ctc cat gcc          720
Leu Leu Val His Gly Asp Lys Arg Glu Ala Lys Ala His Leu His Ala
225                 230                 235                 240 cag gcc aag cct tac gag aac atc tct ctc tgc cag gca aag ttg gat          768
Gln Ala Lys Pro Tyr Glu Asn Ile Ser Leu Cys Gln Ala Lys Leu Asp
                245                 250                 255 att gcg ttt gga aca cac cac acg aaa atg atg ctg ctc tat gaa              816
Ile Ala Phe Gly Thr His His Thr Lys Met Met Leu Leu Tyr Glu
            260                 265                 270 gaa ggc ctc cgg gtt gtc ata cac acc tcc aac ctc atc cat gct gac          864
Glu Gly Leu Arg Val Val Ile His Thr Ser Asn Leu Ile His Ala Asp
            275                 280                 285 tgg cac cag aaa act caa gga ata tgg ttg agc ccc tta tac cca cga          912
Trp His Gln Lys Thr Gln Gly Ile Trp Leu Ser Pro Leu Tyr Pro Arg
        290                 295                 300 att gct gat gga acc cac aaa tct gga gag tcg cca aca cat ttt aaa          960
Ile Ala Asp Gly Thr His Lys Ser Gly Glu Ser Pro Thr His Phe Lys
305                 310                 315                 320 gct gat ctc atc agt tac ttg atg gct tat aat gcc cct tct ctc aag         1008
Ala Asp Leu Ile Ser Tyr Leu Met Ala Tyr Asn Ala Pro Ser Leu Lys
                325                 330                 335 gag tgg ata gat gtc att cac aag cac gat ctc tct gaa aca aat gtt         1056
Glu Trp Ile Asp Val Ile His Lys His Asp Leu Ser Glu Thr Asn Val
            340                 345                 350 tat ctt att ggt tca acc cca gga cgc ttt caa gga agt caa aaa gat         1104
Tyr Leu Ile Gly Ser Thr Pro Gly Arg Phe Gln Gly Ser Gln Lys Asp
            355                 360                 365 aat tgg gga cat ttt aga ctt aag aag ctt ctg aaa gac cat gcc tca         1152
Asn Trp Gly His Phe Arg Leu Lys Lys Leu Leu Lys Asp His Ala Ser
        370                 375                 380 tcc atg cct aac cca gag tcc tgg cct gtc gta ggt cag ttt tca agc         1200
Ser Met Pro Asn Pro Glu Ser Trp Pro Val Val Gly Gln Phe Ser Ser
385                 390                 395                 400 gtt ggc tcc ttg gga gcc gat gaa tca aag tgg tta tgt tct gag ttt         1248
Val Gly Ser Leu Gly Ala Asp Glu Ser Lys Trp Leu Cys Ser Glu Phe
                405                 410                 415 aaa gag agc atg ctg aca ctg ggg aag gaa agc aag act cca gga aaa         1296
Lys Glu Ser Met Leu Thr Leu Gly Lys Glu Ser Lys Thr Pro Gly Lys
            420                 425                 430 agc tct gtt cct ctt tac ttg atc tat cct tct gtg gaa aat gtg cgg         1344
Ser Ser Val Pro Leu Tyr Leu Ile Tyr Pro Ser Val Glu Asn Val Arg
            435                 440                 445 acc agt tta gaa gga tat cct gct ggg ggc tct ctt ccc tat agc atc         1392
Thr Ser Leu Glu Gly Tyr Pro Ala Gly Gly Ser Leu Pro Tyr Ser Ile
        450                 455                 460 cag aca gct gaa aaa cag aat tgg ctg cat tcc tat ttt cac aaa tgg         1440
Gln Thr Ala Glu Lys Gln Asn Trp Leu His Ser Tyr Phe His Lys Trp
465                 470                 475                 480
```

-continued

```
tca gct gag act tct ggc cgc agc aat gcc atg cca cat att aag aca   1488
Ser Ala Glu Thr Ser Gly Arg Ser Asn Ala Met Pro His Ile Lys Thr
            485                 490                 495 tat atg agg cct tct cca gac ttc agt aaa att gct tgg ttc ctt gtc   1536
Tyr Met Arg Pro Ser Pro Asp Phe Ser Lys Ile Ala Trp Phe Leu Val
            500                 505                 510 aca agc gca aat ctg tcc aag gct gcc tgg gga gca ttg gag aag aat   1584
Thr Ser Ala Asn Leu Ser Lys Ala Ala Trp Gly Ala Leu Glu Lys Asn
            515                 520                 525 ggc acc cag ctg atg atc cgc tcc tac gag ctc ggg gtc ctt ttt ctc   1632
Gly Thr Gln Leu Met Ile Arg Ser Tyr Glu Leu Gly Val Leu Phe Leu
        530                 535                 540 cct tca gca ttt ggt cta gac agt ttc aaa gtg aaa cag aag ttc ttc   1680
Pro Ser Ala Phe Gly Leu Asp Ser Phe Lys Val Lys Gln Lys Phe Phe
545                 550                 555                 560 gct ggc agc cag gag cca atg gcc acc ttt cct gtg cca tat gat ttg   1728
Ala Gly Ser Gln Glu Pro Met Ala Thr Phe Pro Val Pro Tyr Asp Leu
                565                 570                 575 cct cca gaa ctg tat gga agt aaa gat cgg cca tgg ata tgg aac att   1776
Pro Pro Glu Leu Tyr Gly Ser Lys Asp Arg Pro Trp Ile Trp Asn Ile
            580                 585                 590 cct tat gtc aaa gca ccg gat acg cat ggg aac atg tgg gtg ccc tcc   1824
Pro Tyr Val Lys Ala Pro Asp Thr His Gly Asn Met Trp Val Pro Ser
            595                 600                 605
```

<210> SEQ ID NO 2
<211> LENGTH: 608
<212> TYPE: PRT
<213> ORGANISM: Homo sapiens

<400> SEQUENCE: 2

```
Met Ser Gln Glu Gly Asp Tyr Gly Arg Trp Thr Ile Ser Ser Ser Asp
1               5                   10                  15

Glu Ser Glu Glu Glu Lys Pro Lys Pro Asp Lys Pro Ser Thr Ser Ser
            20                  25                  30

Leu Leu Cys Ala Arg Gln Gly Ala Ala Asn Glu Pro Arg Tyr Thr Cys
        35                  40                  45

Ser Glu Ala Gln Lys Ala Ala His Lys Arg Lys Ile Ser Pro Val Lys
    50                  55                  60

Phe Ser Asn Thr Asp Ser Val Leu Pro Pro Lys Arg Gln Lys Ser Gly
65                  70                  75                  80

Ser Gln Glu Asp Leu Gly Trp Cys Leu Ser Ser Ser Asp Asp Glu Leu
                85                  90                  95

Gln Pro Glu Met Pro Gln Lys Gln Ala Glu Lys Val Val Ile Lys Lys
            100                 105                 110

Glu Lys Asp Ile Ser Ala Pro Asn Asp Gly Thr Ala Gln Ser Thr Glu
        115                 120                 125

Asn His Gly Ala Pro Ala Cys His Arg Leu Lys Glu Glu Glu Asp Glu
    130                 135                 140

Tyr Glu Thr Ser Gly Glu Gly Gln Asp Ile Trp Asp Met Leu Asp Lys
145                 150                 155                 160

Arg Asn Pro Phe Gln Phe Tyr Leu Thr Arg Val Ser Gly Val Lys Pro
                165                 170                 175

Lys Tyr Asn Ser Gly Ala Leu His Ile Lys Asp Ile Leu Ser Pro Leu
            180                 185                 190

Phe Gly Thr Leu Val Ser Ser Ala Gln Phe Asn Tyr Cys Phe Asp Val
        195                 200                 205
```

-continued

```
Asp Trp Leu Val Lys Gln Tyr Pro Pro Glu Phe Arg Lys Lys Pro Ile
210                 215                 220
Leu Leu Val His Gly Asp Lys Arg Glu Ala Lys Ala His Leu His Ala
225                 230                 235                 240
Gln Ala Lys Pro Tyr Glu Asn Ile Ser Leu Cys Gln Ala Lys Leu Asp
                245                 250                 255
Ile Ala Phe Gly Thr His His Thr Lys Met Met Leu Leu Leu Tyr Glu
                260                 265                 270
Glu Gly Leu Arg Val Val Ile His Thr Ser Asn Leu Ile His Ala Asp
                275                 280                 285
Trp His Gln Lys Thr Gln Gly Ile Trp Leu Ser Pro Leu Tyr Pro Arg
290                 295                 300
Ile Ala Asp Gly Thr His Lys Ser Gly Glu Ser Pro Thr His Phe Lys
305                 310                 315                 320
Ala Asp Leu Ile Ser Tyr Leu Met Ala Tyr Asn Ala Pro Ser Leu Lys
                325                 330                 335
Glu Trp Ile Asp Val Ile His Lys His Asp Leu Ser Glu Thr Asn Val
                340                 345                 350
Tyr Leu Ile Gly Ser Thr Pro Gly Arg Phe Gln Gly Ser Gln Lys Asp
                355                 360                 365
Asn Trp Gly His Phe Arg Leu Lys Lys Leu Leu Lys Asp His Ala Ser
370                 375                 380
Ser Met Pro Asn Pro Glu Ser Trp Pro Val Val Gly Gln Phe Ser Ser
385                 390                 395                 400
Val Gly Ser Leu Gly Ala Asp Glu Ser Lys Trp Leu Cys Ser Glu Phe
                405                 410                 415
Lys Glu Ser Met Leu Thr Leu Gly Lys Glu Ser Lys Thr Pro Gly Lys
                420                 425                 430
Ser Ser Val Pro Leu Tyr Leu Ile Tyr Pro Ser Val Glu Asn Val Arg
                435                 440                 445
Thr Ser Leu Glu Gly Tyr Pro Ala Gly Gly Ser Leu Pro Tyr Ser Ile
450                 455                 460
Gln Thr Ala Glu Lys Gln Asn Trp Leu His Ser Tyr Phe His Lys Trp
465                 470                 475                 480
Ser Ala Glu Thr Ser Gly Arg Ser Asn Ala Met Pro His Ile Lys Thr
                485                 490                 495
Tyr Met Arg Pro Ser Pro Asp Phe Ser Lys Ile Ala Trp Phe Leu Val
                500                 505                 510
Thr Ser Ala Asn Leu Ser Lys Ala Ala Trp Gly Ala Leu Glu Lys Asn
                515                 520                 525
Gly Thr Gln Leu Met Ile Arg Ser Tyr Glu Leu Gly Val Leu Phe Leu
530                 535                 540
Pro Ser Ala Phe Gly Leu Asp Ser Phe Lys Val Lys Gln Lys Phe Phe
545                 550                 555                 560
Ala Gly Ser Gln Glu Pro Met Ala Thr Phe Pro Val Pro Tyr Asp Leu
                565                 570                 575
Pro Pro Glu Leu Tyr Gly Ser Lys Asp Arg Pro Trp Ile Trp Asn Ile
                580                 585                 590
Pro Tyr Val Lys Ala Pro Asp Thr His Gly Asn Met Trp Val Pro Ser
                595                 600                 605
```

<210> SEQ ID NO 3
<211> LENGTH: 30
<212> TYPE: DNA

```
-continued

<213> ORGANISM: Artificial Sequence
<220> FEATURE:
<223> OTHER INFORMATION: Synthetic

<400> SEQUENCE: 3
gcagcaaatg agcccaggta cacctgttcc                                  30

<210> SEQ ID NO 4
<211> LENGTH: 25
<212> TYPE: DNA
<213> ORGANISM: Artificial Sequence
<220> FEATURE:
<223> OTHER INFORMATION: Synthetic

<400> SEQUENCE: 4
ggagggcacc cacatgttcc catgc                                       25

<210> SEQ ID NO 5
<211> LENGTH: 31
<212> TYPE: DNA
<213> ORGANISM: Artificial Sequence
<220> FEATURE:
<223> OTHER INFORMATION: Synthetic

<400> SEQUENCE: 5
aagtataact ctcgagccct ccacatcaag g                                31

<210> SEQ ID NO 6
<211> LENGTH: 25
<212> TYPE: DNA
<213> ORGANISM: Artificial Sequence
<220> FEATURE:
<223> OTHER INFORMATION: Synthetic

<400> SEQUENCE: 6
tgaagggagg aaaaggaccc cgagc                                       25

<210> SEQ ID NO 7
<211> LENGTH: 1707
<212> TYPE: DNA
<213> ORGANISM: Homo sapiens
<220> FEATURE:
<221> NAME/KEY: CDS
<222> LOCATION: (1)..(1707)

<400> SEQUENCE: 7 gca gca aat gag ccc agg tac acc tgt tcc gag gcc cag aaa gct gca    48
Ala Ala Asn Glu Pro Arg Tyr Thr Cys Ser Glu Ala Gln Lys Ala Ala
1               5                  10                  15 cac aag agg aaa ata tca cct gtg aaa ttc agc aat aca gat tca gtt    96
His Lys Arg Lys Ile Ser Pro Val Lys Phe Ser Asn Thr Asp Ser Val
            20                  25                  30 tta cct ccc aaa agg cag aaa agc ggt tcc cag gag gac ctc ggc tgg   144
Leu Pro Pro Lys Arg Gln Lys Ser Gly Ser Gln Glu Asp Leu Gly Trp
        35                  40                  45 tgt ctg tcc agc agt gat gat gag ctg caa cca gaa atg ccg cag aag   192
Cys Leu Ser Ser Ser Asp Asp Glu Leu Gln Pro Glu Met Pro Gln Lys
    50                  55                  60 cag gct gag aaa gtg gtg atc aaa aag gag aaa gac atc tct gct ccc   240
Gln Ala Glu Lys Val Val Ile Lys Lys Glu Lys Asp Ile Ser Ala Pro
65                  70                  75                  80 aat gac ggc act gcc caa agt act gaa aat cat ggg gct ccc gcc tgc   288
Asn Asp Gly Thr Ala Gln Ser Thr Glu Asn His Gly Ala Pro Ala Cys
                85                  90                  95
```

```
                                                  -continued cac agg ctc aaa gag gag gaa gac gag tat gag aca tca ggg gag ggc      336
His Arg Leu Lys Glu Glu Glu Asp Glu Tyr Glu Thr Ser Gly Glu Gly
            100                 105                 110 cag gac att tgg gac atg ctg gat aaa agg aac ccc ttc cag ttt tac      384
Gln Asp Ile Trp Asp Met Leu Asp Lys Arg Asn Pro Phe Gln Phe Tyr
        115                 120                 125 ctc act aga gtc tct gga gtt aag cca aag tat aac tct gga gcc ctc      432
Leu Thr Arg Val Ser Gly Val Lys Pro Lys Tyr Asn Ser Gly Ala Leu
    130                 135                 140 cac atc aag gat att tta tct cct tta ttt ggg acg ctt gtt tct tca      480
His Ile Lys Asp Ile Leu Ser Pro Leu Phe Gly Thr Leu Val Ser Ser
145                 150                 155                 160 gct cag ttt aac tac tgc ttt gac gtg gac tgg ctc gta aaa cag tat      528
Ala Gln Phe Asn Tyr Cys Phe Asp Val Asp Trp Leu Val Lys Gln Tyr
                165                 170                 175 cca cca gaa ttc cgt aag aag cca atc ctg ctt gtg cat ggt gat aag      576
Pro Pro Glu Phe Arg Lys Lys Pro Ile Leu Leu Val His Gly Asp Lys
            180                 185                 190 cga gag gct aag gct cac ctc cat gcc cag gcc aag cct tac gag aac      624
Arg Glu Ala Lys Ala His Leu His Ala Gln Ala Lys Pro Tyr Glu Asn
        195                 200                 205 atc tct ctc tgc cag gca aag ttg gat att gcg ttt gga aca cac cac      672
Ile Ser Leu Cys Gln Ala Lys Leu Asp Ile Ala Phe Gly Thr His His
    210                 215                 220 acg aaa atg atg ctg ctg ctc tat gaa gaa ggc ctc cgg gtt gtc ata      720
Thr Lys Met Met Leu Leu Leu Tyr Glu Glu Gly Leu Arg Val Val Ile
225                 230                 235                 240 cac acc tcc aac ctc atc cat gct gac tgg cac cag aaa act caa gga      768
His Thr Ser Asn Leu Ile His Ala Asp Trp His Gln Lys Thr Gln Gly
                245                 250                 255 ata tgg ttg agc ccc tta tac cca cga att gct gat gga acc cac aaa      816
Ile Trp Leu Ser Pro Leu Tyr Pro Arg Ile Ala Asp Gly Thr His Lys
            260                 265                 270 tct gga gag tcg cca aca cat ttt aaa gct gat ctc atc agt tac ttg      864
Ser Gly Glu Ser Pro Thr His Phe Lys Ala Asp Leu Ile Ser Tyr Leu
        275                 280                 285 atg gct tat aat gcc cct tct ctc aag gag tgg ata gat gtc att cac      912
Met Ala Tyr Asn Ala Pro Ser Leu Lys Glu Trp Ile Asp Val Ile His
    290                 295                 300 aag cac gat ctc tct gaa aca aat gtt tat ctt att ggt tca acc cca      960
Lys His Asp Leu Ser Glu Thr Asn Val Tyr Leu Ile Gly Ser Thr Pro
305                 310                 315                 320 gga cgc ttt caa gga agt caa aaa gat aat tgg gga cat ttt aga ctt     1008
Gly Arg Phe Gln Gly Ser Gln Lys Asp Asn Trp Gly His Phe Arg Leu
                325                 330                 335 aag aag ctt ctg aaa gac cat gcc tca tcc atg cct aac cca gag tcc     1056
Lys Lys Leu Leu Lys Asp His Ala Ser Ser Met Pro Asn Pro Glu Ser
            340                 345                 350 tgg cct gtc gta ggt cag ttt tca agc gtt ggc tcc ttg gga gcc gat     1104
Trp Pro Val Val Gly Gln Phe Ser Ser Val Gly Ser Leu Gly Ala Asp
        355                 360                 365 gaa tca aag tgg tta tgt tct gag ttt aaa gag agc atg ctg aca ctg     1152
Glu Ser Lys Trp Leu Cys Ser Glu Phe Lys Glu Ser Met Leu Thr Leu
    370                 375                 380 ggg aag gaa agc aag act cca gga aaa agc tct gtt cct ctt tac ttg     1200
Gly Lys Glu Ser Lys Thr Pro Gly Lys Ser Ser Val Pro Leu Tyr Leu
385                 390                 395                 400 atc tat cct tct gtg gaa aat gtg cgg acc agt tta gaa gga tat cct     1248
Ile Tyr Pro Ser Val Glu Asn Val Arg Thr Ser Leu Glu Gly Tyr Pro
                405                 410                 415
```

-continued

```
gct ggg ggc tct ctt ccc tat agc atc cag aca gct gaa aaa cag aat     1296
Ala Gly Gly Ser Leu Pro Tyr Ser Ile Gln Thr Ala Glu Lys Gln Asn
            420                 425                 430 tgg ctg cat tcc tat ttt cac aaa tgg tca gct gag act tct ggc cgc     1344
Trp Leu His Ser Tyr Phe His Lys Trp Ser Ala Glu Thr Ser Gly Arg
        435                 440                 445 agc aat gcc atg cca cat att aag aca tat atg agg cct tct cca gac     1392
Ser Asn Ala Met Pro His Ile Lys Thr Tyr Met Arg Pro Ser Pro Asp
    450                 455                 460 ttc agt aaa att gct tgg ttc ctt gtc aca agc gca aat ctg tcc aag     1440
Phe Ser Lys Ile Ala Trp Phe Leu Val Thr Ser Ala Asn Leu Ser Lys
465                 470                 475                 480 gct gcc tgg gga gca ttg gag aag aat ggc acc cag ctg atg atc cgc     1488
Ala Ala Trp Gly Ala Leu Glu Lys Asn Gly Thr Gln Leu Met Ile Arg
                485                 490                 495 tcc tac gag ctc ggg gtc ctt ttt ctc cct tca gca ttt ggt cta gac     1536
Ser Tyr Glu Leu Gly Val Leu Phe Leu Pro Ser Ala Phe Gly Leu Asp
            500                 505                 510 agt ttc aaa gtg aaa cag aag ttc ttc gct ggc agc cag gag cca atg     1584
Ser Phe Lys Val Lys Gln Lys Phe Phe Ala Gly Ser Gln Glu Pro Met
        515                 520                 525 gcc acc ttt cct gtg cca tat gat ttg cct cca gaa ctg tat gga agt     1632
Ala Thr Phe Pro Val Pro Tyr Asp Leu Pro Pro Glu Leu Tyr Gly Ser
    530                 535                 540 aaa gat cgg cca tgg ata tgg aac att cct tat gtc aaa gca ccg gat     1680
Lys Asp Arg Pro Trp Ile Trp Asn Ile Pro Tyr Val Lys Ala Pro Asp
545                 550                 555                 560 acg cat ggg aac atg tgg gtg ccc tcc                                 1707
Thr His Gly Asn Met Trp Val Pro Ser
                565
```

<210> SEQ ID NO 8
<211> LENGTH: 569
<212> TYPE: PRT
<213> ORGANISM: Homo sapiens

<400> SEQUENCE: 8

```
Ala Ala Asn Glu Pro Arg Tyr Thr Cys Ser Glu Ala Gln Lys Ala Ala
1               5                   10                  15

His Lys Arg Lys Ile Ser Pro Val Lys Phe Ser Asn Thr Asp Ser Val
            20                  25                  30

Leu Pro Pro Lys Arg Gln Lys Ser Gly Ser Gln Glu Asp Leu Gly Trp
        35                  40                  45

Cys Leu Ser Ser Ser Asp Asp Glu Leu Gln Pro Glu Met Pro Gln Lys
    50                  55                  60

Gln Ala Glu Lys Val Val Ile Lys Lys Glu Lys Asp Ile Ser Ala Pro
65                  70                  75                  80

Asn Asp Gly Thr Ala Gln Ser Thr Glu Asn His Gly Ala Pro Ala Cys
                85                  90                  95

His Arg Leu Lys Glu Glu Glu Asp Glu Tyr Glu Thr Ser Gly Glu Gly
            100                 105                 110

Gln Asp Ile Trp Asp Met Leu Asp Lys Arg Asn Pro Phe Gln Phe Tyr
        115                 120                 125

Leu Thr Arg Val Ser Gly Val Lys Pro Lys Tyr Asn Ser Gly Ala Leu
    130                 135                 140

His Ile Lys Asp Ile Leu Ser Pro Leu Phe Gly Thr Leu Val Ser Ser
145                 150                 155                 160
```

```
Ala Gln Phe Asn Tyr Cys Phe Asp Val Asp Trp Leu Val Lys Gln Tyr
                165                 170                 175

Pro Pro Glu Phe Arg Lys Pro Ile Leu Leu Val His Gly Asp Lys
            180                 185                 190

Arg Glu Ala Lys Ala His Leu His Ala Gln Ala Lys Pro Tyr Glu Asn
            195                 200                 205

Ile Ser Leu Cys Gln Ala Lys Leu Asp Ile Ala Phe Gly Thr His His
    210                 215                 220

Thr Lys Met Met Leu Leu Leu Tyr Glu Glu Gly Leu Arg Val Val Ile
225                 230                 235                 240

His Thr Ser Asn Leu Ile His Ala Asp Trp His Gln Lys Thr Gln Gly
                245                 250                 255

Ile Trp Leu Ser Pro Leu Tyr Pro Arg Ile Ala Asp Gly Thr His Lys
            260                 265                 270

Ser Gly Glu Ser Pro Thr His Phe Lys Ala Asp Leu Ile Ser Tyr Leu
        275                 280                 285

Met Ala Tyr Asn Ala Pro Ser Leu Lys Glu Trp Ile Asp Val Ile His
    290                 295                 300

Lys His Asp Leu Ser Glu Thr Asn Val Tyr Leu Ile Gly Ser Thr Pro
305                 310                 315                 320

Gly Arg Phe Gln Gly Ser Gln Lys Asp Asn Trp Gly His Phe Arg Leu
                325                 330                 335

Lys Lys Leu Leu Lys Asp His Ala Ser Ser Met Pro Asn Pro Glu Ser
            340                 345                 350

Trp Pro Val Val Gly Gln Phe Ser Val Gly Ser Leu Gly Ala Asp
            355                 360                 365

Glu Ser Lys Trp Leu Cys Ser Glu Phe Lys Glu Ser Met Leu Thr Leu
370                 375                 380

Gly Lys Glu Ser Lys Thr Pro Gly Lys Ser Ser Val Pro Leu Tyr Leu
385                 390                 395                 400

Ile Tyr Pro Ser Val Glu Asn Val Arg Thr Ser Leu Glu Gly Tyr Pro
            405                 410                 415

Ala Gly Gly Ser Leu Pro Tyr Ser Ile Gln Thr Ala Glu Lys Gln Asn
            420                 425                 430

Trp Leu His Ser Tyr Phe His Lys Trp Ser Ala Glu Thr Ser Gly Arg
        435                 440                 445

Ser Asn Ala Met Pro His Ile Lys Thr Tyr Met Arg Pro Ser Pro Asp
450                 455                 460

Phe Ser Lys Ile Ala Trp Phe Leu Val Thr Ser Ala Asn Leu Ser Lys
465                 470                 475                 480

Ala Ala Trp Gly Ala Leu Glu Lys Asn Gly Thr Gln Leu Met Ile Arg
            485                 490                 495

Ser Tyr Glu Leu Gly Val Leu Phe Leu Pro Ser Ala Phe Gly Leu Asp
            500                 505                 510

Ser Phe Lys Val Lys Gln Lys Phe Phe Ala Gly Ser Gln Glu Pro Met
        515                 520                 525

Ala Thr Phe Pro Val Pro Tyr Asp Leu Pro Pro Glu Leu Tyr Gly Ser
        530                 535                 540

Lys Asp Arg Pro Trp Ile Trp Asn Ile Pro Tyr Val Lys Ala Pro Asp
545                 550                 555                 560

Thr His Gly Asn Met Trp Val Pro Ser
                565
```

-continued

<210> SEQ ID NO 9
<211> LENGTH: 1302
<212> TYPE: DNA
<213> ORGANISM: Homo sapiens
<220> FEATURE:
<221> NAME/KEY: CDS
<222> LOCATION: (1)..(1302)

<400> SEQUENCE: 9

| aag | cca | aag | tat | aac | tct | gga | gcc | ctc | cac | atc | aag | gat | att | tta | tct | 48 |
| Lys | Pro | Lys | Tyr | Asn | Ser | Gly | Ala | Leu | His | Ile | Lys | Asp | Ile | Leu | Ser | |
| 1 | | | | 5 | | | | | 10 | | | | | 15 | | |
| cct | tta | ttt | ggg | acg | ctt | gtt | tct | tca | gct | cag | ttt | aac | tac | tgc | ttt | 96 |
| Pro | Leu | Phe | Gly | Thr | Leu | Val | Ser | Ser | Ala | Gln | Phe | Asn | Tyr | Cys | Phe | |
| | | | 20 | | | | | 25 | | | | | 30 | | | |
| gac | gtg | gac | tgg | ctc | gta | aaa | cag | tat | cca | cca | gaa | ttc | cgt | aag | aag | 144 |
| Asp | Val | Asp | Trp | Leu | Val | Lys | Gln | Tyr | Pro | Pro | Glu | Phe | Arg | Lys | Lys | |
| | | 35 | | | | | 40 | | | | | 45 | | | | |
| cca | atc | ctg | ctt | gtg | cat | ggt | gat | aag | cga | gag | gct | aag | gct | cac | ctc | 192 |
| Pro | Ile | Leu | Leu | Val | His | Gly | Asp | Lys | Arg | Glu | Ala | Lys | Ala | His | Leu | |
| | 50 | | | | | 55 | | | | | 60 | | | | | |
| cat | gcc | cag | gcc | aag | cct | tac | gag | aac | atc | tct | ctc | tgc | cag | gca | aag | 240 |
| His | Ala | Gln | Ala | Lys | Pro | Tyr | Glu | Asn | Ile | Ser | Leu | Cys | Gln | Ala | Lys | |
| 65 | | | | | 70 | | | | | 75 | | | | | 80 | |
| ttg | gat | att | gcg | ttt | gga | aca | cac | cac | acg | aaa | atg | atg | ctg | ctg | ctc | 288 |
| Leu | Asp | Ile | Ala | Phe | Gly | Thr | His | His | Thr | Lys | Met | Met | Leu | Leu | Leu | |
| | | | | 85 | | | | | 90 | | | | | 95 | | |
| tat | gaa | gaa | ggc | ctc | cgg | gtt | gtc | ata | cac | acc | tcc | aac | ctc | atc | cat | 336 |
| Tyr | Glu | Glu | Gly | Leu | Arg | Val | Val | Ile | His | Thr | Ser | Asn | Leu | Ile | His | |
| | | | 100 | | | | | 105 | | | | | 110 | | | |
| gct | gac | tgg | cac | cag | aaa | act | caa | gga | ata | tgg | ttg | agc | ccc | tta | tac | 384 |
| Ala | Asp | Trp | His | Gln | Lys | Thr | Gln | Gly | Ile | Trp | Leu | Ser | Pro | Leu | Tyr | |
| | | 115 | | | | | 120 | | | | | 125 | | | | |
| cca | cga | att | gct | gat | gga | acc | cac | aaa | tct | gga | gag | tcg | cca | aca | cat | 432 |
| Pro | Arg | Ile | Ala | Asp | Gly | Thr | His | Lys | Ser | Gly | Glu | Ser | Pro | Thr | His | |
| | 130 | | | | | 135 | | | | | 140 | | | | | |
| ttt | aaa | gct | gat | ctc | atc | agt | tac | ttg | atg | gct | tat | aat | gcc | cct | tct | 480 |
| Phe | Lys | Ala | Asp | Leu | Ile | Ser | Tyr | Leu | Met | Ala | Tyr | Asn | Ala | Pro | Ser | |
| 145 | | | | | 150 | | | | | 155 | | | | | 160 | |
| ctc | aag | gag | tgg | ata | gat | gtc | att | cac | aag | cac | gat | ctc | tct | gaa | aca | 528 |
| Leu | Lys | Glu | Trp | Ile | Asp | Val | Ile | His | Lys | His | Asp | Leu | Ser | Glu | Thr | |
| | | | | 165 | | | | | 170 | | | | | 175 | | |
| aat | gtt | tat | ctt | att | ggt | tca | acc | cca | gga | cgc | ttt | caa | gga | agt | caa | 576 |
| Asn | Val | Tyr | Leu | Ile | Gly | Ser | Thr | Pro | Gly | Arg | Phe | Gln | Gly | Ser | Gln | |
| | | | 180 | | | | | 185 | | | | | 190 | | | |
| aaa | gat | aat | tgg | gga | cat | ttt | aga | ctt | aag | aag | ctt | ctg | aaa | gac | cat | 624 |
| Lys | Asp | Asn | Trp | Gly | His | Phe | Arg | Leu | Lys | Lys | Leu | Leu | Lys | Asp | His | |
| | | 195 | | | | | 200 | | | | | 205 | | | | |
| gcc | tca | tcc | atg | cct | aac | cca | gag | tcc | tgg | cct | gtc | gta | ggt | cag | ttt | 672 |
| Ala | Ser | Ser | Met | Pro | Asn | Pro | Glu | Ser | Trp | Pro | Val | Val | Gly | Gln | Phe | |
| | 210 | | | | | 215 | | | | | 220 | | | | | |
| tca | agc | gtt | ggc | tcc | ttg | gga | gcc | gat | gaa | tca | aag | tgg | tta | tgt | tct | 720 |
| Ser | Ser | Val | Gly | Ser | Leu | Gly | Ala | Asp | Glu | Ser | Lys | Trp | Leu | Cys | Ser | |
| 225 | | | | | 230 | | | | | 235 | | | | | 240 | |
| gag | ttt | aaa | gag | agc | atg | ctg | aca | ctg | ggg | aag | gaa | agc | aag | act | cca | 768 |
| Glu | Phe | Lys | Glu | Ser | Met | Leu | Thr | Leu | Gly | Lys | Glu | Ser | Lys | Thr | Pro | |
| | | | | 245 | | | | | 250 | | | | | 255 | | |
| gga | aaa | agc | tct | gtt | cct | ctt | tac | ttg | atc | tat | cct | tct | gtg | gaa | aat | 816 |
| Gly | Lys | Ser | Ser | Val | Pro | Leu | Tyr | Leu | Ile | Tyr | Pro | Ser | Val | Glu | Asn | |
| | | | 260 | | | | | 265 | | | | | 270 | | | |
| gtg | cgg | acc | agt | tta | gaa | gga | tat | cct | gct | ggg | ggc | tct | ctt | ccc | tat | 864 |
| Val | Arg | Thr | Ser | Leu | Glu | Gly | Tyr | Pro | Ala | Gly | Gly | Ser | Leu | Pro | Tyr | |
| | | 275 | | | | | 280 | | | | | 285 | | | | |
| agc | atc | cag | aca | gct | gaa | aaa | cag | aat | tgg | ctg | cat | tcc | tat | ttt | cac | 912 |
| Ser | Ile | Gln | Thr | Ala | Glu | Lys | Gln | Asn | Trp | Leu | His | Ser | Tyr | Phe | His | |
| | 290 | | | | | 295 | | | | | 300 | | | | | |
| aaa | tgg | tca | gct | gag | act | tct | ggc | cgc | agc | aat | gcc | atg | cca | cat | att | 960 |
| Lys | Trp | Ser | Ala | Glu | Thr | Ser | Gly | Arg | Ser | Asn | Ala | Met | Pro | His | Ile | |
| 305 | | | | | 310 | | | | | 315 | | | | | 320 | |
| aag | aca | tat | atg | agg | cct | tct | cca | gac | ttc | agt | aaa | att | gct | tgg | ttc | 1008 |
| Lys | Thr | Tyr | Met | Arg | Pro | Ser | Pro | Asp | Phe | Ser | Lys | Ile | Ala | Trp | Phe | |
| | | | | 325 | | | | | 330 | | | | | 335 | | |
| ctt | gtc | aca | agc | gca | aat | ctg | tcc | aag | gct | gcc | tgg | gga | gca | ttg | gag | 1056 |
| Leu | Val | Thr | Ser | Ala | Asn | Leu | Ser | Lys | Ala | Ala | Trp | Gly | Ala | Leu | Glu | |
| | | | 340 | | | | | 345 | | | | | 350 | | | |
| aag | aat | ggc | acc | cag | ctg | atg | atc | cgc | tcc | tac | gag | ctc | ggg | gtc | ctt | 1104 |
| Lys | Asn | Gly | Thr | Gln | Leu | Met | Ile | Arg | Ser | Tyr | Glu | Leu | Gly | Val | Leu | |
| | | 355 | | | | | 360 | | | | | 365 | | | | |

```
ttt ctc cct tca gca ttt ggt cta gac agt ttc aaa gtg aaa cag aag      1152
Phe Leu Pro Ser Ala Phe Gly Leu Asp Ser Phe Lys Val Lys Gln Lys
370                 375                 380 ttc ttc gct ggc agc cag gag cca atg gcc acc ttt cct gtg cca tat      1200
Phe Phe Ala Gly Ser Gln Glu Pro Met Ala Thr Phe Pro Val Pro Tyr
385                 390                 395                 400 gat ttg cct cca gaa ctg tat gga agt aaa gat cgg cca tgg ata tgg      1248
Asp Leu Pro Pro Glu Leu Tyr Gly Ser Lys Asp Arg Pro Trp Ile Trp
            405                 410                 415 aac att cct tat gtc aaa gca ccg gat acg cat ggg aac atg tgg gtg      1296
Asn Ile Pro Tyr Val Lys Ala Pro Asp Thr His Gly Asn Met Trp Val
        420                 425                 430 ccc tcc                                                              1302
Pro Ser
```

<210> SEQ ID NO 10
<211> LENGTH: 434
<212> TYPE: PRT
<213> ORGANISM: Homo sapiens

<400> SEQUENCE: 10

```
Lys Pro Lys Tyr Asn Ser Gly Ala Leu His Ile Lys Asp Ile Leu Ser
1               5                   10                  15

Pro Leu Phe Gly Thr Leu Val Ser Ser Ala Gln Phe Asn Tyr Cys Phe
            20                  25                  30

Asp Val Asp Trp Leu Val Lys Gln Tyr Pro Pro Glu Phe Arg Lys Lys
        35                  40                  45

Pro Ile Leu Leu Val His Gly Asp Lys Arg Glu Ala Lys Ala His Leu
    50                  55                  60

His Ala Gln Ala Lys Pro Tyr Glu Asn Ile Ser Leu Cys Gln Ala Lys
65                  70                  75                  80

Leu Asp Ile Ala Phe Gly Thr His Thr Lys Met Met Leu Leu Leu
                85                  90                  95

Tyr Glu Glu Gly Leu Arg Val Val Ile His Thr Ser Asn Leu Ile His
                100                 105                 110

Ala Asp Trp His Gln Lys Thr Gln Gly Ile Trp Leu Ser Pro Leu Tyr
            115                 120                 125

Pro Arg Ile Ala Asp Gly Thr His Lys Ser Gly Glu Ser Pro Thr His
    130                 135                 140

Phe Lys Ala Asp Leu Ile Ser Tyr Leu Met Ala Tyr Asn Ala Pro Ser
145                 150                 155                 160

Leu Lys Glu Trp Ile Asp Val Ile His Lys His Asp Leu Ser Glu Thr
                165                 170                 175

Asn Val Tyr Leu Ile Gly Ser Thr Pro Gly Arg Phe Gln Gly Ser Gln
            180                 185                 190

Lys Asp Asn Trp Gly His Phe Arg Leu Lys Lys Leu Leu Lys Asp His
        195                 200                 205

Ala Ser Ser Met Pro Asn Pro Glu Ser Trp Pro Val Val Gly Gln Phe
    210                 215                 220

Ser Ser Val Gly Ser Leu Gly Ala Asp Glu Ser Lys Trp Leu Cys Ser
225                 230                 235                 240

Glu Phe Lys Glu Ser Met Leu Thr Leu Gly Lys Glu Ser Lys Thr Pro
                245                 250                 255

Gly Lys Ser Ser Val Pro Leu Tyr Leu Ile Tyr Pro Ser Val Glu Asn
            260                 265                 270

Val Arg Thr Ser Leu Glu Gly Tyr Pro Ala Gly Gly Ser Leu Pro Tyr
        275                 280                 285

Ser Ile Gln Thr Ala Glu Lys Gln Asn Trp Leu His Ser Tyr Phe His
    290                 295                 300
```

```
Lys Trp Ser Ala Glu Thr Ser Gly Arg Ser Asn Ala Met Pro His Ile
305                 310                 315                 320

Lys Thr Tyr Met Arg Pro Ser Pro Asp Phe Ser Lys Ile Ala Trp Phe
            325                 330                 335

Leu Val Thr Ser Ala Asn Leu Ser Lys Ala Ala Trp Gly Ala Leu Glu
            340                 345                 350

Lys Asn Gly Thr Gln Leu Met Ile Arg Ser Tyr Glu Leu Gly Val Leu
            355                 360                 365

Phe Leu Pro Ser Ala Phe Gly Leu Asp Ser Phe Lys Val Lys Gln Lys
370                 375                 380

Phe Phe Ala Gly Ser Gln Glu Pro Met Ala Thr Phe Pro Val Pro Tyr
385                 390                 395                 400

Asp Leu Pro Pro Glu Leu Tyr Gly Ser Lys Asp Arg Pro Trp Ile Trp
            405                 410                 415

Asn Ile Pro Tyr Val Lys Ala Pro Asp Thr His Gly Asn Met Trp Val
            420                 425                 430

Pro Ser

<210> SEQ ID NO 11
<211> LENGTH: 1521
<212> TYPE: DNA
<213> ORGANISM: Homo sapiens
<220> FEATURE:
<221> NAME/KEY: CDS
<222> LOCATION: (1)..(1521)

<400> SEQUENCE: 11
```

| | | | | | | | | | | | | | | | | |
|---|---|---|---|---|---|---|---|---|---|---|---|---|---|---|---|---|
| gca | gca | aat | gag | ccc | agg | tac | acc | tgt | tcc | gag | gcc | cag | aaa | gct | gca | 48 |
| Ala | Ala | Asn | Glu | Pro | Arg | Tyr | Thr | Cys | Ser | Glu | Ala | Gln | Lys | Ala | Ala | |
| 1 | | | | 5 | | | | | 10 | | | | | 15 | | |
| cac | aag | agg | aaa | ata | tca | cct | gtg | aaa | ttc | agc | aat | aca | gat | tca | gtt | 96 |
| His | Lys | Arg | Lys | Ile | Ser | Pro | Val | Lys | Phe | Ser | Asn | Thr | Asp | Ser | Val | |
| | | | 20 | | | | 25 | | | | | 30 | | | | |
| tta | cct | ccc | aaa | agg | cag | aaa | agc | ggt | tcc | cag | gag | gac | ctc | ggc | tgg | 144 |
| Leu | Pro | Pro | Lys | Arg | Gln | Lys | Ser | Gly | Ser | Gln | Glu | Asp | Leu | Gly | Trp | |
| | | | 35 | | | | 40 | | | | | 45 | | | | |
| tgt | ctg | tcc | agc | agt | gat | gat | gag | ctg | caa | cca | gaa | atg | ccg | cag | aag | 192 |
| Cys | Leu | Ser | Ser | Ser | Asp | Asp | Glu | Leu | Gln | Pro | Glu | Met | Pro | Gln | Lys | |
| | 50 | | | | | 55 | | | | | 60 | | | | | |
| cag | gct | gag | aaa | gtg | gtg | atc | aaa | aag | gag | aaa | gac | atc | tct | gct | ccc | 240 |
| Gln | Ala | Glu | Lys | Val | Val | Ile | Lys | Lys | Glu | Lys | Asp | Ile | Ser | Ala | Pro | |
| 65 | | | | 70 | | | | | 75 | | | | | 80 | | |
| aat | gac | ggc | act | gcc | caa | agt | act | gaa | aat | cat | ggg | gct | ccc | gcc | tgc | 288 |
| Asn | Asp | Gly | Thr | Ala | Gln | Ser | Thr | Glu | Asn | His | Gly | Ala | Pro | Ala | Cys | |
| | | | | 85 | | | | | 90 | | | | | 95 | | |
| cac | agg | ctc | aaa | gag | gag | gaa | gac | gag | tat | gag | aca | tca | ggg | gag | ggc | 336 |
| His | Arg | Leu | Lys | Glu | Glu | Glu | Asp | Glu | Tyr | Glu | Thr | Ser | Gly | Glu | Gly | |
| | | | 100 | | | | | 105 | | | | | 110 | | | |
| cag | gac | att | tgg | gac | atg | ctg | gat | aaa | agg | aac | ccc | ttc | cag | ttt | tac | 384 |
| Gln | Asp | Ile | Trp | Asp | Met | Leu | Asp | Lys | Arg | Asn | Pro | Phe | Gln | Phe | Tyr | |
| | | | 115 | | | | | 120 | | | | | 125 | | | |
| ctc | act | aga | gtc | tct | gga | gtt | aag | cca | aag | tat | aac | tct | gga | gcc | ctc | 432 |
| Leu | Thr | Arg | Val | Ser | Gly | Val | Lys | Pro | Lys | Tyr | Asn | Ser | Gly | Ala | Leu | |
| | | 130 | | | | | 135 | | | | | 140 | | | | |
| cac | atc | aag | gat | att | tta | tct | cct | tta | ttt | ggg | acg | ctt | gtt | tct | tca | 480 |
| His | Ile | Lys | Asp | Ile | Leu | Ser | Pro | Leu | Phe | Gly | Thr | Leu | Val | Ser | Ser | |
| 145 | | | | 150 | | | | | 155 | | | | | 160 | | |
| gct | cag | ttt | aac | tac | tgc | ttt | gac | gtg | gac | tgg | ctc | gta | aaa | cag | tat | 528 |

-continued

| | | |
|---|---|---|
| Ala Gln Phe Asn Tyr Cys Phe Asp Val Asp Trp Leu Val Lys Gln Tyr<br>                      165                    170                  175 | |
| cca cca gaa ttc cgt aag aag cca atc ctg ctt gtg cat ggt gat aag<br>Pro Pro Glu Phe Arg Lys Lys Pro Ile Leu Leu Val His Gly Asp Lys<br>        180                    185                    190 | 576 |
| cga gag gct aag gct cac ctc cat gcc cag gcc aag cct tac gag aac<br>Arg Glu Ala Lys Ala His Leu His Ala Gln Ala Lys Pro Tyr Glu Asn<br>           195                    200                    205 | 624 |
| atc tct ctc tgc cag gca aag ttg gat att gcg ttt gga aca cac cac<br>Ile Ser Leu Cys Gln Ala Lys Leu Asp Ile Ala Phe Gly Thr His His<br>        210                    215                    220 | 672 |
| acg aaa atg atg ctg ctg ctc tat gaa gaa ggc ctc cgg gtt gtc ata<br>Thr Lys Met Met Leu Leu Leu Tyr Glu Glu Gly Leu Arg Val Val Ile<br>225                    230                    235                    240 | 720 |
| cac acc tcc aac ctc atc cat gct gac tgg cac cag aaa act caa gga<br>His Thr Ser Asn Leu Ile His Ala Asp Trp His Gln Lys Thr Gln Gly<br>                  245                    250                    255 | 768 |
| ata tgg ttg agc ccc tta tac cca cga att gct gat gga acc cac aaa<br>Ile Trp Leu Ser Pro Leu Tyr Pro Arg Ile Ala Asp Gly Thr His Lys<br>                    260                    265                    270 | 816 |
| tct gga gag tcg cca aca cat ttt aaa gct gat ctc atc agt tac ttg<br>Ser Gly Glu Ser Pro Thr His Phe Lys Ala Asp Leu Ile Ser Tyr Leu<br>           275                    280                    285 | 864 |
| atg gct tat aat gcc cct tct ctc aag gag tgg ata gat gtc att cac<br>Met Ala Tyr Asn Ala Pro Ser Leu Lys Glu Trp Ile Asp Val Ile His<br>        290                    295                    300 | 912 |
| aag cac gat ctc tct gaa aca aat gtt tat ctt att ggt tca acc cca<br>Lys His Asp Leu Ser Glu Thr Asn Val Tyr Leu Ile Gly Ser Thr Pro<br>305                    310                    315                    320 | 960 |
| gga cgc ttt caa gga agt caa aaa gat aat tgg gga cat ttt aga ctt<br>Gly Arg Phe Gln Gly Ser Gln Lys Asp Asn Trp Gly His Phe Arg Leu<br>                    325                    330                    335 | 1008 |
| aag aag ctt ctg aaa gac cat gcc tca tcc atg cct aac cca gag tcc<br>Lys Lys Leu Leu Lys Asp His Ala Ser Ser Met Pro Asn Pro Glu Ser<br>                340                    345                    350 | 1056 |
| tgg cct gtc gta ggt cag ttt tca agc gtt ggc tcc ttg gga gcc gat<br>Trp Pro Val Val Gly Gln Phe Ser Ser Val Gly Ser Leu Gly Ala Asp<br>           355                    360                    365 | 1104 |
| gaa tca aag tgg tta tgt tct gag ttt aaa gag agc atg ctg aca ctg<br>Glu Ser Lys Trp Leu Cys Ser Glu Phe Lys Glu Ser Met Leu Thr Leu<br>        370                    375                    380 | 1152 |
| ggg aag gaa agc aag act cca gga aaa agc tct gtt cct ctt tac ttg<br>Gly Lys Glu Ser Lys Thr Pro Gly Lys Ser Ser Val Pro Leu Tyr Leu<br>385                    390                    395                    400 | 1200 |
| atc tat cct tct gtg gaa aat gtg cgg acc agt tta gaa gga tat cct<br>Ile Tyr Pro Ser Val Glu Asn Val Arg Thr Ser Leu Glu Gly Tyr Pro<br>                  405                    410                    415 | 1248 |
| gct ggg ggc tct ctt ccc tat agc atc cag aca gct gaa aaa cag aat<br>Ala Gly Gly Ser Leu Pro Tyr Ser Ile Gln Thr Ala Glu Lys Gln Asn<br>           420                    425                    430 | 1296 |
| tgg ctg cat tcc tat ttt cac aaa tgg tca gct gag act tct ggc cgc<br>Trp Leu His Ser Tyr Phe His Lys Trp Ser Ala Glu Thr Ser Gly Arg<br>                435                    440                    445 | 1344 |
| agc aat gcc atg cca cat att aag aca tat atg agg cct tct cca gac<br>Ser Asn Ala Met Pro His Ile Lys Thr Tyr Met Arg Pro Ser Pro Asp<br>        450                    455                    460 | 1392 |
| ttc agt aaa att gct tgg ttc ctt gtc aca agc gca aat ctg tcc aag<br>Phe Ser Lys Ile Ala Trp Phe Leu Val Thr Ser Ala Asn Leu Ser Lys<br>465                    470                    475                    480 | 1440 |

-continued

```
gct gcc tgg gga gca ttg gag aag aat ggc acc cag ctg atg atc cgc      1488
Ala Ala Trp Gly Ala Leu Glu Lys Asn Gly Thr Gln Leu Met Ile Arg
                485                 490                 495 tcc tac gag ctc ggg gtc ctt ttt ctc cct tca                          1521
Ser Tyr Glu Leu Gly Val Leu Phe Leu Pro Ser
                500                 505
```

<210> SEQ ID NO 12
<211> LENGTH: 507
<212> TYPE: PRT
<213> ORGANISM: Homo sapiens

<400> SEQUENCE: 12

```
Ala Ala Asn Glu Pro Arg Tyr Thr Cys Ser Glu Ala Gln Lys Ala Ala
1               5                   10                  15

His Lys Arg Lys Ile Ser Pro Val Lys Phe Ser Asn Thr Asp Ser Val
                20                  25                  30

Leu Pro Pro Lys Arg Gln Lys Ser Gly Ser Gln Glu Asp Leu Gly Trp
            35                  40                  45

Cys Leu Ser Ser Ser Asp Asp Glu Leu Gln Pro Glu Met Pro Gln Lys
50                  55                  60

Gln Ala Glu Lys Val Val Ile Lys Lys Glu Lys Asp Ile Ser Ala Pro
65                  70                  75                  80

Asn Asp Gly Thr Ala Gln Ser Thr Glu Asn His Gly Ala Pro Ala Cys
                85                  90                  95

His Arg Leu Lys Glu Glu Glu Asp Glu Tyr Glu Thr Ser Gly Glu Gly
            100                 105                 110

Gln Asp Ile Trp Asp Met Leu Asp Lys Arg Asn Pro Phe Gln Phe Tyr
        115                 120                 125

Leu Thr Arg Val Ser Gly Val Lys Pro Lys Tyr Asn Ser Gly Ala Leu
130                 135                 140

His Ile Lys Asp Ile Leu Ser Pro Leu Phe Gly Thr Leu Val Ser Ser
145                 150                 155                 160

Ala Gln Phe Asn Tyr Cys Phe Asp Val Asp Trp Leu Val Lys Gln Tyr
                165                 170                 175

Pro Pro Glu Phe Arg Lys Lys Pro Ile Leu Leu Val His Gly Asp Lys
            180                 185                 190

Arg Glu Ala Lys Ala His Leu His Ala Gln Ala Lys Pro Tyr Glu Asn
        195                 200                 205

Ile Ser Leu Cys Gln Ala Lys Leu Asp Ile Ala Phe Gly Thr His His
    210                 215                 220

Thr Lys Met Met Leu Leu Tyr Glu Glu Gly Leu Arg Val Ile
225                 230                 235                 240

His Thr Ser Asn Leu Ile His Ala Asp Trp His Gln Lys Thr Gln Gly
                245                 250                 255

Ile Trp Leu Ser Pro Leu Tyr Pro Arg Ile Ala Asp Gly Thr His Lys
            260                 265                 270

Ser Gly Glu Ser Pro Thr His Phe Lys Ala Asp Leu Ile Ser Tyr Leu
        275                 280                 285

Met Ala Tyr Asn Ala Pro Ser Leu Lys Glu Trp Ile Asp Val Ile His
    290                 295                 300

Lys His Asp Leu Ser Glu Thr Asn Val Tyr Leu Ile Gly Ser Thr Pro
305                 310                 315                 320

Gly Arg Phe Gln Gly Ser Gln Lys Asp Asn Trp Gly His Phe Arg Leu
                325                 330                 335
```

```
                    -continued

Lys Lys Leu Leu Lys Asp His Ala Ser Ser Met Pro Asn Pro Glu Ser
            340                 345                 350

Trp Pro Val Val Gly Gln Phe Ser Ser Val Gly Ser Leu Gly Ala Asp
        355                 360                 365

Glu Ser Lys Trp Leu Cys Ser Glu Phe Lys Ser Met Leu Thr Leu
    370                 375                 380

Gly Lys Glu Ser Lys Thr Pro Gly Lys Ser Ser Val Pro Leu Tyr Leu
385                 390                 395                 400

Ile Tyr Pro Ser Val Glu Asn Val Arg Thr Ser Leu Glu Gly Tyr Pro
                405                 410                 415

Ala Gly Gly Ser Leu Pro Tyr Ser Ile Gln Thr Ala Glu Lys Gln Asn
            420                 425                 430

Trp Leu His Ser Tyr Phe His Lys Trp Ser Ala Glu Thr Ser Gly Arg
        435                 440                 445

Ser Asn Ala Met Pro His Ile Lys Thr Tyr Met Arg Pro Ser Pro Asp
    450                 455                 460

Phe Ser Lys Ile Ala Trp Phe Leu Val Thr Ser Ala Asn Leu Ser Lys
465                 470                 475                 480

Ala Ala Trp Gly Ala Leu Glu Lys Asn Gly Thr Gln Leu Met Ile Arg
                485                 490                 495

Ser Tyr Glu Leu Gly Val Leu Phe Leu Pro Ser
            500                 505

<210> SEQ ID NO 13
<211> LENGTH: 1116
<212> TYPE: DNA
<213> ORGANISM: Homo sapiens
<220> FEATURE:
<221> NAME/KEY: CDS
<222> LOCATION: (1)..(1116)

<400> SEQUENCE: 13 aag cca aag tat aac tct gga gcc ctc cac atc aag gat att tta tct      48
Lys Pro Lys Tyr Asn Ser Gly Ala Leu His Ile Lys Asp Ile Leu Ser
1               5                   10                  15 cct tta ttt ggg acg ctt gtt tct tca gct cag ttt aac tac tgc ttt      96
Pro Leu Phe Gly Thr Leu Val Ser Ser Ala Gln Phe Asn Tyr Cys Phe
            20                  25                  30 gac gtg gac tgg ctc gta aaa cag tat cca cca gaa ttc cgt aag aag     144
Asp Val Asp Trp Leu Val Lys Gln Tyr Pro Pro Glu Phe Arg Lys Lys
        35                  40                  45 cca atc ctg ctt gtg cat ggt gat aag cga gag gct aag gct cac ctc     192
Pro Ile Leu Leu Val His Gly Asp Lys Arg Glu Ala Lys Ala His Leu
    50                  55                  60 cat gcc cag gcc aag cct tac gag aac atc tct ctc tgc cag gca aag     240
His Ala Gln Ala Lys Pro Tyr Glu Asn Ile Ser Leu Cys Gln Ala Lys
65                  70                  75                  80 ttg gat att gcg ttt gga aca cac cac acg aaa atg atg ctg ctg ctc     288
Leu Asp Ile Ala Phe Gly Thr His His Thr Lys Met Met Leu Leu Leu
                85                  90                  95 tat gaa gaa ggc ctc cgg gtt gtc ata cac acc tcc aac ctc atc cat     336
Tyr Glu Glu Gly Leu Arg Val Val Ile His Thr Ser Asn Leu Ile His
            100                 105                 110 gct gac tgg cac cag aaa act caa gga ata tgg ttg agc ccc tta tac     384
Ala Asp Trp His Gln Lys Thr Gln Gly Ile Trp Leu Ser Pro Leu Tyr
        115                 120                 125 cca cga att gct gat gga acc cac aaa tct gga gag tcg cca aca cat     432
Pro Arg Ile Ala Asp Gly Thr His Lys Ser Gly Glu Ser Pro Thr His
    130                 135                 140
```

```
ttt aaa gct gat ctc atc agt tac ttg atg gct tat aat gcc cct tct       480
Phe Lys Ala Asp Leu Ile Ser Tyr Leu Met Ala Tyr Asn Ala Pro Ser
145                 150                 155                 160 ctc aag gag tgg ata gat gtc att cac aag cac gat ctc tct gaa aca       528
Leu Lys Glu Trp Ile Asp Val Ile His Lys His Asp Leu Ser Glu Thr
                165                 170                 175 aat gtt tat ctt att ggt tca acc cca gga cgc ttt caa gga agt caa       576
Asn Val Tyr Leu Ile Gly Ser Thr Pro Gly Arg Phe Gln Gly Ser Gln
            180                 185                 190 aaa gat aat tgg gga cat ttt aga ctt aag aag ctt ctg aaa gac cat       624
Lys Asp Asn Trp Gly His Phe Arg Leu Lys Lys Leu Leu Lys Asp His
        195                 200                 205 gcc tca tcc atg cct aac cca gag tcc tgg cct gtc gta ggt cag ttt       672
Ala Ser Ser Met Pro Asn Pro Glu Ser Trp Pro Val Val Gly Gln Phe
    210                 215                 220 tca agc gtt ggc tcc ttg gga gcc gat gaa tca aag tgg tta tgt tct       720
Ser Ser Val Gly Ser Leu Gly Ala Asp Glu Ser Lys Trp Leu Cys Ser
225                 230                 235                 240 gag ttt aaa gag agc atg ctg aca ctg ggg aag gaa agc aag act cca       768
Glu Phe Lys Glu Ser Met Leu Thr Leu Gly Lys Glu Ser Lys Thr Pro
                245                 250                 255 gga aaa agc tct gtt cct ctt tac ttg atc tat cct tct gtg gaa aat       816
Gly Lys Ser Ser Val Pro Leu Tyr Leu Ile Tyr Pro Ser Val Glu Asn
            260                 265                 270 gtg cgg acc agt tta gaa gga tat cct gct ggg ggc tct ctt ccc tat       864
Val Arg Thr Ser Leu Glu Gly Tyr Pro Ala Gly Gly Ser Leu Pro Tyr
        275                 280                 285 agc atc cag aca gct gaa aaa cag aat tgg ctg cat tcc tat ttt cac       912
Ser Ile Gln Thr Ala Glu Lys Gln Asn Trp Leu His Ser Tyr Phe His
    290                 295                 300 aaa tgg tca gct gag act tct ggc cgc agc aat gcc atg cca cat att       960
Lys Trp Ser Ala Glu Thr Ser Gly Arg Ser Asn Ala Met Pro His Ile
305                 310                 315                 320 aag aca tat atg agg cct tct cca gac ttc agt aaa att gct tgg ttc      1008
Lys Thr Tyr Met Arg Pro Ser Pro Asp Phe Ser Lys Ile Ala Trp Phe
                325                 330                 335 ctt gtc aca agc gca aat ctg tcc aag gct gcc tgg gga gca ttg gag      1056
Leu Val Thr Ser Ala Asn Leu Ser Lys Ala Ala Trp Gly Ala Leu Glu
            340                 345                 350 aag aat ggc acc cag ctg atg atc cgc tcc tac gag ctc ggg gtc ctt      1104
Lys Asn Gly Thr Gln Leu Met Ile Arg Ser Tyr Glu Leu Gly Val Leu
        355                 360                 365 ttt ctc cct tca                                                       1116
Phe Leu Pro Ser
    370

<210> SEQ ID NO 14
<211> LENGTH: 372
<212> TYPE: PRT
<213> ORGANISM: Homo sapiens

<400> SEQUENCE: 14

Lys Pro Lys Tyr Asn Ser Gly Ala Leu His Ile Lys Asp Ile Leu Ser
1               5                   10                  15

Pro Leu Phe Gly Thr Leu Val Ser Ser Ala Gln Phe Asn Tyr Cys Phe
            20                  25                  30

Asp Val Asp Trp Leu Val Lys Gln Tyr Pro Pro Glu Phe Arg Lys Lys
        35                  40                  45

Pro Ile Leu Leu Val His Gly Asp Lys Arg Glu Ala Lys Ala His Leu
```

```
                    50                  55                  60
His Ala Gln Ala Lys Pro Tyr Glu Asn Ile Ser Leu Cys Gln Ala Lys
 65                  70                  75                  80

Leu Asp Ile Ala Phe Gly Thr His His Thr Lys Met Met Leu Leu Leu
                 85                  90                  95

Tyr Glu Glu Gly Leu Arg Val Val Ile His Thr Ser Asn Leu Ile His
            100                 105                 110

Ala Asp Trp His Gln Lys Thr Gln Gly Ile Trp Leu Ser Pro Leu Tyr
            115                 120                 125

Pro Arg Ile Ala Asp Gly Thr His Lys Ser Gly Glu Ser Pro Thr His
130                 135                 140

Phe Lys Ala Asp Leu Ile Ser Tyr Leu Met Ala Tyr Asn Ala Pro Ser
145                 150                 155                 160

Leu Lys Glu Trp Ile Asp Val Ile His Lys His Asp Leu Ser Glu Thr
                165                 170                 175

Asn Val Tyr Leu Ile Gly Ser Thr Pro Gly Arg Phe Gln Gly Ser Gln
            180                 185                 190

Lys Asp Asn Trp Gly His Phe Arg Leu Lys Lys Leu Leu Lys Asp His
            195                 200                 205

Ala Ser Ser Met Pro Asn Pro Glu Ser Trp Pro Val Val Gly Gln Phe
210                 215                 220

Ser Ser Val Gly Ser Leu Gly Ala Asp Glu Ser Lys Trp Leu Cys Ser
225                 230                 235                 240

Glu Phe Lys Glu Ser Met Leu Thr Leu Gly Lys Glu Ser Lys Thr Pro
                245                 250                 255

Gly Lys Ser Ser Val Pro Leu Tyr Leu Ile Tyr Pro Ser Val Glu Asn
            260                 265                 270

Val Arg Thr Ser Leu Glu Gly Tyr Pro Ala Gly Gly Ser Leu Pro Tyr
            275                 280                 285

Ser Ile Gln Thr Ala Glu Lys Gln Asn Trp Leu His Ser Tyr Phe His
            290                 295                 300

Lys Trp Ser Ala Glu Thr Ser Gly Arg Ser Asn Ala Met Pro His Ile
305                 310                 315                 320

Lys Thr Tyr Met Arg Pro Ser Pro Asp Phe Ser Lys Ile Ala Trp Phe
                325                 330                 335

Leu Val Thr Ser Ala Asn Leu Ser Lys Ala Ala Trp Gly Ala Leu Glu
            340                 345                 350

Lys Asn Gly Thr Gln Leu Met Ile Arg Ser Tyr Glu Leu Gly Val Leu
            355                 360                 365

Phe Leu Pro Ser
    370

<210> SEQ ID NO 15
<211> LENGTH: 14
<212> TYPE: PRT
<213> ORGANISM: Artificial Sequence
<220> FEATURE:
<223> OTHER INFORMATION: Synthetic

<400> SEQUENCE: 15

Trp Leu Leu Thr Ser Ala Asn Leu Ser Lys Ala Ala Trp Gly
 1               5                  10

<210> SEQ ID NO 16
<211> LENGTH: 6
<212> TYPE: PRT
```

```
<213> ORGANISM: Artificial Sequence
<220> FEATURE:
<223> OTHER INFORMATION: Synthetic

<400> SEQUENCE: 16

Tyr Glu Ala Gly Val Leu
1               5

<210> SEQ ID NO 17
<211> LENGTH: 34
<212> TYPE: DNA
<213> ORGANISM: Artificial Sequence
<220> FEATURE:
<223> OTHER INFORMATION: Synthetic

<400> SEQUENCE: 17
cgcggatcca tcacaggaag gcgattatgg gagg                                    34

<210> SEQ ID NO 18
<211> LENGTH: 29
<212> TYPE: DNA
<213> ORGANISM: Artificial Sequence
<220> FEATURE:
<223> OTHER INFORMATION: Synthetic

<400> SEQUENCE: 18
atgtggaggg ctccagagtt atactttgg                                          29

<210> SEQ ID NO 19
<211> LENGTH: 30
<212> TYPE: DNA
<213> ORGANISM: Artificial Sequence
<220> FEATURE:
<223> OTHER INFORMATION: Synthetic

<400> SEQUENCE: 19
ttaagccaaa gtataactct ggagccctcc                                         30

<210> SEQ ID NO 20
<211> LENGTH: 42
<212> TYPE: DNA
<213> ORGANISM: Artificial Sequence
<220> FEATURE:
<223> OTHER INFORMATION: Synthetic

<400> SEQUENCE: 20
cgcggatcca cttatcagga gggcacccac atgttcccat gc                           42
```

METHODS FOR DETERMINING TYROSINE-DNA PHOSPHODIESTERASE ACTIVITY

The present Application claims the benefit of U.S. Provisional Appl. Ser. No. 60/327,466, filed Oct. 5, 2001.

FIELD OF THE INVENTION

The present invention provides human tyrosine-DNA phosphodiesterases (TDPs). In particular, the present invention provides novel recombinant nucleic acids and proteins, including mutant TDPs, vectors, and TDP-producing cells, as well as co-factors for enzyme activity. The present invention further provides methods for high through-put enzymatic assay systems utilizing the TDPs of the present invention.

BACKGROUND OF THE INVENTION

Cellular DNA is subjected to constant attack by reactive free radicals, metabolites that can act as alkylating agents produced within cells and DNA damaging agents present in environment (e.g., UV light and cytotoxic compounds like camptothecin). In humans, cells have developed various sophisticated mechanisms involving at least 130 DNA repair gene products to sense and correct DNA damage, in order to minimize toxic and mutagenic consequences and to preserve the integrity of genome (Pouliot et al., Science 286:552 [1999]). Various enzymes work in concert to achieve this goal.

Topoisomerases are cellular enzymes that are crucial for replication and transcription of the genome. Topoisomerases work by cleaving the DNA backbone, thereby allowing the topological changes needed for DNA replication and transcription to occur. After these processes have been completed, topoisomerases reseal the DNA backbone (Wang, Ann. Rev. Biochem., 65:635 [1996]). In some aspects, topoisomerases work efficiently, as DNA breakage is accompanied by covalent binding between the enzyme and the DNA, to create an intermediate structure that is resolved during the resealing step. However, this mechanism also makes topoisomerases potentially dangerous. For example, if the resealing step fails, a normally transient break in DNA becomes a long-term disruption, one with a topoisomerase covalently joined to it. Unless a means to restore the continuity of the DNA is provided, the affected cell will die.

In virtually all topoisomerases, the heart of the covalent complex is a phosphodiester bond between a specific tyrosine residue of the enzyme and one end of the break (i.e., the 3' end for eukaryotic topoisomerase I and the 5' end for topoisomerases II and III). The high-energy nature of this bond normally ensures that the resealing step occurs.

Failure of the resealing step is dramatically increased by various drugs, including camptothecin. Camptothecin has been considered to be a promising anti-cancer agent because it specifically targets eukaryotic topoisomerase I (Chen et al., Ann. Rev. Pharmacol. Toxicol., 94:194 [1994]). Protein-linked breaks also accumulate when topoisomerases act on DNA containing structural lesions like thymine dimers, abasic sites and mismatched base pairs (Pommier et al., Biochem. Biophys. Acta 1400:83 [1998]). To the extent that such lesions arise during the normal cell lifespan, topoisomerase-associated damage may be unavoidable.

Repair of topoisomerase-DNA covalent complexes is important to the cell. However, the means involved in this repair are not well understood. Hydrolysis of the bond joining the topoisomerase to DNA has been proposed as a way to effect release of the topoisomerase such that the cleaved DNA could undergo conventional modes of break repair (See, e.g., Friedberg et al., *DNA Repair and Mutagenesis*, ASM Press, Washington, D.C. [1995]; Kanaar et al., Trends Cell. Biol., 8:483 [1998]). Although no such hydrolysis has been reported for covalent complexes between DNA and topoisomerases II or III, hydrolysis has been described for covalent complexes between DNA and topoisomerase I (Yang et al., Proc. Natl. Acad. Sci. USA 93:11534–11539 [1996]). Thus, there remains a need in the art to provide means to repair cellular damage, including that caused by abnormal DNA replication. Indeed, an understanding of topoisomerases and their functions is needed in order to develop means for use of topoisomerases as targets for cancer therapy or anti-aging processes.

SUMMARY OF THE INVENTION

The present invention provides human tyrosine-DNA phosphodiesterases (TDPs). In particular, the present invention provides novel recombinant nucleic acids and proteins, including mutant TDPs, vectors, and TDP-producing cells, as well as co-factors for enzyme activity. The present invention further provides methods for high through-put enzymatic assay systems utilizing the TDPs of the present invention.

In some embodiments, the present invention provides single and double-stranded nucleic acid sequences encoding human TDP. In other embodiments, the present invention provides polypeptides comprising wild-type, as well as mutant TDPs. In some preferred embodiments, the mutant polypeptides have deletions of the amino-terminal 39 or 174 amino acids and end at residues 522 or 545.

In other embodiments, the present invention provides vectors comprising nucleic acid sequences encoding wild-type and mutant TDPs. In particularly preferred embodiments, the TDPs are human. In some preferred embodiments, the vectors of the present invention are contained within host cells. In some particularly preferred embodiments, the vectors of the present invention contained within host cells express wild-type and/or mutant TDPs (i.e., the vectors are "expression vectors"). In alternative preferred embodiments, the expressed TDPs are human.

In further embodiments, the present invention provides methods for protein purification and refolding that result in the production of soluble wild-type or mutant human TDP polypeptides. In some embodiments, the soluble human TDP polypeptides are used in crystal structure determinations, while in other embodiments, the TDP polypeptides find use in high through-put screening methods.

In some embodiments, the high through-put screening methods of the present invention provide means to identify and characterize compounds capable of inhibiting, stimulating, or otherwise modulating TDP and/or its function. In some preferred embodiments, p-nitrophenyl thymidine-3'-phosphate free acid is used as a chromogenic substrate and $Mn^{++}$ (manganese cation) is used as cofactor to provide enzymatic assay systems to assess the activity of TDP and the efficacy of TDP-inhibitors.

DESCRIPTION OF THE FIGURES

FIG. 2 provides the cDNA sequence of a human TDP (SEQ ID NO:1), as well as the deduced amino acid sequence (SEQ ID NO:2) that corresponds to SEQ ID NO:1. The start codon (M) is circled in this Figure. This Figure also provides the sequences for SEQ. ID NOS:3–14.

FIG. 4 provides results of expression and purification of recombinant TDP mutants. The contents of the lanes in the gel are indicated in the Figure.

DESCRIPTION OF THE INVENTION

Figure 1:
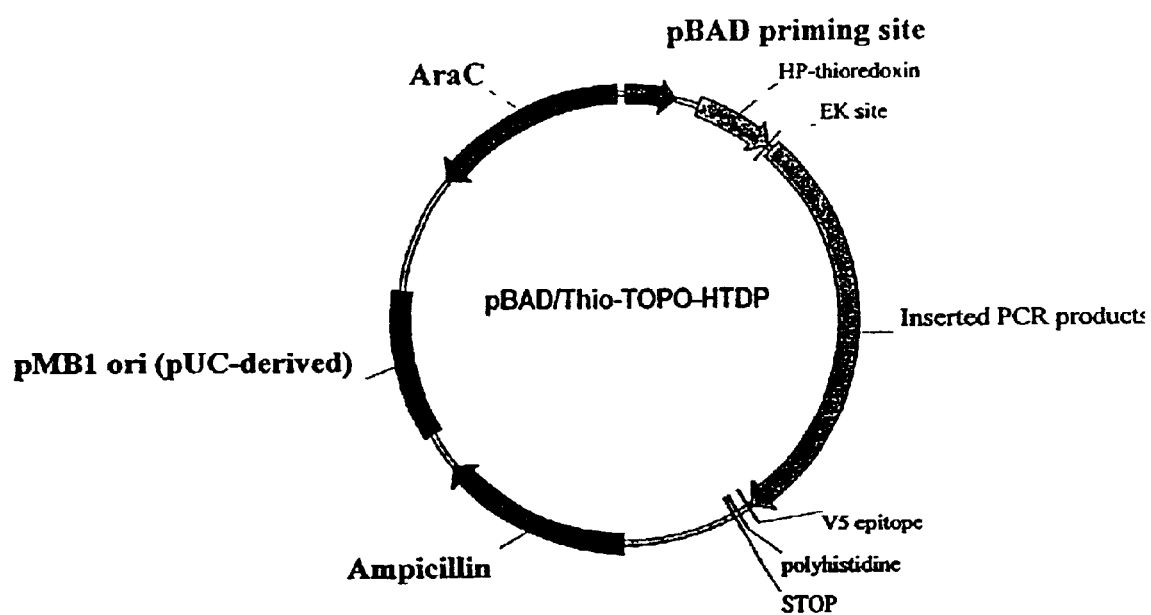
FIG. 1 provides a plasmid map used to produce high-level recombinant TDP in an *E. coli* expression system.

The present invention provides human tyrosine-DNA phosphodiesterases (TDPs). In particular, the present invention provides novel recombinant nucleic acids and proteins, including mutant TDPs, vectors, and TDP-producing cells, as well as co-factors for enzyme activity. The present invention further provides methods for high through-put enzymatic assay systems utilizing the TDPs of the present invention.

Human tyrosyl-DNA phosphodiesterase is a recently identified enzyme with a molecular weight of about 65 kDa that was shown to play a role in resolving the cytotoxic topo I-DNA complexes formed in the presence of camptothecin. In eukaryotic cells, DNA topoisomerase I is an essential enzyme that relaxes DNA supercoiling and relieves torsional strain of DNA during replication, DNA repair and transcription processes. TDP cleaves the phosphodiester bond linking the active site tyrosine residue of topo I with 3'-terminus of DNA in the topo I-DNA complexes. In *S. cerevisiae*, it has been shown that a mutation in the TDP gene inactivates the phosphodiesterase activity of gene product encoded and confers an increased sensitivity to cytotoxicity caused by camptothecin (Pouliot et al., Science 286:552–555 [1999]).

In 1996, it was first noted that tyrosyl-DNA phosphodiesterase has an activity that specifically cleaves the phosphodiester bond in topo I-DNA complexes (Yang et al., Proc. Natl. Acad. Sci., 93:11534–11539 [1996]). Subsequently, the gene encoding tyrosyl-DNA phosphodiesterase was isolated from *S. cerevisiae* (Pouliot et al., supra). In addition, TDP gene homologs have recently been identified for several other species, including *Drosophila melanogaster*, *Caenorhabditis elegans*, and *Schizosaccharomyces pombe* (Pouliot et al., supra). In Drosophila, expression of TDP gene, glaikit (gkt), was ubiquitous at the earliest stage of embryonic development, but by the time neuroblasts were found to be delaminating, gkt expression became limited to neuroblasts and a few ganglion mother cells in the newly formed central nervous system (CNS) (Dunlop et al., Mech. Develop., 96:133–136 [2000]). ClustalW analysis of protein sequences deduced from all known TDP DNA sequences to date has revealed two conserved sequence motifs of -W-L-L-T-S-A-N-L-S-K-A-A-W-G-(SEQ ID NO:15) and -Y-E-A-G-V-L-(SEQ ID NO:16), respectively (Interthal et al., Proc. Natl. Acad. Sci., early edition 211429198). Tyrosyl-DNA phosphodiesterases that have been identified to date from various species have similar molecular weights (i.e., around 60–65 kDa). As the TDP gene appears to be evolutionarily conserved between greatly differing organisms, it is contemplated that TDP is responsible for a unique but essential function.

Topoisomerases

In contrast to topoisomerase II (topo II), topoisomerase I (topo I) makes only single-stranded breaks in DNA (Champoux, *Mechanistic Aspects of Type-I Topoisomerase*, Cold Spring Harbor Laboratory, Cold Spring Harbor [1990]; Chen and Liu, Annu. Rev. Pharmacol. Toxicol., 94, 194–218 [1994]; Pommier et al., Biochim. Biophys. Acta, 1400, 83–105 [1998]; and Kjeldsen et al., J. Mol. Biol., 228:1025–1030 [1992]). The topo I-catalyzed reaction can be divided into four steps:

1) binding of topo-I to its substrate (i.e., DNA);
2) cleaving double-stranded DNA on one strand via a reversible trans-esterification reaction, in which the 5' oxygen of a phosphodiester bond is attacked by the hydroxy group on the active site tyrosine residue, thus covalently linking the DNA to topo I and forming a catalytic intermediate complex;
3) the cleaved DNA strand passes through the other intact DNA strand at the break point; and
4) re-ligation of the DNA ends in the cleaved strand.

The phosphodiester bond formed at step 2 between topo I and DNA is energy-rich and unstable in nature, thereby ensuring proper release of topo I from the catalytic intermediate and resealing of DNA ends at breakpoints during normal biological processes (See, Hertzberg et al., in Potemsil et al. (eds.), *DNA Topoisomerase in Cancer*, Oxford University Press, NY [1991], pages 103–120).

Accumulation of topo I-linked DNA breaks occurs in vivo when topo I acts on damaged DNA containing lesions such as thymine dimers and mismatched base pairs or when topo I is inhibited by camptothecin or its derivatives (Kingsbury et al., J. Med. Chem., 34:98–107 [1991]). As a consequence, accumulation of topo I-DNA covalent complexes leads to DNA damage-induced cell death/apoptosis in vivo.

Camptothecin and Topoisomerase Function

Camptothecin (CPT), a plant alkaloid originally isolated by Wani and Wall in 1966, inhibits both the cleavage and religation of eukaryotic DNA topoisomerase I (Kjeldscen et al., J. Mol. Biol., 228:1025 [1992]). CPT arrests the topo I-DNA covalent complex (i.e., the catalytic intermediate described above), and thus prevents the DNA nicks resulted from topo I enzymatic attack from undergoing re-ligation. Therefore, treatment of cancer cells with camptothecin and analogs results in inhibition of DNA replication, chromosomal fragmentation, and cell cycle arrest at G1 and G2 phase, and eventually cell programmed death (Del Bino et al., Cancer Res., 50:5746–5750 [1990]). However, the clinical utility of camptothecin, has been markedly diminished, due to its poor solubility and toxicity (non-mechanism related) and adverse effects (Gottlieb et al., Cancer Chemo. Ther. Rep., 54:461–470 [1970]). Fortunately, more water soluble derivatives of camptothecin (i.e., topotecan (10-hydroxy-9-dimethylaminomethyl-camptothecin) and irinotecan CPT-11,7-ethyl-10-(4-[1-piperidino]-1-piperidino) carbonyl-oxycamptothecin) have been designed and developed to form a new class of cancer chemotherapeutic agents. These compounds exhibit broad spectra of anti-tumor activity and have shown efficacy against solid tumors including colon, ovarian, and lung cancer. Specifically, these compounds have been used as second-line therapy for treatment of patients with untreated metastatic colorectal cancers and those with recurrent epithelial ovarian cancers that are refractory to fluoropyrimidines, or relapsed small lung cancers. However, drug resistance to topotecan and irinotecan due to various mutations in topo I, and dose-related toxicity such as diarrhea and granulocytopenia, have limited the use of this new class of chemotherapeutic agents.

Currently, to overcome drug resistance to topotecan and irinotecan, medicinal chemists focus their efforts in the design of new camptothecin derivatives. In the absence of an x-ray crystal structure of ternary complex of topoisomerase I and DNA containing a bound CPT molecule, reliance is placed on molecular modeling of the complex to predict critical interactions between CPT and the enzyme to design new CPT analogs (Fan et al., J. Med. Chem., 41:2216–2226 [1998]). For example, it was the successful development of topotecan and irinotecan as anti-tumor agents that provided the proof that topo I is a target for cancer treatment. The successful development of topotecan and irinotecan as anti-tumor agents also suggests there could exist other critical points for therapeutic intervention in this pathway. Indeed, as described in greater detail herein, inhibition of other enzymes in the same pathway (e.g., TDP) are contemplated to provide improved methods and results in cancer and other therapies.

It is contemplated that the phosphodiesterase activity of TDP will find use in reducing the detrimental effects of camptothecins and its derivatives. Thus, the present invention has been developed to take advantage of this opportunity to utilize this pathway to identify and/or characterize therapeutically useful compounds.

The present invention provides methods and compositions suitable for the development, identification, and/or characterization of compounds that are capable of modulating the activity of TDP. In particular, the present invention provides means to identify and characterize compounds that are suitable for inhibiting TDP activity in vivo and in vitro.

Definitions

To facilitate understanding of the invention, a number of terms are defined below.

As used herein, the terms "tyrosine-DNA phosphodiesterase" and "TDP" refer to a protein that is encoded by a tyrosine-DNA phosphodiesterase gene sequence or to a protein. In addition, the terms refer to enzymes that cleave the phosphodiester bond linking the active site tyrosine residue of topoisomerase I with 3'-terminus of DNA in topo I-DNA complexes.

A "variant" of human TDP as used herein, refers to an amino acid sequence that is altered by one or more amino acids. The variant may have "conservative" changes, wherein a substituted amino acid has similar structural or chemical properties, (e.g., replacement of leucine with isoleucine). More rarely, a variant may have "nonconservative" changes (e.g., replacement of a glycine with a tryptophan). Similar minor variations may also include amino acid deletions or insertions, or both.

The term "biologically active," as used herein, refers to a protein or other biologically active molecules having structural, regulatory, or biochemical functions of a naturally occurring molecule. Likewise, "immunologically active" refers to the capability of the natural, recombinant, or synthetic human TDP, or any oligopeptide or polynucleotide thereof, to induce a specific immune response in appropriate animals or cells and to bind with specific antibodies.

The term "agonist," as used herein, refers to a molecule which, when bound to human TDP, causes a change in human TDP, which modulates the activity of human TDP. Agonists may include proteins, nucleic acids, carbohydrates, or any other molecules that bind or interact with human TDP.

The terms "antagonist" or "inhibitor," as used herein, refer to a molecule which, when bound to human TDP, blocks or modulates the biological or immunological activity of human TDP. Antagonists and inhibitors may include proteins, nucleic acids, carbohydrates, or any other molecules that bind or interact with human TDP.

The term "modulate," as used herein, refers to a change or an alteration in the biological activity of human TDP. Modulation may be an increase or a decrease in protein activity, a change in binding characteristics, or any other change in the biological, functional, or immunological properties of human TDP.

The term "derivative," as used herein, refers to the chemical modification of a nucleic acid encoding human TDP, or the encoded human TDP. Illustrative of such modifications would be replacement of hydrogen by an alkyl, acyl, or amino group. A nucleic acid derivative would encode a polypeptide that retains essential biological characteristics of the natural molecule.

The term "gene" refers to a nucleic acid (e.g., DNA) sequence that comprises coding sequences necessary for the production of a polypeptide or precursor (e.g., TDP). The polypeptide can be encoded by a full length coding sequence or by any portion of the coding sequence so long as the desired activity or functional properties (e.g., enzymatic activity, ligand binding, signal transduction, etc.) of the full-length or fragment are retained. The term also encompasses the coding region of a structural gene and the sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In particular, the term "TDP gene" (or "TDP") encompasses both full-length TDP nucleotide sequence (i.e., contained in SEQ ID NO:1) and fragments of the TDP nucleotide sequence, such as SEQ ID NOS:7, 9, 11, and 13, as well as other domains within the full-length TDP nucleotide sequence. Furthermore, the terms "TDP nucleotide sequence" or "TDP polynucleotide sequence" encompasses DNA, cDNA, and RNA (e.g., mRNA) sequences. In preferred embodiments, these sequences encode the amino acid sequences set forth in SEQ ID NOS:2, 8, 10, 12 and 14.

Where "amino acid sequence" is recited herein to refer to the order of amino acids along a polypeptide chain. "Amino acid sequence" and like terms, such as "polypeptide" or "protein" are not meant to limit the amino acid sequence to the complete, native amino acid sequence associated with the recited protein molecule.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

The term "wild-type" refers to a gene or gene product that has the characteristics of that gene or gene product when isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product that displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

DNA molecules are said to have "5' ends" and "3' ends" because mononucleotides are reacted to make oligonucleotides or polynucleotides in a manner such that the 5' phosphate of one mononucleotide pentose ring is attached to the 3' oxygen of its neighbor in one direction via a phosphodiester linkage. Therefore, an end of an oligonucleotides or polynucleotide, referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide or polynucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements which direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

As used herein, the terms "an oligonucleotide having a nucleotide sequence encoding a gene" and "polynucleotide having a nucleotide sequence encoding a gene," means a nucleic acid sequence comprising the coding region of a gene or in other words the nucleic acid sequence that encodes a gene product. The coding region may be present in either a cDNA, genomic DNA or RNA form. When present in a DNA form, the oligonucleotide or polynucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

As used herein, the term "vector" is used in reference to nucleic acid molecules that transfer DNA segment(s) from one cell to another. The term "vehicle" is sometimes used interchangeably with "vector."

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes include a promoter, optionally an operator sequence, a ribosome binding site and possibly other sequences. Eukaryotic cells are known to utilize promoters, enhancers, and termination and polyadenylation signals.

As used herein, the term "regulatory element" refers to a genetic element that controls some aspect of the expression of nucleic acid sequences. For example, a promoter is a regulatory element that facilitates the initiation of transcription of an operably linked coding region. Other regulatory elements are splicing signals, polyadenylation signals, termination signals, etc. (defined infra).

Transcriptional control signals in eukaryotes comprise "promoter" and "enhancer" elements. Promoters and enhancers consist of short arrays of DNA sequences that interact specifically with cellular proteins involved in transcription (Maniatis et al., Science 236:1237 [1987]). Promoter and enhancer elements have been isolated from a variety of eukaryotic sources including genes in yeast, insect and mammalian cells and viruses (analogous control elements, i.e., promoters, are also found in prokaryote). The selection of a particular promoter and enhancer depends on what cell type is to be used to express the protein of interest. Some eukaryotic promoters and enhancers have a broad host range while others are functional in a limited subset of cell types (for review see, Voss et al., Trends Biochem. Sci., 11:287 [1986]; and T. Maniatis et al., supra). For example, the SV40 early gene enhancer is very active in a wide variety of cell types from many mammalian species and has been widely used for the expression of proteins in mammalian cells (R. Dijkema et al., EMBO J. 4:761 [1985]). Two other examples of promoter/enhancer elements active in a broad range of mammalian cell types are those from the human elongation factor 1α gene (Uetsuki et al., J. Biol. Chem., 264:5791 [1989]; D. W. Kim et al., Gene 91:217 [1990]; and Mizushima and Nagata, Nucl. Acids. Res., 18:5322 [1990]) and the long terminal repeats of the Rous sarcoma virus (Gorman et al., Proc. Natl. Acad. Sci. USA 79:6777 [1982]) and the human cytomegalovirus (Boshart et al., Cell 41:521 [1985]).

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length. The term "poly A site" or "poly A sequence" as used herein denotes a DNA sequence that directs both the termination and polyadenylation of the nascent RNA transcript. Efficient polyadenylation of the recombinant transcript is desirable as transcripts lacking a poly A tail are unstable and are rapidly degraded. The poly A signal utilized in an expression vector may be "heterologous" or "endogenous." An endogenous poly A signal is one that is found naturally at the 3' end of the coding region of a given gene in the genome. A heterologous poly A signal is one that is one that is isolated from one gene and placed 3' of another gene. A commonly used heterologous poly A signal is the SV40 poly A signal. The SV40 poly A signal is contained on a 237 bp BamHI/BclI restriction fragment and directs both termination and polyadenylation (Sambrook, supra, at 16.6–16.7).

The term "promoter/enhancer" denotes a segment of DNA which contains sequences capable of providing both promoter and enhancer functions (for example, the long terminal repeats of retroviruses contain both promoter and enhancer functions). The enhancer/promoter may be "endogenous" or "exogenous" or "heterologous." An endogenous enhancer/promoter is one that is naturally linked with a given gene in the genome. An exogenous (heterologous) enhancer/promoter is one that is placed in juxtaposition to a gene by means of genetic manipulation (i.e., molecular biological techniques).

The presence of "splicing signals" on an expression vector often results in higher levels of expression of the recombinant transcript. Splicing signals mediate the removal of introns from the primary RNA transcript and consist of a splice donor and acceptor site (Sambrook et al., Molecular Cloning: A Laboratory Manual, 2nd ed., Cold Spring Harbor Laboratory Press, New York [1989], pp. 16.7–16.8). A commonly used splice donor and acceptor site is the splice junction from the 16S RNA of SV40.

Efficient expression of recombinant DNA sequences in eukaryotic cells requires signals directing the efficient termination and polyadenylation of the resulting transcript. Transcription termination signals are generally found downstream of the polyadenylation signal and are a few hundred nucleotides in length. The term "poly A site" or "poly A sequence" as used herein denotes a DNA sequence that directs both the termination and polyadenylation of the nascent RNA transcript. Efficient polyadenylation of the recombinant transcript is desirable as transcripts lacking a poly A tail are unstable and are rapidly degraded. The poly A signal utilized in an expression vector may be "heterologous" or "endogenous." An endogenous poly A signal is one that is found naturally at the 3' end of the coding region of a given gene in the genome. A heterologous poly A signal is one that is isolated from one gene and placed 3' of another gene. A commonly used heterologous poly A signal is the SV40 poly A signal. The SV40 poly A signal is contained on a 237 bp BamHI/BclI restriction fragment and directs both termination and polyadenylation (Sambrook, supra, at 16.6–16.7). This 237 bp fragment is contained within a 671 bp BamHI/PstI restriction fragment.

The terms "selectable marker" or "selectable gene product" as used herein refer to the use of a gene that encodes an enzymatic activity that confers resistance to an antibiotic or drug upon the cell in which the selectable marker is expressed. Selectable markers may be "dominant"; a dominant selectable marker encodes an enzymatic activity that can be detected in any mammalian cell line. Examples of dominant selectable markers include the bacterial aminoglycoside 3' phosphotransferase gene (also referred to as the neo gene) which confers resistance to the drug G418 in mammalian cells, the bacterial hygromycin G phosphotransferase (hyg) gene which confers resistance to the antibiotic hygromycin and the bacterial xanthine-guanine phosphoribosyl transferase gene (also referred to as the gpt gene) which confers the ability to grow in the presence of mycophenolic acid. Other selectable markers are not dominant in that their use is must generally be in conjunction with a cell line that lacks the relevant enzyme activity. Examples of non-dominant selectable markers include the thymidine kinase (tk) gene that is used in conjunction with TK$^-$ cell lines, the carbamoyl-phosphate synthetase-aspartate transcarbamoylase-dihydroorotase (CAD) gene that is used in conjunction with CAD-deficient cells and the mammalian hypoxanthine-guanine phosphoribosyl transferase (hprt) gene that is used in conjunction with HPRT$^-$ cell lines. A review of the use of selectable markers in mammalian cell lines is provided in Sambrook et al., supra at pp.16.9–16.15. It is noted that some selectable markers can be amplified and therefore can be used as amplifiable markers (e.g., the CAD gene).

Eukaryotic expression vectors may also contain "viral replicons" or "viral origins of replication." Viral replicons are viral DNA sequences that allow for the extrachromosomal replication of a vector in a host cell expressing the appropriate replication factors. Vectors which contain either the SV40 or polyoma virus origin of replication replicate to high copy number (up to $10^4$ copies/cell) in cells that express the appropriate viral T antigen. Vectors which contain the replicons from bovine papillomavirus or Epstein-Barr virus replicate extrachromosomally at low copy number (~100 copies/cell).

As used herein, the terms "complementary" or "complementarity" are used in reference to polynucleotides (i.e., a sequence of nucleotides) related by the base-pairing rules. For example, for the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods which depend upon binding between nucleic acids.

The term "homology" refers to a degree of complementarity. There may be partial homology or complete homology (i.e., identity). A partially complementary sequence is one that at least partially inhibits a completely complementary sequence from hybridizing to a target nucleic acid is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target which lacks even a partial degree of complementarity (e.g., less than about 30% identity); in the absence of non-specific binding the probe will not hybridize to the second non-complementary target.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions which promote hybridization under conditions of high stringency (e.g., increasing the temperature of the hybridization and/or wash steps, the use of formamide in the hybridization solution, etc.).

When used in reference to a double-stranded nucleic acid sequence such as a cDNA or genomic clone, the term "substantially homologous" refers to any probe which can hybridize to either or both strands of the double-stranded nucleic acid sequence under conditions of low stringency as described above.

A gene may produce multiple RNA species which are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

When used in reference to a single-stranded nucleic acid sequence, the term "substantially homologous" refers to any probe which can hybridize (i.e., it is the complement of) the single-stranded nucleic acid sequence under conditions of low stringency as described above.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids.

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% \text{ G+C})$, when a nucleic acid is in aqueous solution at 1 M NaCl (See e.g., Anderson and Young, "Quantitative Filter Hybridization," in *Nucleic Acid Hybridization* [1985]). Other references include more sophisticated computations which take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. With "high stringency" conditions, nucleic acid base pairing will occur only between nucleic acid fragments that have a high frequency of complementary base sequences. Thus, conditions of "weak" or "low" stringency are often required with nucleic acids that are derived from organisms that are genetically diverse, as the frequency of complementary sequences is usually less.

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

The term "amplification" or "gene amplification" as used herein refers to a process by which specific DNA sequences are disproportionately replicated such that the amplified gene becomes present in a higher copy number than was initially present in the genome. Gene amplification occurs naturally during development in particular genes such as the amplification of ribosomal genes in amphibian oocytes. Gene amplification may be induced by treating cultured cells with drugs. An example of drug-induced amplification is the methotrexate-induced amplification of the endogenous dhfr gene in mammalian cells (Schmike et al. Science 202:1051 [1978]). Selection of cells by growth in the presence of a drug (e.g., an inhibitor of an inhibitable enzyme) may result in the amplification of either the endogenous gene encoding the gene product required for growth in the presence of the drug or by amplification of exogenous (i.e., input) sequences encoding this gene product, or both.

The term "co-amplification" as used herein refers to the introduction into a single cell of an amplifiable marker in conjunction with other gene sequences (comprising one or more non-selectable genes such as those contained within an expression vector) and the application of appropriate selective pressure such that the cell amplifies both the amplifiable marker and the other, non-selectable gene sequences. The amplifiable marker may be physically linked to the other gene sequences or alternatively two separate pieces of DNA, one containing the amplifiable marker and the other containing the non-selectable marker, may be introduced into the same cell.

The term "amplifiable marker," "amplifiable gene" or "amplification vector" is used herein to refer to a gene or a vector encoding a gene which permits the amplification of that gene under appropriate growth conditions. Vectors encoding the dihydrofolate reductase (dhfr) gene can be introduced into appropriate cell lines (typically a dhfr⁻ cell) and grown in the presence of increasing concentrations of the DHFR inhibitor methotrexate to select for cells which have amplified the dhfr gene. The adenosine deaminase (ada) gene has been used in analogous fashion to allow the amplification of ada gene sequences in cells selected for growth in the presence of ADA inhibitors such as 2'-deoxycoformycin. Examples of other genes which can be used as amplifiable markers in mammalian cells include the CAD gene (inhibitor: N-phosphonoacetyl-L-aspartic acid), the ornithine decarboxylase gene (inhibitor: difluoromethylornithine in medium lacking putrescine), and the asparagine synthetase gene (inhibitors: albizziin or β-aspartyl hydroxamate in asparagine-free medium) (See e.g., Kaufman, Meth. Enzymol., 185:537 [1990], for a review).

Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Qβ replicase, MDV-1 RNA is the specific template for the replicase (Kacian et al., Proc. Natl. Acad. Sci. USA 69:3038 [1972]). Other nucleic acid will not be replicated by this amplification enzyme. Similarly, in the case of T7 RNA polymerase, this amplification enzyme has a stringent specificity for its own promoters (Chamberlin et al., Nature 228:227 [1970]). In the case of T4 DNA ligase, the enzyme will not ligate the two oligonucleotides or polynucleotides, where there is a mismatch between the oligonucleotide or polynucleotide substrate and the template at the ligation junction (Wu and Wallace, Genomics 4:560 [1989]). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (Erlich (ed.), *PCR Technology*, Stockton Press [1989]).

As used herein, the term "amplifiable nucleic acid" is used in reference to nucleic acids which may be amplified by any amplification method. It is contemplated that "amplifiable nucleic acid" will usually comprise "sample template."

As used herein, the term "sample template" refers to nucleic acid originating from a sample which is analyzed for the presence of "target" (defined below). In contrast, "background template" is used in reference to nucleic acid other than sample template which may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The exact lengths of the primers will depend on many factors, including temperature, source of primer and the use of the method. Generally, primers are selected to be long enough to prime an extension product in the presence of the inducing agent.

As used herein, the term "probe" refers to an oligonucleotide (i.e., a sequence of nucleotides), whether occurring naturally as in a purified restriction digest or produced synthetically, recombinantly or by PCR amplification, which is capable of hybridizing to another oligonucleotide of interest. A probe may be single-stranded or double-stranded. Probes are useful in the detection, identification and isolation of particular gene sequences. It is contemplated that any probe used in the present invention will be labelled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the term "target," when used in reference to the polymerase chain reaction, refers to the region of nucleic acid bounded by the primers used for polymerase chain reaction. Thus, the "target" is sought to be sorted out from other nucleic acid sequences. A "segment" is defined as a region of nucleic acid within the target sequence.

As used herein, the term "polymerase chain reaction" ("PCR") refers to the methods of U.S. Pat. Nos. 4,683,195 4,683,202, and 4,965,188, hereby incorporated by reference, which describe methods for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified".

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process itself are, themselves, efficient templates for subsequent PCR amplifications.

As used herein, the terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

As used herein, the term "amplification reagents" refers to those reagents (deoxyribonucleotide triphosphates, buffer, etc.), needed for amplification except for primers, nucleic acid template and the amplification enzyme. Typically, amplification reagents along with other reaction components are placed and contained in a reaction vessel (test tube, microwell, etc.).

As used herein, the term "RT-PCR" refers to the replication and amplification of RNA sequences. In this method, reverse transcription is coupled to PCR, most often using a one enzyme procedure in which a thermostable polymerase is employed, as described in U.S. Pat. No. 5,322,770, herein incorporated by reference. In RT-PCR, the RNA template is converted to cDNA due to the reverse transcriptase activity of the polymerase, and then amplified using the polymerizing activity of the polymerase (i.e., as in other PCR methods).

As used herein, the terms "restriction endonucleases" and "restriction enzymes" refer to bacterial enzymes, each of which cut double-stranded DNA at or near a specific nucleotide sequence.

As used herein, the term "antisense" is used in reference to RNA sequences which are complementary to a specific RNA sequence (e.g., mRNA). Included within this definition are antisense RNA ("asRNA") molecules involved in gene regulation by bacteria. Antisense RNA may be produced by any method, including synthesis by splicing the gene(s) of interest in a reverse orientation to a viral promoter which permits the synthesis of a coding strand. Once introduced into an embryo, this transcribed strand combines with natural mRNA produced by the embryo to form duplexes. These duplexes then block either the further transcription of the mRNA or its translation. In this manner, mutant phenotypes may be generated. The term "antisense strand" is used in reference to a nucleic acid strand that is complementary to the "sense" strand. The designation (−) (i.e., "negative") is sometimes used in reference to the antisense strand, with the designation (+) sometimes used in reference to the sense (i.e., "positive") strand.

As used herein the term "coding region" when used in reference to structural gene refers to the nucleotide sequences which encode the amino acids found in the nascent polypeptide as a result of translation of a mRNA molecule. The coding region is bounded, in eukaryotes, on the 5' side by the nucleotide triplet "ATG" which encodes the initiator methionine and on the 3' side by one of the three triplets which specify stop codons (i.e., TAA, TAG, TGA).

As used herein, the term "structural gene" refers to a DNA sequence coding for RNA or a protein. In contrast, "regulatory genes" are structural genes which encode products which control the expression of other genes (e.g., transcription factors).

As used herein, the term "polyA$^+$ RNA" refers to RNA molecules having a stretch of adenine nucleotides at the 3' end. This polyadenine stretch is also referred to as a "poly-A tail." Eukaryotic mRNA molecules contain poly-A tails and are referred to as polyA$^+$ RNA.

The terms "in operable combination," "in operable order," and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "isolated" when used in relation to a nucleic acid, as in "an isolated oligonucleotide" or "isolated polynucleotide" refers to a nucleic acid sequence that is identified and separated from at least one contaminant nucleic acid with which it is ordinarily associated in its natural source. Isolated nucleic acid is such present in a form or setting that is different from that in which it is found in nature. In contrast, non-isolated nucleic acids as nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNA s which encode a multitude of proteins. However, isolated nucleic acid encoding a mammalian (e.g., human) TDP protein includes, by way of example, such nucleic acid in cells ordinarily expressing a TDP protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may be single-stranded), but may contain both the sense and anti-sense strands (i.e., the oligonucleotide or polynucleotide may be double-stranded).

As used herein, the term "purified" or "to purify" refers to the removal of contaminants from a sample. For example, anti-TDP antibodies are purified by removal of contaminating non-immunoglobulin proteins; they are also purified by the removal of immunoglobulin that does not bind TDP. The removal of non-immunoglobulin proteins and/or the removal of immunoglobulins that do not bind TDP results in an increase in the percent of TDP-reactive immunoglobulins in the sample. In another example, recombinant TDP polypeptides are expressed in bacterial host cells and the polypeptides are purified by the removal of host cell proteins; the percent of recombinant TDP polypeptides is thereby increased in the sample.

The term "recombinant DNA molecule" as used herein refers to a DNA molecule comprising segments of DNA joined together by means of molecular biological techniques.

The term "recombinant protein" or "recombinant polypeptide" as used herein refers to a protein molecule which is expressed from a recombinant DNA molecule.

The term "native protein" as used herein to indicate that a protein does not contain amino acid residues encoded by vector sequences; that is the native protein contains only those amino acids found in the protein as it occurs in nature. A native protein may be produced by recombinant means or may be isolated from a naturally occurring source.

As used herein the term "portion" when in reference to a protein (as in "a portion of a given protein") refers to fragments of that protein. The fragments may range in size from four amino acid residues to the entire amino acid sequence minus one amino acid.

As used herein, the term "fusion protein" refers to a chimeric protein containing the protein of interest (e.g., human TDP and fragments thereof) joined to an exogenous protein fragment (the fusion partner which consists of a non-TDP protein). The fusion partner may enhance solubility of the TDP protein as expressed in a host cell, may provide an affinity tag to allow purification of the recombinant fusion protein from the host cell or culture supernatant, or both. If desired, the fusion protein may be removed from the protein of interest (i.e., TDP protein or fragments thereof) by a variety of enzymatic or chemical means known to the art.

The term "Southern blot," refers to the analysis of DNA on agarose or acrylamide gels to fractionate the DNA according to size followed by transfer of the DNA from the gel to a solid support, such as nitrocellulose or a nylon membrane. The immobilized DNA is then probed with a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (J. Sambrook et al., *Molecular Cloning: A Laboratory Manual*, Cold Spring Harbor Press, NY, pp 9.31–9.58 [1989]).

The term "Northern blot," as used herein refers to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (Sambrook et al., supra, pp 7.39–7.52 [1989]).

The term "Western blot" refers to the analysis of protein (s) (or polypeptides) immobilized onto a support such as nitrocellulose or a membrane. The proteins are run on acrylamide gels to separate the proteins, followed by transfer of the protein from the gel to a solid support, such as nitrocellulose or a nylon membrane. The immobilized proteins are then exposed to antibodies with reactivity against an antigen of interest. The binding of the antibodies may be detected by various methods, including the use of radiolabelled antibodies.

The term "antigenic determinant" as used herein refers to that portion of an antigen that makes contact with a particular antibody (i.e., an epitope). When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the "immunogen" used to elicit the immune response) for binding to an antibody.

The terms "specific binding" or "specifically binding" when used in reference to the interaction of an antibody and a protein or peptide means that the interaction is dependent upon the presence of a particular structure (i.e., the antigenic determinant or epitope) on the protein; in other words the antibody is recognizing and binding to a specific protein structure rather than to proteins in general. For example, if an antibody is specific for epitope "A," the presence of a protein containing epitope A (or free, unlabelled A) in a reaction containing labelled "A" and the antibody will reduce the amount of labelled A bound to the antibody.

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "stable transfection" or "stably transfected" refers to the introduction and integration of foreign DNA into the genome of the transfected cell. The term "stable transfectant" refers to a cell which has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells which have taken up foreign DNA but have failed to integrate this DNA.

The term "calcium phosphate co-precipitation" refers to a technique for the introduction of nucleic acids into a cell. The uptake of nucleic acids by cells is enhanced when the nucleic acid is presented as a calcium phosphate-nucleic acid co-precipitate. The original technique of Graham and van der Eb (Graham and van der Eb, Virol., 52:456 [1973]), has been modified by several groups to optimize conditions for particular types of cells. The art is well aware of these numerous modifications.

As used herein, the term "cell culture" refers to any in vitro culture of cells. Included within this term are continuous cell lines (e.g., with an immortal phenotype), primary cell cultures, finite cell lines (e.g., non-transformed cells), and any other cell population maintained in vitro.

The term "compound" refers to any chemical entity, pharmaceutical, drug, and the like that can be used to treat or prevent a disease, illness, sickness, or disorder of bodily function. Compounds comprise both known and potential therapeutic compounds. A compound can be determined to be therapeutic by screening using the screening methods of the present invention. A "known therapeutic compound" refers to a therapeutic compound that has been shown (e.g., through animal trials or prior experience with administration to humans) to be effective in such treatment. In other words, a known therapeutic compound is not limited to a compound efficacious in the treatment of cancer.

The term "test compound" refers to any chemical entity, pharmaceutical, drug, and the like that can be used to treat or prevent a disease, illness, sickness, or disorder of bodily function. Test compounds comprise both known and potential therapeutic compounds. A test compound can be determined to be therapeutic by screening using the screening methods of the present invention. A "known therapeutic compound" refers to a therapeutic compound that has been shown (e.g., through animal trials or prior experience with administration to humans) to be effective in such treatment or prevention. In other words, a known therapeutic compound is not limited to a compound efficacious in the treatment of TDP instability or inactivity in animals (e.g., greater sensitivity to ultraviolet radiation).

A compound is said to be "in a form suitable for administration to the mammal" when the compound may be administered to a mammal by any desired route (e.g., oral, intravenous, subcutaneous, intramuscular, etc.) and the compound or its active metabolites appears in the blood and/or the desired site within or on the mammal. Administration of a compound to a pregnant female may result in delivery of the compound to the fetuses of the pregnant animal.

A "composition comprising a given polynucleotide sequence" as used herein refers broadly to any composition containing the given polynucleotide sequence. The composition may comprise an aqueous solution. Compositions comprising polynucleotide sequences encoding human TDP (e.g., SEQ ID NO:1) or fragments thereof (e.g., SEQ ID NOS:1, 7, 9, 11, 13, and suitable fragments thereof) may be employed as hybridization probes. In this case, the human TDP-encoding polynucleotide sequences are typically employed in an aqueous solution containing salts (e.g., NaCl), detergents (e.g., SDS) and other components (e.g., Denhardt's solution, dry milk, salmon sperm DNA, etc.).

The term "sample" as used herein is used in its broadest sense. A sample suspected of containing a human chromosome or sequences associated with a human chromosome may comprise a cell, chromosomes isolated from a cell (e.g., a spread of metaphase chromosomes), genomic DNA (in solution or bound to a solid support such as for Southern blot analysis), RNA (in solution or bound to a solid support such as for Northern blot analysis), cDNA (in solution or bound to a solid support) and the like. A sample suspected of containing a protein may comprise a cell, a portion of a tissue, an extract containing one or more proteins and the like.

The term "recombinant oligonucleotide" refers to an oligonucleotide created using molecular biological manipulations, including but not limited to, the ligation of two or more oligonucleotide sequences generated by restriction enzyme digestion of a polynucleotide sequence, the synthesis of oligonucleotides (e.g., the synthesis of primers or oligonucleotides) and the like.

The term "recombinant oligonucleotide having a sequence encoding a protein operably linked to a heterologous promoter" or grammatical equivalents indicates that the coding region encoding the protein (e.g., an enzyme) has been joined to a promoter which is not the promoter naturally associated with the coding region in the genome of an organism (i.e., it is linked to an exogenous promoter). The promoter which is naturally associated or linked to a coding region in the genome is referred to as the "endogenous promoter" for that coding region.

The term "transcription unit" as used herein refers to the segment of DNA between the sites of initiation and termination of transcription and the regulatory elements necessary for the efficient initiation and termination. For example, a segment of DNA comprising an enhancer/promoter, a coding region, and a termination and polyadenylation sequence comprises a transcription unit.

The term "gene of interest" as used herein refers to the gene inserted into the polylinker of an expression vector whose expression in the cell is desired for the purpose of performing further studies on the transfected cell. The gene of interest may encode any protein whose expression is desired in the transfected cell at high levels. The gene of interest is not limited to the examples provided herein; the gene of interest may include cell surface proteins, secreted proteins, ion channels, cytoplasmic proteins, nuclear proteins (e.g., regulatory proteins), mitochondrial proteins, etc.

The terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

The terms "parent cell line" or "parental cell line" refers to a cell line prior to the addition of exogenous nucleic acid.

The term "transformed cells" refers to cells which contain exogenous DNA (i.e., heterologous DNA introduced into the cells such as the introduction of an expression vector). Terms "transformed cell" and "transfected cell" are used herein interchangeably.

The term "amplified number of copies of a vector" refers to a cell line which has incorporated an exogenous or recombinant vector and has increased the number of copies of the vector present in the cell by virtue of the process of gene amplification.

The term "amplified gene" refers to a gene present in multiple copies in a cell line by virtue of gene amplification.

A cell which contains an "endogenous gene encoding an inhibitable enzyme" refers to cell which naturally (as opposed to by virtue of recombinant DNA manipulations) contains in its genomic DNA a gene encoding an inhibitable enzyme; the coding region of this gene will be operably linked to and under the control of its endogenous promoter.

The term "active enzyme" refers to an enzyme which is functional (i.e., capable of carrying out the enzymatic function).

As used herein, the term "kit" is used in reference to a combination of reagents and other materials.

As used herein, the term "antibody" is used in reference to any immunoglobulin molecule that reacts with a specific antigen. It is intended that the term encompass any immunoglobulin (e.g., IgG, IgM, IgA, IgE, IgD, etc.) obtained from any source (e.g., humans, rodents, non-human primates, caprines, bovines, equines, ovines, etc.).

As used herein, the term "antigen" is used in reference to any substance that is capable of reacting with an antibody. It is intended that this term encompass any antigen and "immunogen" (i.e., a substance which induces the formation of antibodies). Thus, in an immunogenic reaction, antibodies are produced in response to the presence of an antigen (immunogen) or portion of an antigen.

As used herein, the terms "antigen fragment" and "portion of an antigen" are used in reference to a portion of an antigen. Antigen fragments or portions may occur in various sizes, ranging from a small percentage of the entire antigen to a large percentage, but not 100% of the antigen. However, in situations where at least a portion of an antigen is specified, it is contemplated that the entire antigen may be present. It is contemplated that antigen fragments or portions, may, but are not required to comprise an "epitope" recognized by an antibody. Antigen fragments or portions also may or may not be immunogenic.

As used herein, the term "autoantibodies" refers to antibodies that are capable of reacting against an antigenic constituent of an individual's own tissue or cells (e.g., the antibodies recognize and bind to "self" antigens).

As used herein, the term "immunoassay" is used in reference to any method in which antibodies are used in the detection of an antigen. It is contemplated that a range of immunoassay formats be encompassed by this definition, including but not limited to direct immunoassays, indirect immunoassays, and "sandwich" immunoassays." However, it is not intended that the present invention be limited to any particular format. It is contemplated that other formats, including radioimmunoassays (RIA), immunofluorescent assays (IFA), and other assay formats, including, but not limited to, variations on the ELISA, RIA and/or IFA methods will be useful in the method of the present invention.

As used herein, the term "capture antibody" refers to an antibody that is used to bind an antigen and thereby permit the recognition of the antigen by a subsequently applied antibody. For example, the capture antibody may be bound to a microtiter well and serve to bind an antigen of interest present in a sample added to the well. Another antibody (termed the "primary antibody") is then used to bind to the antigen-antibody complex, in effect to form a "sandwich" comprised of antibody-antigen-antibody. Detection of this complex can be performed by several methods. The primary antibody may be prepared with a label such as biotin, an enzyme, a fluorescent marker, or radioactivity, and may be detected directly using this label. Alternatively, a labelled "secondary antibody" or "reporter antibody" which recognizes the primary antibody may be added, forming a complex comprised of antibody-antigen-antibody-antibody. Again, appropriate reporter reagents are then added to detect the labelled antibody. Any number of additional antibodies may be added as desired. These antibodies may also be labelled with a marker, including, but not limited to an enzyme, fluorescent marker, or radioactivity.

As used herein, the term "reporter reagent" or "reporter molecule" is used in reference to compounds which are capable of detecting the presence of antibody bound to antigen. For example, a reporter reagent may be a colorimetric substance attached to an enzymatic substrate. Upon binding of antibody and antigen, the enzyme acts on its substrate and causes the production of a color. Other reporter reagents include, but are not limited to fluorogenic and radioactive compounds or molecules. This definition also encompasses the use of biotin and avidin-based compounds (e.g., including, but not limited to neutravidin and streptavidin) as part of the detection system. In one embodiment of the present invention, biotinylated antibodies may be used in the present invention in conjunction with avidin-coated solid support.

As used herein the term "signal" is used in reference to an indicator that a reaction has occurred, for example, binding of antibody to antigen. It is contemplated that signals in the form of radioactivity, fluorogenic reactions, luminscent and enzymatic reactions will be used with the present invention. The signal may be assessed quantitatively as well as qualitatively.

As used herein, the term "solid support" is used in reference to any solid material to which reagents such as antibodies, antigens, and other compounds may be attached. For example, in the ELISA method, the wells of microtiter plates often provide solid supports. Other examples of solid supports include microscope slides, coverslips, beads, particles, cell culture flasks, as well as many other items.

Experimental

The following examples are provided in order to demonstrate and further illustrate certain preferred embodiments and aspects of the present invention and are not to be construed as limiting the scope thereof.

In the experimental disclosure which follows, the following abbreviations apply: ° C. (degrees Centigrade); rpm (revolutions per minute); $H_2O$ (water); HCl (hydrochloric acid); aa (amino acid); bp (base pair); kb (kilobase pair); kD (kilodaltons); gm (grams); $\mu$g (micrograms); mg (milligrams); ng (nanograms); $\mu$l (microliters); ml (milliliters); mm (millimeters); nm (nanometers); $\mu$m (micrometer); M (molar); mM (millimolar); $\mu$M (micromolar); U (units); V (volts); MW (molecular weight); sec (seconds); min(s) (minute/minutes); hr(s) (hour/hours); $MgCl_2$ (magnesium chloride); NaCl (sodium chloride); $OD_{280}$ (optical density at 280 nm); $OD_{415}$ (optical density at 415 nm); PAGE (polyacrylamide gel electrophoresis); PBS (phosphate buffered saline [150 mM NaCl, 10 mM sodium phosphate buffer, pH 7.2]); PCR (polymerase chain reaction); RT-PCR (reverse transcription PCR); SDS (sodium dodecyl sulfate); Tris (tris(hydroxymethyl) aminomethane); w/v (weight to volume); v/v (volume to volume); Amersham Pharmacia (Amersham Pharmacia AB, Piscataway, N.J.); ICN (ICN Pharmaceuticals, Inc., Costa Mesa, Calif.); Amicon (Amicon, Inc., Beverly, Mass.); ATCC (American Type Culture Collection, Rockville, Md.); BioRad (BioRad, Hercules, Calif.); Invitrogen (Invitrogen Corp., Carlsbad, Calif.); New England Biolabs (New England Biolabs, Inc., Beverly, Mass.); Novagen (Novagen, Inc., Madison, Wis.); Sigma (Sigma Chemical Co., St. Louis, Mo.); GIBCO BRL or Gibco BRL (Gibco BRL Life Technologies, Inc., Rockville, Md.); and Stratagene (Stratagene Cloning Systems, La Jolla, Calif.).

Standard recombinant DNA and molecular cloning techniques used in the performance of the experiments described herein are well known in the art (See e.g., Sambrook et al., (eds.), *Molecular Cloning*, Cold Spring Harbor Laboratory Press, Cold Spring Harbor, N.Y. [1989]; and Ausubel et al., *Current Protocols in Molecular Biology*, Greene Publishing Association and Wiley-Interscience [1987]).

EXAMPLE 1

Isolation of Human TDP cDNA

This Example describes experiments conducted to identify and isolate human TDP cDNAs. Preliminary database searches revealed that a full-length human cDNA (National Center for Biotechnology Information Accession No. NM_018319) has substantial similarity to the sequence of yeast TDP, which was published by Pouliot et al. supra (gene YBR223c; Genbank Z36092.1). In order to validate the enzymatic activity of this human gene, the human TDP was amplified by PCR from a human cDNA pool made by reverse transcription of RNA isolated from human cultured cells (HT1080; ATCC CCL-121), as described below.

Total RNA from HT1080 cells was isolated by cell lysis with TRIZOL Reagent (Gibco BRL), followed by RNA precipitation by isopropyl alcohol. Next, the isolated RNA was used as a template for RT-PCR using the THERMO-SCRIPT RT-PCR system (Gibco BRL). Briefly, in the first step, cDNA transcripts were produced using the isolated RNA primed with oligo (dT) at 65° C. for 5 minutes and then reverse-transcribed into cDNA using the THERMO-SCRIPT™ RT-PCR system (Gibco BRL). In the second step, PCR was performed in separate tubes using either primers specific for amplification of of the fragment of TDP cDNA containing nucleotides 1–544 (i.e., the primers set forth in SEQ IDS NO:17 and 18), or primers specific for amplification of the fragment of TDP cDNA containing nucleotides 521–1827 (i.e., the primers set forth in SEQ ID NOS:19 and 20). The sequences of these primers are:

```
                                          SEQ ID NO:17
5'-cgcggatccatcacaggaaggcgattatgggagg-3'

SEQ ID NO:18
5'-atgtggagggctccagagttatactttgg-3'

SEQ ID NO:19
5'-ttaagccaaagtataactctggagccctcc-3'

SEQ ID NO:20
5'-cgcggatccacttatcaggagggcacccacatgttcccatgc-3'
```

The two PCR-amplified fragments obtained were then combined and used as templates for another PCR using SEQ ID NOS:17 and 20. All of the PCRs were performed using Taq DNA polymerase (Gibco BRL). The reaction conditions were: an initial denaturation at 94° C. for 4 minutes, followed by 30 cycles of 94° C. for 45 seconds, 55° C. for 45 seconds and 72° C. for 2 minutes, followed by final extension at 72° C. for 10 minutes.

The resulting PCR products were then cloned into the BamHI site of the cloning vector pPCIZB (Invitrogen) and sequenced using methods known in the art. The complete cDNA sequence of human TDP is provided in SEQ ID NO:1. The full-length protein encoded by this nucleic acid comprises 608 amino acids, and has the amino acid sequence set forth in SEQ ID NO:2.

EXAMPLE 2

Construction of Mutant Human TDP

This Example describes the construction of various mutant human TDPs. Deletion mutants were generated which contain deletions in either the N-terminus or C-terminus. In particular, this Example describes the construction of human TDP deletion mutants, HTDPNΔ1–39 (or "NΔ1–39"), HTDPNΔ1–174 (or "NΔ1–174"), ΔHTDPN1–39/CΔ547–608 (or "NΔ1–39/CΔ547–608"), and ΔHTDPN1–174/CΔ547–608 (or "NΔ1–174/CΔ547–608").

Briefly, different constructs were prepared using standard PCR amplifications followed by TA-ligation of the resultant PCR products into the pBAD/Thio-TOPO vector (Invitrogen; See, FIG. 1), using the methods suggested by the manufacturer. For PCR reacations, the full-length TDP cDNA was used as a template and different primer sets were used for specific variants. For example, the oligonucleotides used for HTDPNΔ1–39 deletion constructs were 5'-GCAGCAAATGAGCCCAGGTACACCTGTTCC-3' (SEQ ID NO:3) and 5'-GGAGGGCACCCACATGTTCC CATGC-3' (SEQ ID NO:4). Likewise, the oligonucleotides used for the HTDPNΔ1–174 deletion constructs were 5'-AAGTATAACTCTCGAGCCCTCCACATCAAGG-3' (SEQ ID NO:5) and 5'-GGAGGGCACCCACATGTTCC CATGC-3' (SEQ ID NO:4). For HTDPNΔ1–39/ CΔ547–608, the oligonucleotides used were 5'-GCAGCAAATGAGCCCAGGTACACCTGTTCC-3' (SEQ ID NO:3) and 5'-TGAAGGGAGGAAAAGGACCCC GAGC-3' (SEQ ID NO: 6). In addition, the oligonucleotides used for HTDPNΔ1–174/CΔ547–608 were 5'-AAGTATAACTCTCGAGCCCTCCACATCAAGG-3' (SEQ ID NO:5) and 5'-TGAAGGGAGGAAAAGGACCCC GAGC-3' (SEQ ID NO:6).

The resultant PCR products were TA-ligated into the pBAD/Thio-TOPO vector (Invitrogen), according to the manufacturer's instructions. Next, the plasmids were confirmed by restriction enzyme mapping and DNA sequencing, using methods known in the art.

Figure 3:
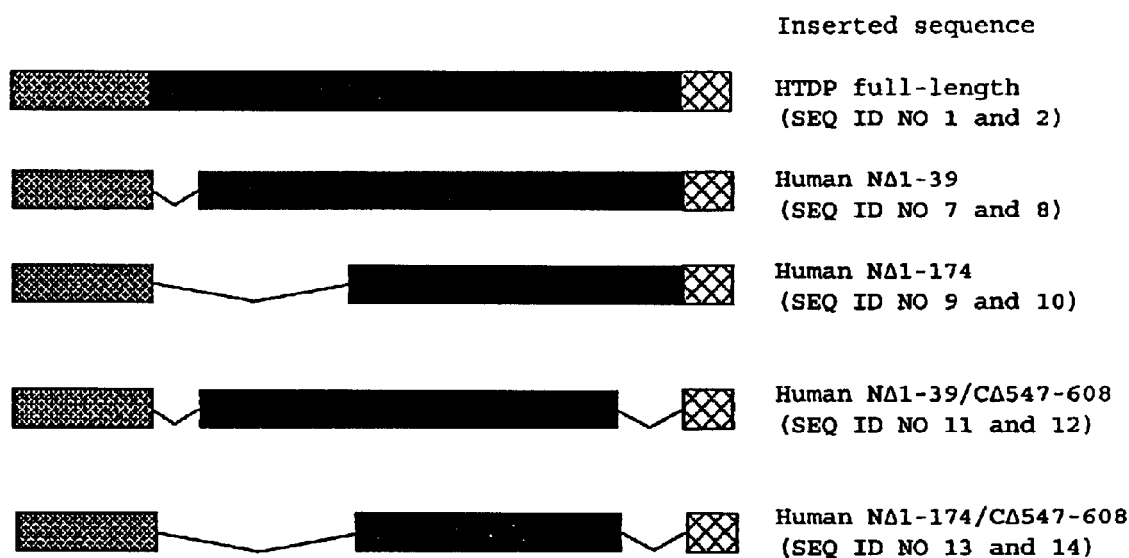
FIG. 3 provides a schematic showing recombinant TDP and TDP mutants, as well as the individual SEQ ID NOS of these proteins.
Figure 5:
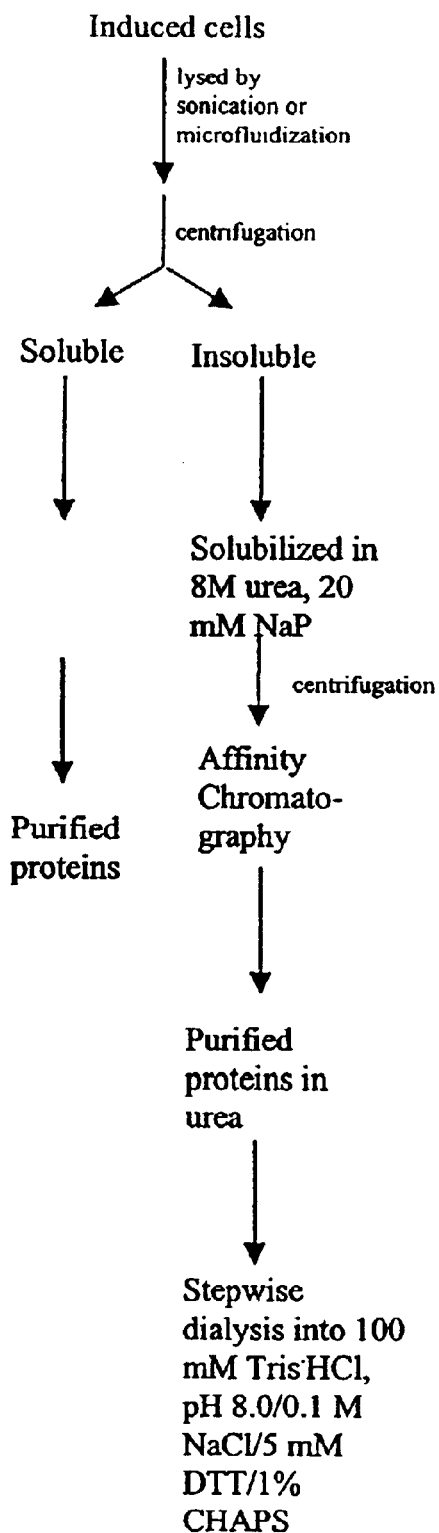
FIG. 5 provides the purification and refolding protocol utilized to prepare pure soluble and active human TDP enzyme for protein structure studies FIG. 6 provides the chemical structure of the chromogenic substrate used to detect the cleavage of DNA-topoisomerase complex by TDP.

The DNA sequence of the human TDP mutant NΔ1–39, is provided in SEQ ID NO:7. The full length protein encoded by this nucleic acid comprises 579 amino acids, and has the amino acid sequence set forth as SEQ ID NO:8. The DNA sequence of the human TDP mutant Δ1–174, is shown in SEQ ID NO:9. The full length protein encoded by this nucleic acid comprises 434 amino acids, and has the amino acid sequence set forth in SEQ ID NO:10. The DNA sequence of the human TDP mutant NΔ1–39/CΔ547–608 is set forth in SEQ ID NO: 11. The full length protein encoded by this nucleic acid comprises 507 amino acids, and has the amino acid sequence shown set forth in SEQ ID NO:12. The DNA sequence of the human TDP mutant NΔ1–174/ CΔ547–608, is set forth in SEQ ID NO: 13. The full length protein encoded by this nucleic acid comprises 372 amino acids, and has the amino acid sequence is set forth as SEQ ID NO: 14. FIG. 3 provides a schematic showing recombinant TDP and TDP mutants, as well as the individual SEQ ID NOS of these proteins.

EXAMPLE 3

Expression of Human TDP Mutants in Bacterial Cells

To express the human TDP mutants described above in bacterial cells, the pTopoBAD/Thio vector (Invitrogen) was used. This vector contains an ampicillin resistance gene, an *E. coli* replication origin, a histidine-patch thioredoxin ORF (open-reading frame), and a poly-histidine region. A DNA fragment encoding the mutant sequence (e.g., Δ1–39; SEQ ID NO: 6) was cloned into the TA cloning site of the vector.

Thus, human TDP mutant was fused to thioredoxin and this fusion polypeptide was expressed in *E. coli* (e.g., strain TOP10). Expression of this thioredoxin-hTDP fusion protein in TOP10 was induced with arabinose (i.e., 0.02% arabinose was added to the culture). The recombinant fusion polypeptide was purified from crude bacterial lysates of the induced TOP10 by affinity chromatography on a nickel chelating column using methods known in the art. Using polyacrylamide gel (SDS-PAGE; 12% gel) electrophoretic analysis of the polypeptide purified from the bacterial lysates, the molecular weight of the resultant fusion polypeptide is determined. SDS-PAGE results are shown in FIG. 4.

EXAMPLE 4

Purification of Recombinant Thioredoxin-Mutant TDP Fusion Proteins

In this Example, methods used in the purification of recombinant thioredoxin-mutant TDP fusion proteins are described.

Expression of the thioredoxin-mutant TDP fusion protein in TOP10 was induced with 0.02% arabinose added to the culture, as described in Example 3. The induced cells were pelleted and lysed in 20 mM NaP, pH 7.4, with protease inhibitors, either by sonication or by microfluidization, followed by centrifugation, in order to obtain soluble lysates and insoluble fractions.

Soluble expressed recombinant proteins were purified from the cell lysates by affinity chromatography on a nickel chelating column in the absence of urea, as known in the art. Insoluble expressed recombinant proteins were solubilized in 8 M urea/NaP, pH 7.5 for 2 hours, followed by centrifugation (12,000×g for 30 minutes) to remove any impurities. The urea-solubilized lysates were then subjected to affinity chromatography on a nickel chelating column in the presence of 8 M urea, as known in the art.

The purified proteins were refolded by step-wise dialysis into 100 mM Tris HCl, pH 8.0/0.1 M NaCl/5 mM DTT/1% CHAPS, and then stored at −20° C. Polyacrylamide gel (SDS-PAGE; 12% gel) electrophoretic analysis of the polypeptide purified from the bacterial lysates was then used to determine the molecular weight and the purity of the resultant fusion polypeptide are determined. SDS-PAGE results are presented in FIG. 4.

EXAMPLE 5

In vitro Enzymatic Assay for TDP Activity

This Example describes experiments involved in the development of in vitro enzymatic assay systems for TDP activity. Recombinant human TDP protein was obtained (e.g., as described above in Examples 3 and 4) and used in these experiments.

Figure 6:
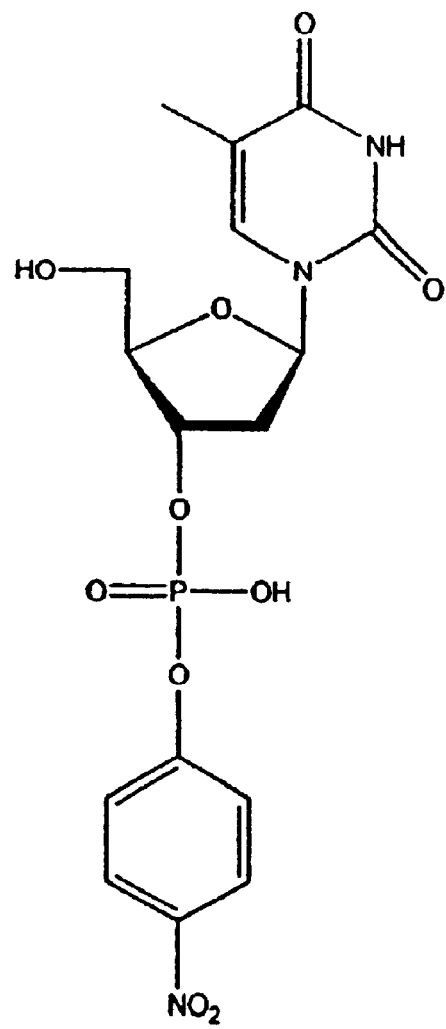

In these assays, a chromogenic enzymatic assay system is used. In these systems, a substrate of smaller molecular weight (i.e., as compared with other substrates) containing one single base of thymidine, with chromogenic para-nitrophenyl group attached to the 3'-hydroxy group of deoxyribose was chosen. This compound mimics the aromatic groups of tyrosine in topo I-DNA complexes. The compound, para-nitrophenyl thymidine-3'-phosphate is shown in FIG. 6. The compound was synthesized according to the procedure of Turner et al. (Turner et al., J. Am. Chem. Soc., 81:4651–4656 [1959]).

Upon the cleavage of the phosphodiester bond by TDP, the p-nitrophenol group mimicking the tyrosine residue in topo I-DNA complexes is released. The concentration of this group (i.e., a chromogen) is determined using spectroscopy. Thus, in this Example, enzymatic reactions contained 100 mM Tris HCl, pH 8.5, 100 mM NaCl, 1 mM DTT, 5 mM para-nitrophenyl thymidine-3'-phosphate and 5 μg of purified protein in a volume of 200 μl. For these reactions, 96-well plates were used. The amount of cleaved product (p-nitrophenol) was assessed by determining its absorbance at 415 nm (Ultramark Microplate Imaging System, BioRad).

During the development of this assay system, it was determined that the system may be optimized by the inclusion of manganese cation in the assay. Inclusion of manganese cation increases the sensitivity of the detection of enzymatic activity. Upon incubation of various TDP mutants and the substrate (para-nitrophenyl-thymidine-3'-phosphate) in the presence of manganese cations, the concentrations of the resulting para-nitrophenynol were calculated based on the optical density measured at 415 nm.

EXAMPLE 6

Effects of Co-Factors in In Vitro Enzymatic Assays

The effects of cations in the reaction systems mentioned in Example 5 are described in this Example. These experiments were conducted in order to optimize the assay system.

Figure 7:
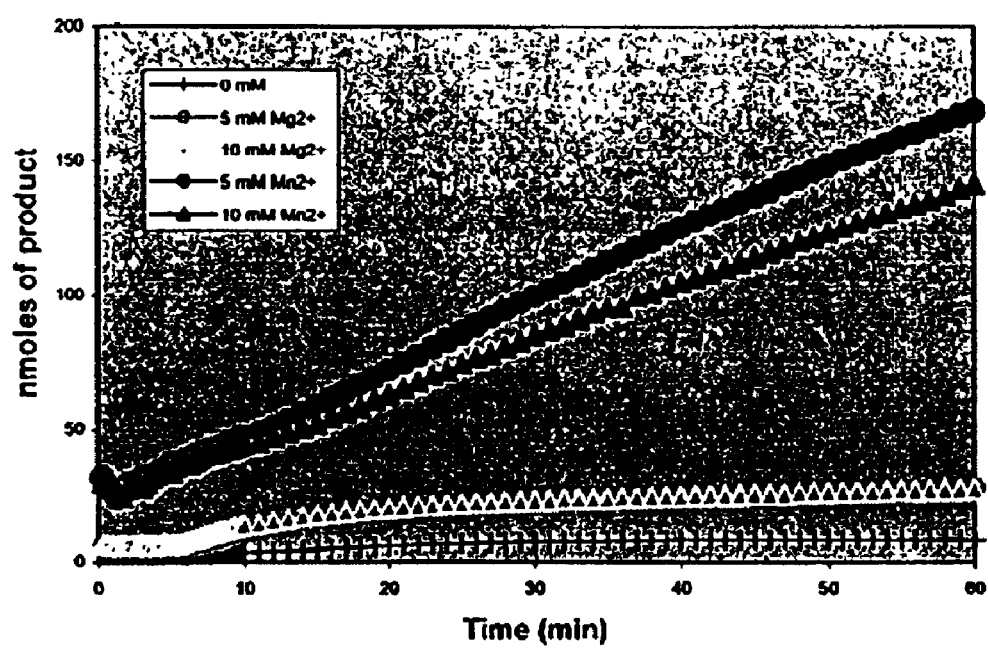
FIG. 7 provides a graph showing the effects of cations $Mn^{2+}$ and $Mg^{2+}$ on the activity of HTDPNΔ1–39 (5 mM of substrate and 5 μg of protein).

In these experiments, either manganese chloride or magnesium chloride were used at concentrations of 5 mM or 10 mM in the enzymatic reactions described in Example 5. As indicated in FIG. 7, the enzymatic activity on para-nitrophenyl thymidine-3'-phosphate in the presence of manganese was found to be increased 7-fold, as compared to the activity in the presence of magnesium, and 17-fold as compared with the activity in the absence of cations.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in cell biology, medicine, assay systems, diagnostics, and molecular biology, as well as related fields are intended to be within the scope of the present invention.

We claim:

1. A method of determining tyrosine-DNA phosphodiesterase activity, comprising:
   a. providing:
      i. tyrosine-DNA phosphodiesterase:
      ii. p-nitrophenyl thymidine-3'-phosphate; and
      iii. manganese cation:
   b. combining said tyrosine-DNA phosphodiesterase, said p-nitrophenyl thymidine-3'-phosphate and said manganese cation under conditions wherein the tyrosine-DNA phosphodiesterase reacts with the p-nitrophenyl thymidine-3'-phosphate to release t,-nitrophenyl; and
   c. detecting said p-nitrophenyl, wherein said tyrosine-DNA phosphodiesterase is human tyrosine-DNA phosphodiesterase comprising amino acid sequence SEQ ID NQ:2.

2. The A method of determining tyrosine-DNA phosphodiesterase activity, comprising:
   a. providing:
      i. tyrosine-DNA phosphodiesterase:
      ii. p-nitrophenyl thymidine-3'-phosphate; and
      iii. manganese cation:
   b. combining said tyrosine-DNA phosphodiesterase, said p-nitrophenyl thymidine-3'-phosphate and said manganese cation under conditions wherein the tyrosine-DNA phosphodiesterase reacts with the p-nitrophenyl thymidine-3'-phosphate to release p-nitrophenyl; and
   c. detecting said p-nitrophenyl,
   wherein said tyrosine-DNA phosphodiesterase has an amino acid sequence comprising an amino acid sequence selected from the group consisting of SEQ ID NOS:8, 10, 12 and 14.

3. A method of determining tyrosine-DNA phosphodiesterase activity, comprising:

a. providing:
   i. tyrosine-DNA phosphodiesterase; and
   ii. n-nitrophenyl thymidine-3'-phosphate;
b. combining said tyrosine-DNA phosphodiesterase and said p-nitrophenyl thymidine-3'-phosphate under conditions wherein the tyrosine-DNA phosphodiesterase reacts with the n-nitrophenyl thymidine-3'-phosphate to release p-nitrophenyl; and
c. detecting said p-nitrophenyl;

wherein said tyrosine-DNA phosphodiesterase is human tyrosine-DNA phosphodiesterase comprising amino acid sequence SEQ ID NO:2.

4. A method of claim determining tyrosine-DNA phosphodiesterase activity, comprising:
a. providing:
   i. a tyrosine-DNA phosphodiesterase; and
   ii. p-nitrophenyl thymidine-3'-phosphate;
b. combining said tyrosine-DNA phosphodiesterase and said p-nitrophenyl thymidine-3'-phosphate under conditions wherein the tyrosine-DNA phosphodiesterase reacts with the n-nitrophenyl thymidine-3'-phosphate to release p-nitrophenyl; and
c. detecting said p-nitrophenyl, wherein said tyrosine-DNA phosphodiesterase has an amino acid sequence comprising an amino acid sequence selected from the group consisting of SEQ ID NOS:8, 10, 12 and 14.

5. A method of determining modulation of tyrosine-DNA phosphodiesterase activity; comprising:
a. providing:
   i. tyrosine-DNA phosphodiesterase;
   ii. a compound suspected of modulating tyrosine-DNA phosphodiesterase activity; and
   iii. p-nitrophenyl thymidine-3'-phosphate;
b. combining said tyrosine-DNA phosphodiesterase and said p-nitrophenyl thymidine-3'-phosphate in the presence and absence of said compound suspected of modulating tyrosine-DNA phosphodiesterase activity under conditions wherein the tyrosine-DNA phosphodiesterase reacts with p-nitrophenyl thymidine-3'-phosphate to release p-nitrophenyl in the presence and absence of said compound suspected of modulating tyrosine-DNA phosphodiesterase activity; and
c. detecting said p-nitrophenyl, wherein said tyrosine-DNA phosphodiesterase is human tyrosine-DNA phosphodiesterase comprising amino acid sequence SEQ ID NO:2.

6. A method of of determining modulation of tyrosine-DNA phosphodiesterase activity, comprising:
a. providing;
   i. tyrosine-DNA phosphodiesterase;
   ii. a compound suspected of modulating tyrosine-DNA phosphodiesterase activity; and
   iii. p-nitrophenyl thymidine-3'-phosphate;
b. combining said tyrosine-DNA phosphodiesterase and said p-nitrophenyl thymidine-3'-phosphate in the presence and absence of said compound suspected of modulating tyrosine-DNA phosphodiesterase activity under conditions wherein the tyrosine-DNA phosphodiesterase reacts with p-nitrophenyl thymidine-3'-phosphate to release p-nitrophenyl in the presence and absence of said compound suspected of modulating tyrosine-DNA phosphodiesterase activity; and
c. detecting said p-nitrophenyl wherein said tyrosine-DNA phosphodiesterase has an amino acid sequence comprising an amino acid sequence selected from the group consisting of SEQ ID NOS:8, 10, 12 and 14.

* * * * *

UNITED STATES PATENT AND TRADEMARK OFFICE
CERTIFICATE OF CORRECTION

PATENT NO. : 6,787,327 B2
DATED : September 7, 2004
INVENTOR(S) : Kan et al.

It is certified that error appears in the above-identified patent and that said Letters Patent is hereby corrected as shown below:

<u>Title page,</u>
Item [73], Assignee, should read -- Keck Graduate Institute Of Applied Life Sciences --.

Signed and Sealed this

Twenty-third Day of May, 2006

JON W. DUDAS
*Director of the United States Patent and Trademark Office*